(12) United States Patent
Shelton, IV et al.

(10) Patent No.: US 12,178,495 B2
(45) Date of Patent: Dec. 31, 2024

(54) FILTER FOR MONOPOLAR SURGICAL INSTRUMENT ENERGY PATH

(71) Applicant: Ethicon LLC, Guaynabo, PR (US)

(72) Inventors: Frederick E. Shelton, IV, Hillsboro, OH (US); David C. Yates, West Chester, OH (US)

(73) Assignee: Cilag GmbH International, Zug (CH)

( * ) Notice: Subject to any disclaimer, the term of this patent is extended or adjusted under 35 U.S.C. 154(b) by 438 days.

(21) Appl. No.: 17/136,137

(22) Filed: Dec. 29, 2020

(65) Prior Publication Data

US 2022/0202474 A1    Jun. 30, 2022

(51) Int. Cl.
*A61B 18/14* (2006.01)
*A61B 18/12* (2006.01)
*A61B 18/16* (2006.01)

(52) U.S. Cl.
CPC ...... *A61B 18/1445* (2013.01); *A61B 18/1206* (2013.01); *A61B 18/16* (2013.01); *A61B 2018/1253* (2013.01); *A61B 2018/126* (2013.01); *A61B 2018/128* (2013.01); *A61B 2018/1286* (2013.01);
(Continued)

(58) Field of Classification Search
CPC . A61B 18/1445; A61B 18/1206; A61B 18/16; A61B 2018/1253; A61B 2018/147; A61B 2018/165
See application file for complete search history.

(56) References Cited

U.S. PATENT DOCUMENTS

| 4,184,492 A | 1/1980 | Meinke et al. |
| 5,312,401 A | 5/1994 | Newton et al. |
| 7,070,420 B1 | 7/2006 | Wakefield et al. |

(Continued)

FOREIGN PATENT DOCUMENTS

| EP | 2926752 A2 | 10/2015 |
| EP | 3417797 A1 | 12/2018 |

(Continued)

OTHER PUBLICATIONS

U.S. Appl. No. 17/136,139, entitled "Electrosurgical Instrument System with Parasitic Energy Loss Monitor," filed Dec. 29, 2020.
(Continued)

*Primary Examiner* — Joseph A Stoklosa
*Assistant Examiner* — Annie L Shoulders
(74) *Attorney, Agent, or Firm* — Frost Brown Todd LLP

(57) ABSTRACT

An electrosurgical system includes an instrument, an RF energy generator, and two ground pads. The instrument includes an electrode and a conductive shield that is configured to collect a capacitive coupling current that is induced by the application of RF energy to tissue by the electrode. A first electrical lead couples the first ground pad with the ground return of the conductive shield and the generator. The ground return is configured to divert a first portion of the capacitive coupling current to the generator via the first electrical lead. A second electrical lead couples the second ground pad with the ground return of the conductive shield and the generator. The ground return is configured to divert a second portion of the capacitive coupling current to the generator via the second electrical lead. The first and second portions of the capacitive coupling current are substantially equal.

20 Claims, 22 Drawing Sheets

(52) U.S. Cl.
CPC . *A61B 2018/1293* (2013.01); *A61B 2018/147* (2013.01); *A61B 2018/165* (2013.01)

(56) References Cited

U.S. PATENT DOCUMENTS

| | | |
|---|---|---|
| 7,354,440 B2 | 4/2008 | Truckai et al. |
| 7,381,209 B2 | 6/2008 | Truckai et al. |
| 7,762,958 B1 | 7/2010 | Webler |
| 8,663,220 B2 | 3/2014 | Wiener et al. |
| 8,820,605 B2 | 9/2014 | Shelton, IV |
| 9,125,662 B2 | 9/2015 | Shelton, IV |
| 9,314,308 B2 | 4/2016 | Parihar et al. |
| 9,949,785 B2 | 4/2018 | Price et al. |
| 10,090,616 B1 | 10/2018 | Leimbach et al. |
| 10,624,709 B2 | 4/2020 | Remm |
| 10,639,038 B2 | 5/2020 | Scott et al. |
| 10,813,640 B2 | 10/2020 | Adams et al. |
| 10,835,307 B2 | 11/2020 | Shelton, IV et al. |
| 10,842,523 B2 | 11/2020 | Shelton, IV et al. |
| 2002/0128643 A1 | 9/2002 | Simpson et al. |
| 2004/0206365 A1 | 10/2004 | Knowlton |
| 2006/0041251 A1* | 2/2006 | Odell ............... A61B 18/1233 606/34 |
| 2006/0041252 A1 | 2/2006 | Odell et al. |
| 2006/0079874 A1 | 4/2006 | Faller et al. |
| 2007/0049919 A1* | 3/2007 | Lee ............... A61B 18/1233 606/41 |
| 2007/0191713 A1 | 8/2007 | Eichmann et al. |
| 2008/0200940 A1 | 8/2008 | Eichmann et al. |
| 2009/0036884 A1* | 2/2009 | Gregg ............... A61B 18/1233 606/35 |
| 2010/0042097 A1 | 2/2010 | Newton et al. |
| 2011/0034910 A1 | 2/2011 | Ross et al. |
| 2012/0292367 A1 | 11/2012 | Morgan et al. |
| 2013/0123783 A1 | 5/2013 | Marczyk et al. |
| 2014/0249557 A1 | 9/2014 | Koch, Jr. et al. |
| 2015/0313628 A1 | 11/2015 | Allen, IV |
| 2015/0320481 A1* | 11/2015 | Cosman, Jr. ........... A61B 34/10 606/35 |
| 2016/0143685 A1 | 5/2016 | Friedrichs |
| 2016/0192980 A1 | 7/2016 | Newton et al. |
| 2016/0296268 A1 | 10/2016 | Gee et al. |
| 2017/0202591 A1 | 7/2017 | Shelton, IV et al. |
| 2017/0202605 A1 | 7/2017 | Shelton, IV et al. |
| 2017/0202608 A1 | 7/2017 | Shelton, IV et al. |
| 2018/0012719 A1 | 1/2018 | Houbre et al. |
| 2018/0078170 A1* | 3/2018 | Panescu ............... A61B 5/01 |
| 2018/0132850 A1 | 5/2018 | Leimbach et al. |
| 2018/0333185 A1 | 11/2018 | Asher et al. |
| 2019/0142492 A1 | 5/2019 | Kollmann et al. |
| 2019/0189903 A1 | 6/2019 | Benedict et al. |
| 2019/0201047 A1* | 7/2019 | Yates ............... A61B 18/1445 |
| 2019/0201075 A1 | 7/2019 | Shelton, IV et al. |
| 2019/0201077 A1 | 7/2019 | Yates et al. |
| 2019/0247680 A1 | 8/2019 | Mayer et al. |
| 2019/0290269 A1 | 9/2019 | Shelton, IV et al. |
| 2019/0290273 A1 | 9/2019 | Shelton, IV et al. |
| 2019/0290308 A1 | 9/2019 | Worthington et al. |
| 2020/0069365 A1* | 3/2020 | Harlev ............... A61B 18/1492 |
| 2020/0078075 A1 | 3/2020 | Katsuragi |
| 2020/0384502 A1 | 12/2020 | Downey et al. |
| 2021/0059709 A1 | 3/2021 | Black et al. |

FOREIGN PATENT DOCUMENTS

| | | |
|---|---|---|
| EP | 3420918 A1 | 1/2019 |
| EP | 3461447 A1 | 4/2019 |
| EP | 3479787 A1 | 5/2019 |
| EP | 3542733 A1 | 9/2019 |
| WO | WO 1992/008417 A1 | 5/1992 |
| WO | WO 2018/165425 A1 | 9/2018 |
| WO | WO 2019/130111 A1 | 7/2019 |
| WO | WO 2020/051462 A1 | 3/2020 |

OTHER PUBLICATIONS

U.S. Appl. No. 17/136,141, entitled "Energized Surgical Instrument System with Multi-Generator Output Monitoring," filed Dec. 29, 2020.
U.S. Appl. No. 17/136,145, entitled "Electrosurgical Instrument with Shaft Voltage Monitor," filed Dec. 29, 2020.
U.S. Appl. No. 17/136,154, entitled "Electrosurgical Instrument with Electrical Resistance Monitor at Rotary Coupling," filed Dec. 29, 2020.
U.S. Appl. No. 17/136,158, entitled "Electrosurgical Instrument with Modular Component Contact Monitoring," filed Dec. 29, 2020.
International Search Report and Written Opinion dated May 17, 2022, for International Application No. PCT/IB2021/062411, 20 pages.
International Search Report and Written Opinion dated Mar. 22, 2022, for International Application No. PCT/IB2021/062413, 13 pages.
International Search Report and Written Opinion dated Mar. 24, 2022, for International Application No. PCT/IB2021/062414, 17 pages.
International Search Report and Written Opinion dated Mar. 24, 2022, for International Application No. PCT/IB2021/062416, 16 pages.
International Search Report and Written Opinion dated Mar. 30, 2022, for International Application No. PCT/IB2021/062417, 17 pages.
International Search Report and Written Opinion dated Apr. 7, 2022, for International Application No. PCT/IB2021/062418, 13 pages.

* cited by examiner

FILTER FOR MONOPOLAR SURGICAL INSTRUMENT ENERGY PATH

BACKGROUND

A variety of ultrasonic surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein, in its entirety; U.S. Pub. No. 2007/0191713, entitled "Ultrasonic Device for Cutting and Coagulating," published Aug. 16, 2007, now abandoned, the disclosure of which is incorporated by reference herein, in its entirety; and U.S. Pub. No. 2008/0200940, entitled "Ultrasonic Device for Cutting and Coagulating," published Aug. 21, 2008, now abandoned, the disclosure of which is incorporated by reference herein, in its entirety.

Some instruments are operable to seal tissue by applying radiofrequency (RF) electrosurgical energy to the tissue. Examples of such devices and related concepts are disclosed in U.S. Pat. No. 7,354,440, entitled "Electrosurgical Instrument and Method of Use," issued Apr. 8, 2008, the disclosure of which is incorporated by reference herein, in its entirety; U.S. Pat. No. 7,381,209, entitled "Electrosurgical Instrument," issued Jun. 3, 2008, the disclosure of which is incorporated by reference herein, in its entirety.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein, in its entirety; and U.S. Pat. No. 8,663,220, entitled "Ultrasonic Electrosurgical Instruments," issued Mar. 4, 2014, the disclosure of which is incorporated by reference herein, in its entirety.

In some scenarios, it may be preferable to have surgical instruments grasped and manipulated directly by the hand or hands of one or more human operators. In addition, or as an alternative, it may be preferable to have surgical instruments controlled via a robotic surgical system. Examples of robotic surgical systems and associated instrumentation are disclosed in U.S. Pat. No. 10,624,709, entitled "Robotic Surgical Tool with Manual Release Lever," issued on Apr. 21, 2020, the disclosure of which is incorporated by reference herein, in its entirety; U.S. Pat. No. 9,314,308, entitled "Robotic Ultrasonic Surgical Device With Articulating End Effector," issued on Apr. 19, 2016, the disclosure of which is incorporated by reference herein, in its entirety; U.S. Pat. No. 9,125,662, entitled "Multi-Axis Articulating and Rotating Surgical Tools," issued Sep. 8, 2015, the disclosure of which is incorporated by reference herein, in its entirety; U.S. Pat. No. 8,820,605, entitled "Robotically-Controlled Surgical Instruments," issued Sep. 2, 2014, the disclosure of which is incorporated by reference herein, in its entirety; U.S. Pub. No. 2019/0201077, entitled "Interruption of Energy Due to Inadvertent Capacitive Coupling," published Jul. 4, 2019, issued as U.S. Pat. No. 11,291,495 on Apr. 5, 2022, the disclosure of which is incorporated by reference herein, in its entirety; U.S. Pub. No. 2012/0292367, entitled "Robotically-Controlled End Effector," published on Nov. 11, 2012, now abandoned, the disclosure of which is incorporated by reference herein, in its entirety; and U.S. patent application Ser. No. 16/556,661, entitled "Ultrasonic Surgical Instrument with a Multi-Planar Articulating Shaft Assembly," filed on Aug. 30, 2019, published as 2021/0059709 on Mar. 4, 2021, issued as U.S. Pat. No. 11,690,642 on Jul. 4, 2023, the disclosure of which is incorporated by reference herein, in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
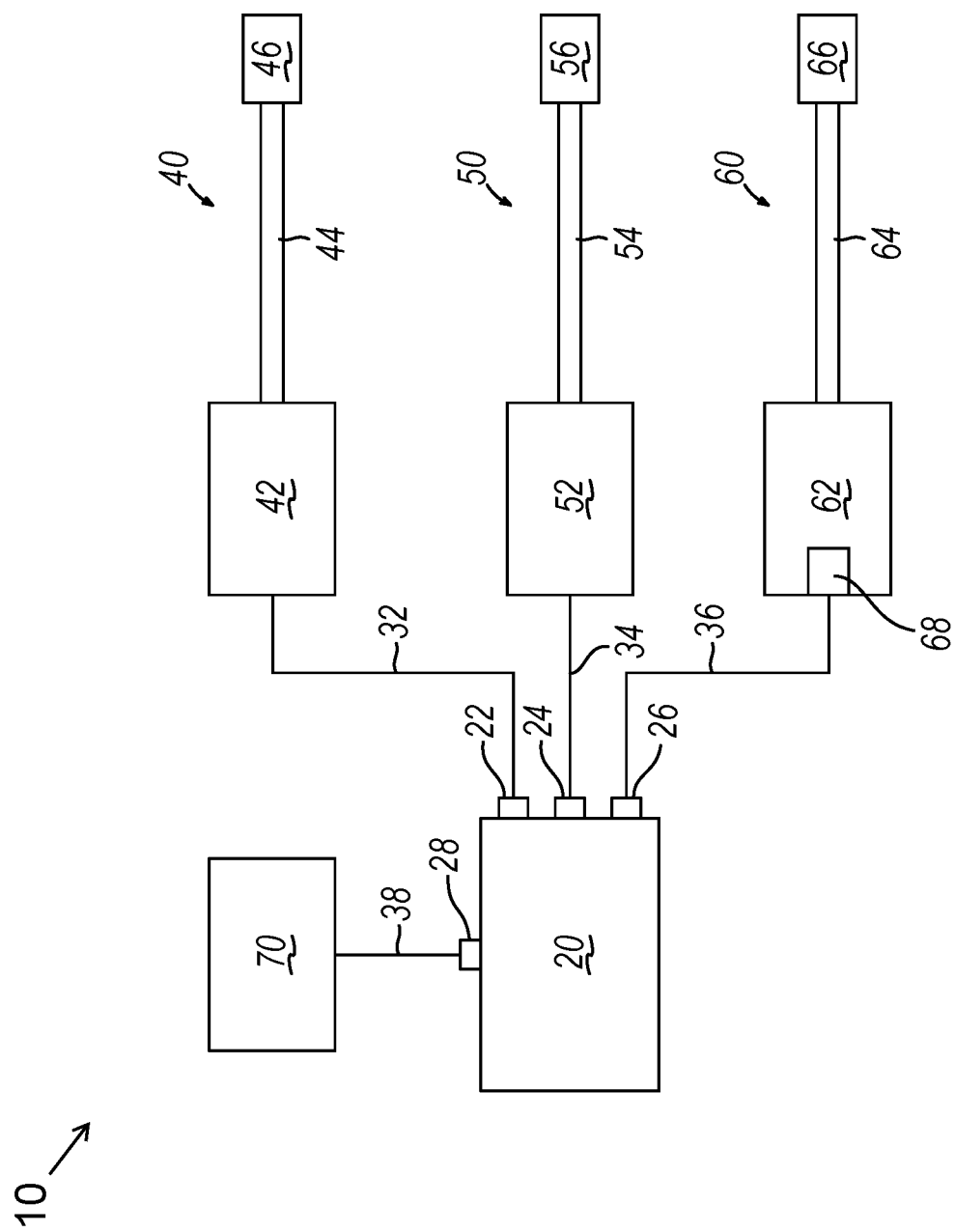
FIG. 1 depicts a schematic view of an example of a robotic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "top," "bottom," "above," and "below," are used with respect to the examples and associated figures and are not intended to unnecessarily limit the invention described herein.

I. Example of a Robotic Surgical System

As noted above, in some surgical procedures, it may be desirable to utilize a robotically controlled surgical system. Such a robotically controlled surgical system may include one or more surgical instruments that are controlled and driven robotically via one or more users that are either in the same operating room or remote from the operating room. FIG. 1 illustrates on example of various components that may be incorporated into a robotic surgical system (10). System (10) of this example includes a console (20), a monopolar RF electrosurgical instrument (40), a bipolar RF electrosurgical instrument (50), and an ultrasonic surgical instrument (60). While FIG. 1 shows all three instruments (40, 50, 60) coupled with console (20) at the same time, there may be usage scenarios where only one or two of instruments (40, 50, 60) coupled with console (20) at the same time. In addition, there may be usage scenarios where various other instruments are coupled with console (20) in addition, or as an alternative to, one or more of instruments (40, 50, 60) being coupled with console (20).

Monopolar RF electrosurgical instrument (40) of the present example includes a body (42), a shaft (44) extending distally from body (42), and an end effector (46) at the distal end of shaft (44). Body (42) is configured to couple with a robotic arm (not shown in FIG. 1) of system (10), such that the robotic arm is operable to position and orient monopolar RF electrosurgical instrument (40) in relation to a patient. In versions where monopolar RF electrosurgical instrument (40) includes one or more mechanically driven components (e.g., jaws at end effector (46), articulating sections of shaft (44), rotating sections of shaft (44), etc.), body (42) may include various components that are operable to convert one or more mechanical drive inputs from the robotic arm into motion of the one or more mechanically driven components of monopolar RF electrosurgical instrument (40).

As also shown in FIG. 1, body (42) is coupled with a corresponding port (22) of console (20) via a cable (32). Console (20) is operable to provide electrical power to monopolar RF electrosurgical instrument (40) via port (22) and cable (32). In some versions, port (22) is dedicated to driving monopolar RF electrosurgical instruments like monopolar RF electrosurgical instrument (40). In some other versions, port (22) is operable to drive various kinds of instruments (e.g., including instruments (50, 60), etc.). In some such versions, console (20) is operable to automatically detect the kind of instrument (40, 50, 60) that is coupled with port (22) and adjust the power profile to port (22) accordingly. In addition, or in the alternative, console (20) may adjust the power profile to port (22) based on a selection made by an operator via console (20), manually identifying the kind of instrument (40, 50, 60) that is coupled with port (22).

Shaft (44) is operable to support end effector (46) and provides one or more wires or other paths for electrical communication between base (42) and end effector (46). Shaft (44) is thus operable to transmit electrical power from console (20) to end effector (46). Shaft (44) may also include various kinds of mechanically movable components, including but not limited to rotating segments, articulating sections, and/or other kinds of mechanically movable components as will be apparent to those skilled in the art in view of the teachings herein.

End effector (46) of the present example includes an electrode that is operable to apply monopolar RF energy to tissue. Such an electrode may be incorporated into a sharp blade, a needle, a flat surface, some other atraumatic structure, or any other suitable kind of structure as will be apparent to those skilled in the art in view of the teachings herein. End effector (46) may also include various other kinds of components, including but not limited to grasping jaws, etc.

System (10) of this example further includes a ground pad (70) that is coupled with a corresponding port (28) of console (20) via a cable (38). In some versions, ground pad (70) is incorporated into a patch or other structure that is adhered to the skin of the patient (e.g., on the thigh of the patient). In some other versions, ground pad (70) is placed under the patient (e.g., between the patient and the operating table). In either case, ground pad (70) may serve as a return path for monopolar RF energy that is applied to the patient via end effector (46). In some versions, port (28) is a dedicated ground return port. In some other versions, port (28) is a multi-purpose port that is either automatically designated as a ground return port upon console (20) detecting the coupling of ground pad (70) with port (28) or manually designated as a ground return port via an operator using a user input feature of console (20).

Bipolar RF electrosurgical instrument (50) of the present example includes a body (52), a shaft (54) extending distally from body (52), and an end effector (56) at the distal end of shaft (54). Each of these components (52, 54, 56) may be configured and operable in accordance with the above description of corresponding components (42, 44, 46) of monopolar RF electrosurgical instrument (50), except that end effector (56) of this example is operable to apply bipolar RF energy to tissue. Thus, end effector (56) includes at least two electrodes, with those two electrodes being configured to cooperate with each other to apply bipolar RF energy to tissue. Bipolar RF electrosurgical instrument (50) is coupled with console (20) via a cable (34), which is further coupled with a port (24) of console (20). Port (24) may be dedicated to powering bipolar RF electrosurgical instruments. Alternatively, port (24) or may be a multi-purpose port whose output is determined based on either automatic detection of bipolar RF electrosurgical instrument (50) or operator selection via a user input feature of console (20).

Ultrasonic surgical instrument (60) of the present example includes a body (62), a shaft (64) extending distally from body (62), and an end effector (66) at the distal end of shaft (64). Each of these components (62, 64, 66) may be configured and operable in accordance with the above description of corresponding components (42, 44, 46) of monopolar RF electrosurgical instrument (50), except that end effector (66) of this example is operable to apply ultrasonic energy to tissue. Thus, end effector (66) includes an ultrasonic blade or other ultrasonically vibrating element. In addition, base (62) includes an ultrasonic transducer (68) that is operable to generate ultrasonic vibrations in response to electrical power, while shaft (64) includes an acoustic waveguide that is operable to communicate the ultrasonic vibrations from transducer (68) to end effector (66).

Ultrasonic surgical instrument (60) is coupled with console (20) via a cable (36), which is further coupled with a port (26) of console (20). Port (26) may be dedicated to powering ultrasonic electrosurgical instruments. Alternatively, port (26) or may be a multi-purpose port whose output is determined based on either automatic detection of ultrasonic instrument (60) or operator selection via a user input feature of console (20).

While FIG. 1 shows monopolar RF, bipolar RF, and ultrasonic capabilities being provided via three separate, dedicated instruments (40, 50, 60), some versions may include an instrument that is operable to apply two or more of monopolar RF, bipolar RF, or ultrasonic energy to tissue. In other words, two or more of such energy modalities may be incorporated into a single instrument. Examples of how such different modalities may be integrated into a single instrument are described in U.S. Pub. No. 2017/0202591, entitled "Modular Battery Powered Handheld Surgical Instrument with Selective Application of Energy Based on Tissue Characterization," published Jul. 20, 2017, issued as U.S. Pat. No. 11,229,471 on Jan. 25, 2022, the disclosure of which is incorporated by reference herein, in its entirety. Other examples will be apparent to those skilled in the art in view of the teachings herein.

Figure 2:
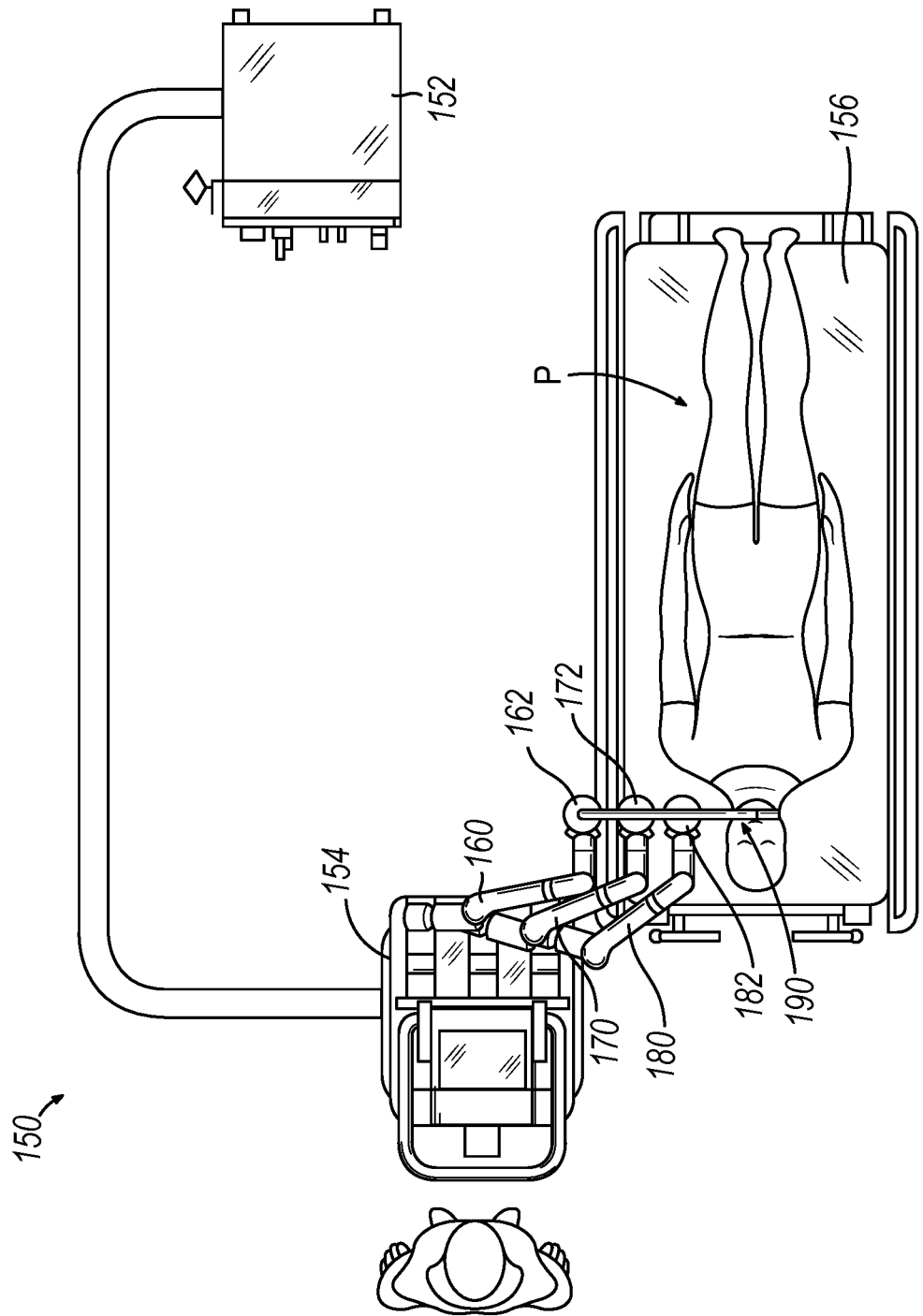
FIG. 2 depicts a schematic view of an example of a robotic surgical system being used in relation to a patient.

FIG. 2 shows an example of a robotic surgical system (150) in relation to a patient (P) on a table (156). System (150) of this example includes a control console (152) and a drive console (154). Console (152) is operable to receive user inputs from an operator; while drive console (154) is operable to convert those user inputs into motion of a set of robotic arms (160, 170, 180). In some versions, consoles (152, 154) collectively form an equivalent to console (20) described above. While consoles (152, 154) are shown as separate units in this example, consoles (152, 154) may in fact be combined as a single unit in some other examples.

Robotic arms (160, 170, 180) extend from drive console (154) in this example. In some other versions, robotic arms (160, 170, 180) are integrated into table (156) or some other structure. Each robotic arm (160, 170, 180) has a corresponding drive interface (162, 172, 182). In this example, three drive interfaces (162, 172, 182) are coupled with one single instrument assembly (190). In some other scenarios, each drive interface (162, 172, 182) is coupled with a separate respective instrument. By way of example only, a drive interface (162, 172, 182) may couple with a body of an instrument, like bodies (42, 52, 62) of instruments (40, 50, 60) described above. In any case, robotic arms (160, 170, 180) may be operable to move instrument (40, 50, 60, 190) in relation to the patient (P) and actuate any mechanically driven components of instrument (40, 50, 60, 190). Robotic arms (160, 170, 180) may also include features that provide a pathway for communication of electrical power to instrument (40, 50, 60, 190). For instance, cables (32, 34, 36) may be at least partially integrated into robotic arms (160, 170, 180). In some other versions, robotic arms (160, 170, 180) may include features to secure but not necessarily integrate cables (32, 34, 36). As yet another variation, cables (32, 34, 36) may simply stay separate from robotic arms (160, 170, 180). Other suitable features and arrangements that may be used to form robotic surgical systems (10, 150) will be apparent to those skilled in the art in view of the teachings herein.

In robotic surgical systems like robotic surgical systems (10, 150), each port (22, 24, 26, 28) may have a plurality of electrical features providing inputs and outputs between console (20, 152) and robotic arms (160, 170, 180) and/or instruments (40, 50, 60, 190). These electrical features may include sockets, pins, contacts, or various other features that are in close proximity with each other. In some scenarios, this proximity may provide a risk of power or signals undesirably crossing from one electrical feature to another electrical feature, which may cause equipment failure, equipment damage, sensor errors, and/or other undesirable results. In addition, or in the alternative, this proximity may provide a risk of generating electrical potentials between proximate components or creating capacitive couplings between electrical features. Such capacitive coupling may provide undesirable results such as power reductions, signal reductions, signal interference, patient injuries, and/or other undesirable results. It may therefore be desirable to provide features to prevent or otherwise address such occurrences at ports (22, 24, 26, 28).

Similarly, each robotic arm (160, 170, 180), each cable (32, 34, 36, 38), and/or each instrument (40, 50, 60, 190) may include a plurality of wires, traces in rigid or flexible circuits, and other electrical features that are in close proximity with each other. Such electrical features may also be in close proximity with other components that are not intended to provide pathways for electrical communication but are nevertheless formed of an electrically conductive material. Such electrically conductive mechanical features may include moving components (e.g., drive cables, drive bands, gears, etc.) or stationary components (e.g., chassis or frame members, etc.). This proximity may provide a risk of power or signals undesirably crossing from one electrical feature to another electrical feature and/or from one electrical feature to an electrically conductive mechanical feature, which may cause equipment failure, equipment damage, sensor errors, and/or other undesirable results. In addition, or in the alternative, this proximity may provide a risk of generating electrical potentials between proximate components or creating capacitive couplings between electrical features and/or between an electrical feature and an electrically conductive mechanical feature. Such capacitive coupling may provide undesirable results such as power reductions, signal reductions, signal interference, patient injuries, and/or other undesirable results. It may therefore be desirable to provide features to prevent or otherwise address such occurrences within robotic arms (160, 170, 180), within cables (32, 34, 36, 38), and/or within instruments (40, 50, 60, 190).

II. Example of Handheld Surgical Instrument

Figure 3:
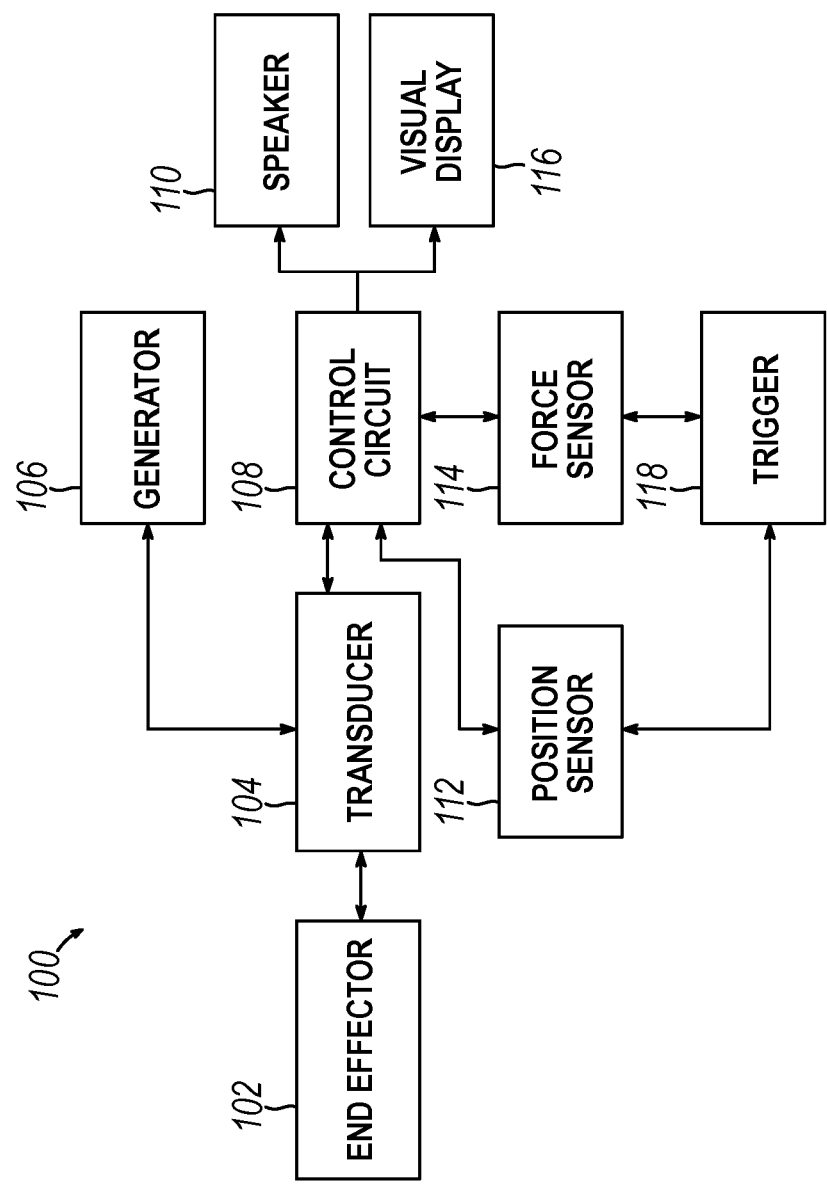
FIG. 3 depicts a schematic view of examples of components that may be incorporated into a surgical instrument.

In some procedures, a surgeon may prefer to use a handheld surgical instrument in addition to, or in lieu of, using a robotic surgical system (10, 150). FIG. 3 illustrates an example of various components that may be integrated into a handheld surgical instrument (100). In addition to the following teachings, instrument (200) may be constructed and operable in accordance with at least some of the teachings of U.S. Pub. No. 2017/0202608, entitled "Modular Battery Powered Handheld Surgical Instrument Containing Elongated Multi-Layered Shaft," published Jul. 20, 2017, issued as U.S. Pat. No. 10,835 on Nov. 17, 2020, the disclosure of which is incorporated by reference herein, in its entirety; and/or various other references cited herein. Instrument (100) of this example includes an end effector (102), an ultrasonic transducer (104), a power generator (106), a control circuit (108), a speaker (110), a position sensor (112), a force sensor (114), a visual display (116), and a trigger (118). In some versions, end effector (102) is disposed at a distal end of a shaft (not shown in FIG. 3), while the other components (104, 106, 108, 110, 112, 114, 116, 118) are incorporated into a handle assembly (not shown in FIG. 3) at the proximal end of the shaft. Some variations may also provide some of components (104, 106, 108, 110, 112, 114, 116, 118) in a separate piece of capital equipment. For instance, power generator (106), speaker (110), and/or visual display (116) may be incorporated into a separate piece of capital equipment that is coupled with instrument (100).

End effector (102) may be configured and operable like end effectors (46, 56, 66) described above, such that end effector (102) may be operable to apply monopolar RF energy, bipolar RF energy, or ultrasonic energy to tissue. Transducer (104) may be configured and operable like transducer (68). Generator (106) may be operable to provide electrical power as needed to drive transducer (68) and/or to provide RF energy via end effector (102). In versions where generator (106) is integrated into a handle assembly of instrument (106), generator (106) may comprise one or more battery cells, etc. Control circuit (108) may include one or more microprocessors and/or various other circuitry components that may be configured to provide signal processing and other electronic aspects of operability of instrument (100). Position sensor (112) may be configured to sense the position and/or orientation of instrument (102). In some versions, control circuit (108) is configured to vary the operability of instrument (102) based on data from position sensor (112). Force sensor (114) is operable to sense one or more force parameters associated with usage of instrument (100). Such force parameters may include force being applied to instrument (100) by the operator, force applied to tissue by end effector (102), or other force parameters as will be apparent to those skilled in the art in view of the teachings herein. In some versions, control circuit (108) is configured to vary the operability of instrument (102) based on data from force sensor (114). In some versions, one or both of sensors (112, 114) may be incorporated into end effector (102). In addition, or in the alternative, one or both of sensors (112, 114) may be incorporated into a shaft assembly (not shown) of instrument (100). Variations of instrument (100) may also incorporate various other kinds of sensors (e.g., in addition to or in lieu of sensors (112, 114) in end effector (102), in the shaft assembly, and/or elsewhere within instrument (100).

Trigger (118) is operable to control an aspect of operation of end effector (102), such as movement of a pivoting jaw, translation of a cutting blade, etc. Speaker (110) and visual display (116) are operable to provide audible and visual feedback to the operator relating to operation of instrument (100). The above-described components (102, 104, 106, 108, 110, 112, 114, 116, 118) of instrument (100) are illustrative examples, such that components (102, 104, 106, 108, 110, 112, 114, 116, 118) may be varied, substituted, supplemented, or omitted as desired.

Figure 4:
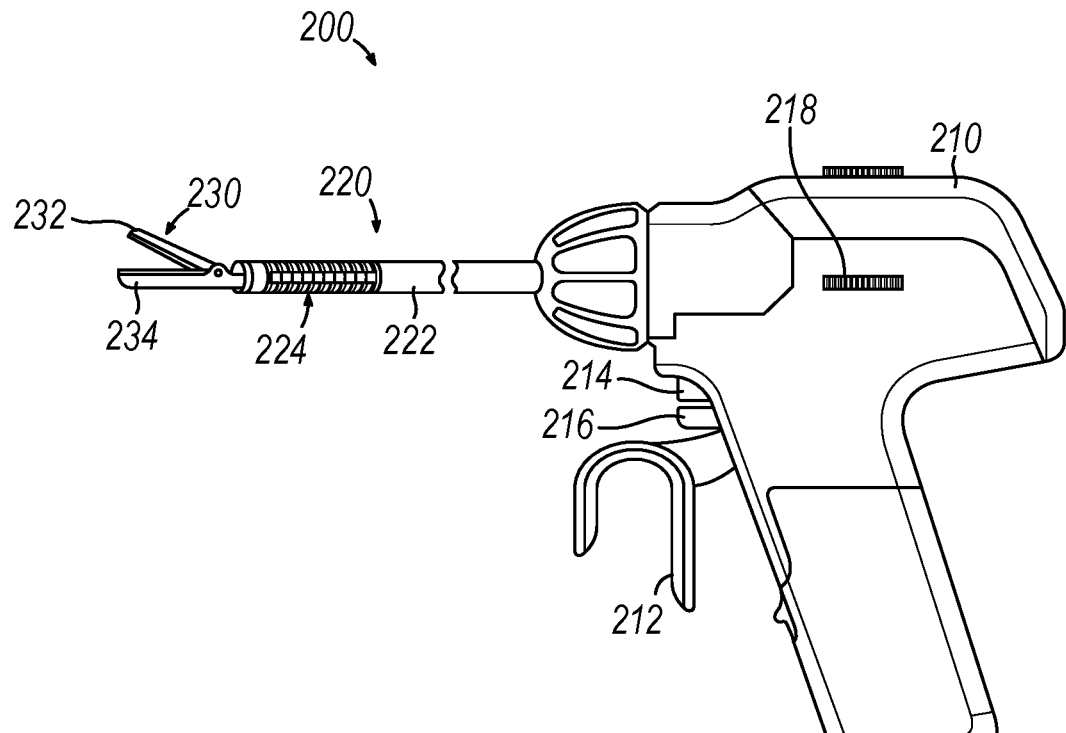
FIG. 4 depicts a side elevation view of an example of a handheld surgical instrument.

FIG. 4 shows an example of a form that instrument (100) may take. In particular, FIG. 4 shows a handheld instrument (200). In addition to the following teachings, instrument (200) may be constructed and operable in accordance with at least some of the teachings of U.S. Pub. No. 2017/0202591, issued as U.S. Pat. No. 11,229,471 on Jan. 25, 2022, the disclosure of which is incorporated by reference herein, in its entirety; and/or various other references cited herein. In the present example, instrument (200) includes a handle assembly (210), a shaft assembly (220), and an end effector (230). Handle assembly (210) includes a pivoting trigger (212), a first trigger button (214), a second trigger button (216), and an articulation control (218). Shaft assembly (220) includes a rigid shaft portion (222) and an articulation section (224). End effector (230) is distal to articulation section (224) and includes an upper jaw (232) and a lower jaw (234).

By way of example only, handle assembly (210) may include one or more of the above-described components (104, 106, 108, 110, 112, 114, 116, 118). Trigger (212) may be operable to drive upper jaw (232) to pivot toward lower jaw (234) (e.g., to grasp tissue between haws (232, 234)). Trigger buttons (214, 216) may be operable to activate delivery of energy (e.g., RF energy and/or ultrasonic energy) via end effector (230). Articulation control (218) is operable to drive deflection of shaft assembly (220) at articulation section (224), thereby driving lateral deflection of end effector (230) away from or toward the central longitudinal axis defined by rigid shaft portion (222). End effector (230) may include one or more electrodes that is/are operable to apply monopolar and/or bipolar RF energy to tissue. In addition, or in the alternative, end effector (230) may include an ultrasonic blade that is operable to apply ultrasonic energy to tissue. In some versions, end effector (230) is operable to apply two or more of monopolar RF energy, bipolar RF energy, or ultrasonic energy to tissue. Other suitable features and functionalities that may be incorporated into end effector (230) will be apparent to those skilled in the art in view of the teachings herein.

Instruments (150, 200) may include a plurality of wires, traces in rigid or flexible circuits, and other electrical features that are in close proximity with each other. Such electrical features may be located within handle assembly (210), within shaft assembly (220), and/or in end effector (230). Such electrical features may also be in close proximity with other components that are not intended to provide pathways for electrical communication but are nevertheless formed of an electrically conductive material. Such electrically conductive mechanical features may include moving components (e.g., drive cables, drive bands, gears, etc.) or stationary components (e.g., chassis or frame members, etc.). This proximity may provide a risk of power or signals undesirably crossing from one electrical feature to another electrical feature and/or from one electrical feature to an electrically conductive mechanical feature, which may cause equipment failure, equipment damage, sensor errors, patient injuries, and/or other undesirable results. In addition, or in the alternative, this proximity may provide a risk of generating electrical potentials between proximate components or creating capacitive couplings between electrical features and/or between an electrical feature and an electrically conductive mechanical feature. Such capacitive coupling may provide undesirable results such as power reductions, signal reductions, signal interference, and/or other undesirable results. It may therefore be desirable to provide features to prevent or otherwise address such occurrences within instruments (150, 200).

III. Further Examples of Surgical Instrument Components

The following description relates to examples of different features that may be incorporated into any of the various instruments (40, 50, 60, 100, 190, 200) described above. While these examples are provided separate from each other, the features described in any of the following examples may be combined with the features described in other examples described below. Thus, the below-described features may be combined in various permutations as will be apparent to those skilled in the art in view of the teachings herein. Similarly, various ways in which the below-described features may be incorporated into any of the various instruments (40, 50, 60, 100, 190, 200) described above will be apparent to those skilled in the art in view of the teachings herein. The below-described features may be incorporated into robotically controlled surgical instruments (40, 50, 60, 190) and/or handheld surgical instruments (100, 200).

A. Example of Ultrasonic End Effector

Figure 5:
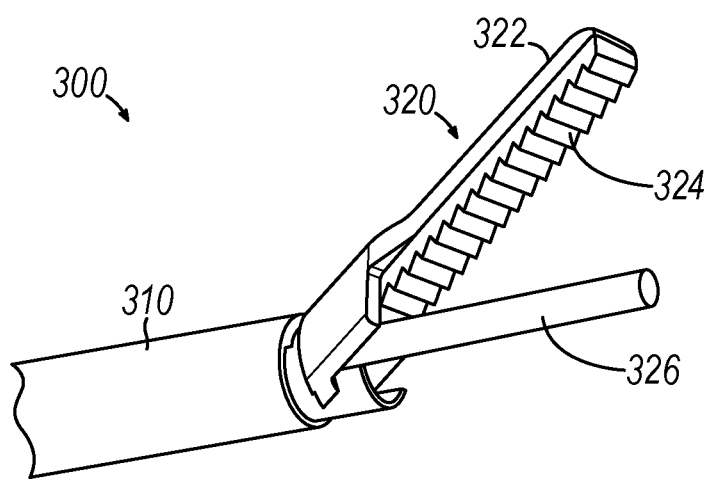
FIG. 5 depicts a perspective view of an example of an end effector that is operable to apply ultrasonic energy to tissue.

FIG. 5 shows a portion of an example of an ultrasonic instrument (300), including a shaft assembly (310) and an end effector (320). End effector (320) includes an upper jaw (322) and an ultrasonic blade (326). Upper jaw (322) is operable to pivot toward ultrasonic blade (326) to thereby compress tissue between a clamp pad (324) of upper jaw (322) and ultrasonic blade (326). When ultrasonic blade (326) is activated with ultrasonic vibrations, ultrasonic blade (326) may sever and seal tissue compressed against clamp pad (324). By way of example only, end effectors (66, 102, 230) may be configured and operable similar to end effector (320).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (300), such risks may occur with respect to an acoustic waveguide in shaft assembly (310) leading to ultrasonic blade (326), as the acoustic waveguide may be formed of an electrically conductive material. In addition, instrument (300) may include one or more sensors in shaft assembly (310) and/or end effector (320); and may also include one or more electrodes and/or other electrical features in end effector (320). Other components of instrument (350) that may present the above-described risks will be apparent to those skilled in the art in view of the teachings herein.

B. Example of Bipolar RF End Effector

Figure 6:
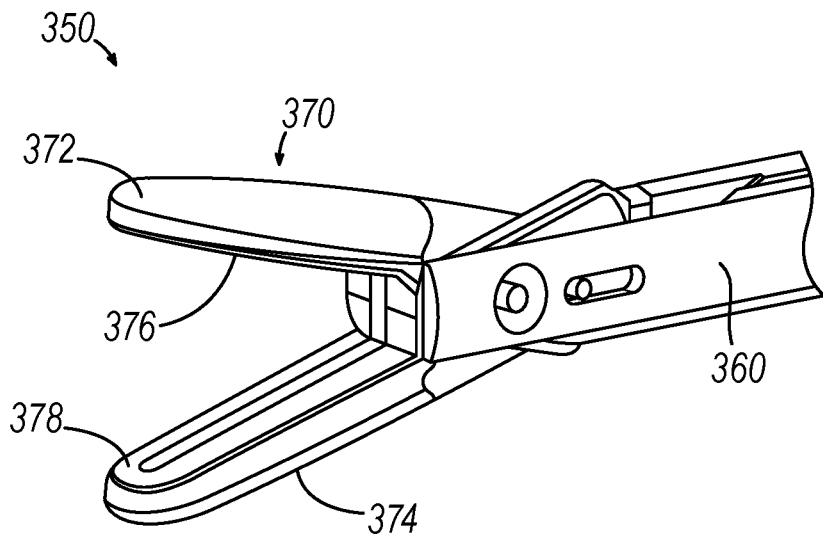
FIG. 6 depicts a perspective view of an example of an end effector that is operable to apply bipolar RF energy to tissue.

FIG. 6 shows a portion of an example of a bipolar RF instrument (350), including a shaft assembly (360) and an end effector (370). End effector (370) includes an upper jaw (372) and a lower jaw (374). Jaws (372, 374) are pivotable toward and away from each other. Upper jaw (372) includes a first electrode surface (376) while lower jaw (374) includes a second electrode surface (378). When tissue is compressed between jaws (372, 374), electrode surfaces (376, 378) may be activated with opposing polarities to thereby apply bipolar RF energy to the tissue. This bipolar RF energy may seal the compressed tissue. In some versions, end effector (370) further includes a translating knife member (not show) that is operable to sever tissue that is compressed between jaws (372, 374). Some variations of end effector (370) may also be operable to cooperate with a ground pad (e.g., ground pad (70)) to apply monopolar RF energy to tissue, such as by only activating one electrode surface (376, 378) or by activating both electrode surfaces (376, 378) at a single polarity. By way of example only, end effectors (64, 102, 230) may be configured and operable similar to end effector (370).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (350), such risks may occur with respect to electrode surface (376, 378) and the wires or other electrical features that extend along shaft assembly (360) to reach electrode surfaces (376, 378). In addition, instrument (350) may include one or more sensors in shaft assembly (360) and/or end effector (370); and may also include one or more electrodes and/or other electrical features in end effector (370). Other components of instrument (350) that may present the above-described risks will be apparent to those skilled in the art in view of the teachings herein.

C. Example of Monopolar Surgical Instrument Features

Figure 7:
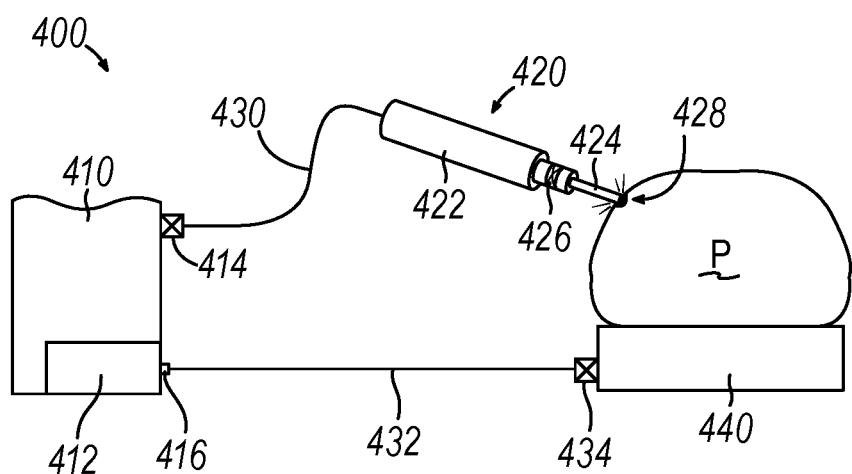
FIG. 7 depicts a schematic view of an example of a surgical instrument that is operable to apply monopolar RF energy to tissue.

FIG. 7 shows an example of a monopolar RF energy delivery system (400) that includes a power generator (410), a delivery instrument (420), and a ground pad assembly (440). In addition to the following teachings, instrument (420) may be constructed and operable in accordance with at least some of the teachings of U.S. Pub. No. 2019/0201077, issued as U.S. Pat. No. 11,291,495 on Apr. 5, 2022, the disclosure of which is incorporated by reference herein, in its entirety; and/or various other references cited herein. Power generator (410) may be operable to deliver monopolar RF energy to instrument (420) via a cable (430), which is coupled with power generator (410) via a port (414). In some versions, port (414) includes an integral sensor. By way of example only, such a sensor in port (414) may be configured to monitor whether excess or inductive energy is radiating from power generator (410) and/or other characteristics of energy being delivered from power generator (410) via port (414). Instrument (420) includes a body (422), a shaft (424), a sensor (426), and a distal electrode (428) that is configured to contact a patient (P) and thereby apply monopolar RF energy to the patient (P). By way of example only, sensor (426) may be configured to monitor whether excess or inductive energy is radiating from instrument (420). Based on signals from sensor (426), a control module in power generator (410) may passively throttle the ground return from ground pad assembly (440) based on data from sensor.

In some versions, ground pad assembly (440) comprises one or more resistive continuity ground pads that provide direct contact between the skin of the patient (P) and one or more metallic components of the ground pad. In some other versions, ground pad assembly (440) comprises a capacitive coupling ground pad that includes a gel material that is interposed between the patient (P) and the ground return plate. In the present example, ground pad assembly (440) is positioned under the patient (P) and is coupled to power generator (410) via a cable (432) via ports (416, 434). Either or both of ports (416, 434) may include an integral sensor. By way of example only, such a sensor in either or both of ports (416, 434) may be configured to monitor whether excess or inductive energy is radiating from ground pad assembly (440).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (420), such risks may occur with respect to sensor (426), distal electrode (428), and/or any other electrical components in instrument (420). Other components of instrument (420) that may present the above-described risks will be apparent to those skilled in the art in view of the teachings herein. Such risks may be greater in versions instrument (420) that are dedicated to providing monopolar RF energy than in the context of bipolar RF instruments such as instrument (350) because a dedicated monopolar RF instrument may lack a ground return path that might otherwise prevent or mitigate the above risks.

D. Example of Articulation Section in Shaft Assembly

Figure 8:
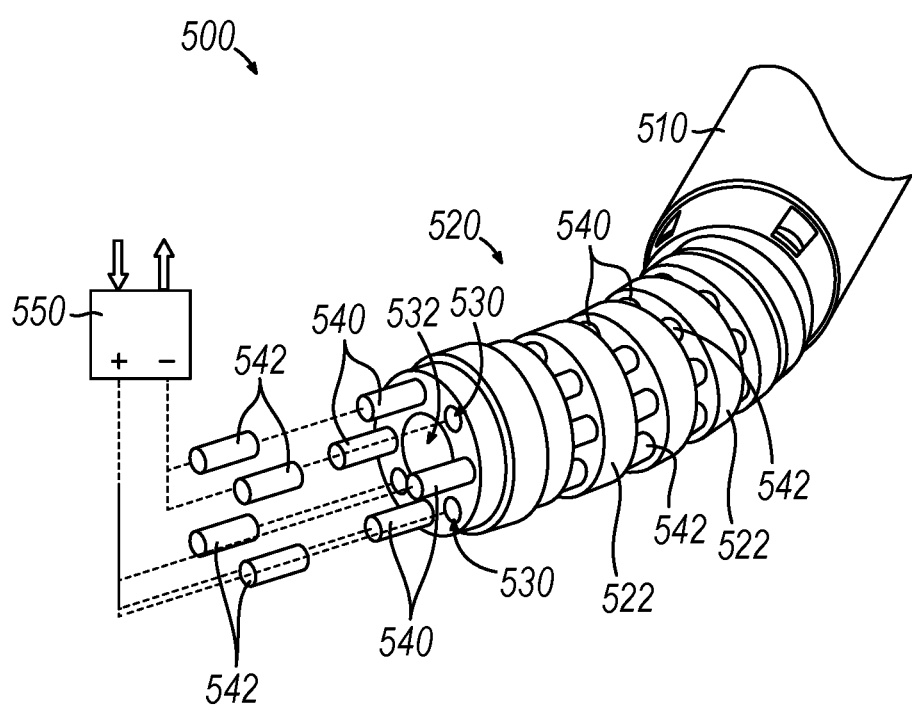
FIG. 8 depicts a perspective view of an example of an articulation section that may be incorporated into a shaft assembly of a surgical instrument.

FIG. 8 illustrates a portion of an instrument (500) that includes a shaft (510) with an articulation section (520). In addition to the following teachings, instrument (500) may be constructed and operable in accordance with at least some of the teachings of U.S. Pub. No. 2017/0202591, issued as U.S. Pat. No. 11,229,471 on Jan. 25, 2022, the disclosure of which is incorporated by reference herein, in its entirety; and/or various other references cited herein. In the present example, an end effector (550) is positioned at the distal end of articulation section (520). Articulation section (520) includes a plurality of segments (522) and is operable to laterally deflect end effector (550) away from and toward the central longitudinal axis of shaft (510). A plurality of wires (540) extend through shaft (510) and along articulation section (520) to reach end effector (550) and thereby deliver electrical power to end effector (550). By way of example only, end effector (550) may be operable to deliver monopolar and/or bipolar RF energy to tissue as described herein. A plurality of push-pull cables (542) also extend through articulation section (520). Push-pull cables (542) may be coupled with an actuator (e.g., similar to articulation control (218)) to drive articulation of articulation section (520). Segments (522) are configured to maintain separation between, and provide structural support to, wires (540) and push-pull cables (542) along the length of articulation section (520). Articulation section (520) of this example also defines a central passageway (532). By way of example only, central passageway (532) may accommodate an acoustic waveguide (e.g., in variations where end effector (550) further includes an ultrasonic blade), may provide a path for fluid communication, or may serve any other suitable purpose. Alternatively, central passageway (532) may be omitted.

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/ or electrically conductive mechanical features that may provide a risk of generating electrical potentials between proximate components or creating capacitive couplings between electrical features and/or between an electrical feature and an electrically conductive mechanical feature. In the context of instrument (500), such risks may occur with respect to wires (540) and/or push-pull cables (542). In addition, instrument (500) may include one or more sensors in shaft assembly (510) and/or end effector (550); and may also include one or more electrodes and/or other electrical features in end effector (550). Other components of instrument (500) that may present the above-described risks will be apparent to those skilled in the art in view of the teachings herein.

E. Example of Wiring to End Effector

Figure 9:
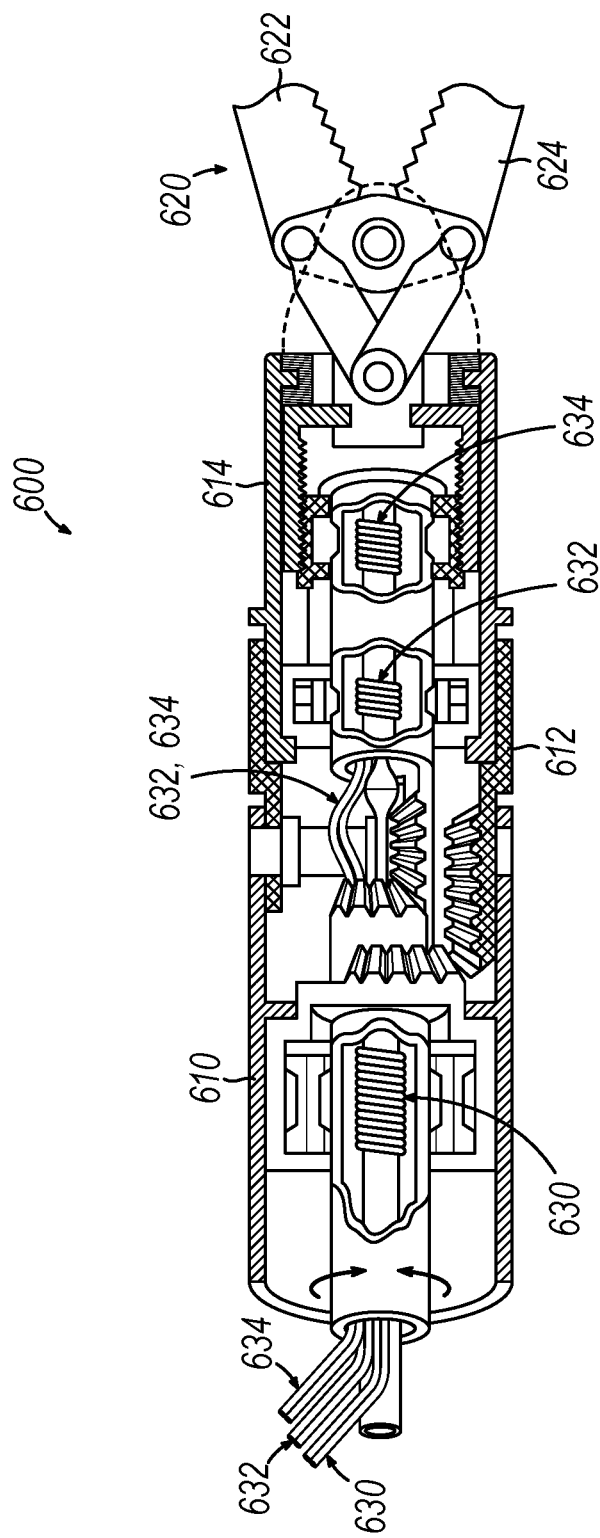
FIG. 9 depicts a side elevation view of a portion of a shaft assembly that may be incorporated into a surgical instrument, with housing components of the shaft being shown in cross-section to reveal internal components of the shaft.

FIG. 9 illustrates a portion of an instrument (600) that includes a shaft (610) with n first articulating segment (612) and a second articulating segment (614). In addition to the following teachings, instrument (600) may be constructed and operable in accordance with at least some of the teachings of U.S. Pub. No. 2017/0202605, entitled "Modular Battery Powered Handheld Surgical Instrument and Methods Therefor," published Jul. 20, 2017, issued as U.S. Pat. No. 10,842,523 on Nov. 24, 2020, the disclosure of which is incorporated by reference herein, in its entirety; and/or various other references cited herein. In the present example, end effector (620) is positioned at the distal end of second articulating segment (614). End effector (620) of this example includes a pair of jaws (622, 624) that are operable to pivot toward and away from each other to grasp tissue. In some versions, one or both of jaws (622, 624) includes one or more electrodes that is/are operable to apply RF energy to tissue as described herein. In addition, or in the alternative, end effector (620) may include an ultrasonic blade and/or various other features. Segments (612, 614) may be operable to pivot relative to shaft (610) and relative to each other to thereby deflect end effector (620) laterally away from or toward the central longitudinal axis of shaft (610).

Instrument (600) of this example further includes a first wire set (630) spanning through shaft (610), a second wire set (632) spanning through shaft (610) and both segments (612, 614), and a third wire set (634) spanning further through shaft (610) and both segments (612, 614). Wire sets (630, 632, 634) may be operable to control movement of segments (612, 614) relative to shaft (610). For instance, power may be communicated along one or more of wire sets (630, 632, 634) to selectively engage or disengage corresponding clutching mechanisms, to thereby allow lateral deflection of one or both of segments (612, 614) relative to shaft (610); and or rotation of one or both of segments (612, 614) relative to shaft (610). Alternatively, power may be communicated along one or more of wire sets (630, 632, 634) to drive corresponding solenoids, motors, or other features to actively drive lateral deflection of one or both of segments (612, 614) relative to shaft (610); and or rotation of one or both of segments (612, 614) relative to shaft (610). In versions where end effector (620) is operable to apply RF energy to tissue, one or more additional wires may extend along shaft (610) and segments (612, 614), in addition to wire sets (630, 632, 634).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/ or electrically conductive mechanical features that may provide a risk of generating electrical potentials between proximate components or creating capacitive couplings between electrical features and/or between an electrical feature and an electrically conductive mechanical feature. In the context of instrument (600), such risks may occur with respect to wire sets (630, 632, 634), the electrical components that wire sets (630, 632, 634) are coupled with, and/or other features that drive lateral deflection of one or both of segments (612, 614) relative to shaft (610). In addition, instrument (600) may include one or more sensors in shaft assembly (610) and/or end effector (620); and may also include one or more electrodes and/or other electrical features in end effector (620). Other components of instrument (600) that may present the above-described risks will be apparent to those skilled in the art in view of the teachings herein.

F. Example of Sensors in Shaft Assembly

Figure 10:
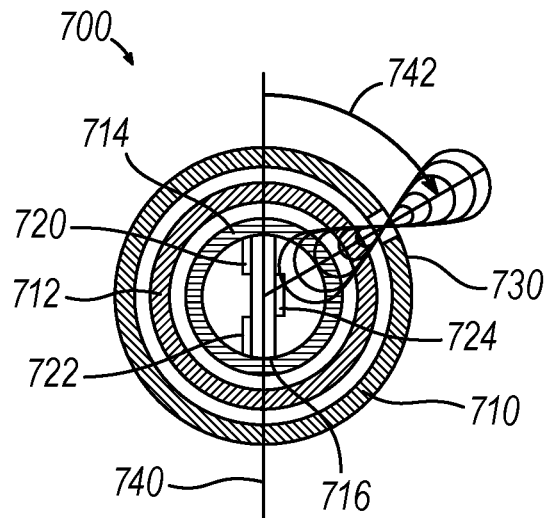
FIG. 10 depicts a cross-sectional end view of another shaft assembly that may be incorporated into a surgical instrument.

FIG. 10 shows an example of another shaft assembly (700) that may be incorporated into any of the various instruments (40, 50, 60, 100, 190, 200, 300, 350, 400, 500, 600) described herein. In addition to the following teachings, shaft assembly (700) may be constructed and operable in accordance with at least some of the teachings of U.S. Pub. No. 2017/0202608, issued as U.S. Pat. No. 10,835,307 on Nov. 17, 2022, the disclosure of which is incorporated by reference herein, in its entirety; and/or various other references cited herein. Shaft assembly (700) of this example includes an outer shaft (710), a first inner shaft (712), and a second inner shaft (714). A support member (716) spans diametrically across the interior of second inner shaft (714). By way of example only, support member (716) may comprise a circuit board, a flex-circuit, and/or various other electrical components. A plurality of sensors (720, 722, 724) are positioned on support member (716) in the present example. A magnet (730) is embedded in outer shaft (710) which is operable to rotate about inner shafts (712, 714).

In some versions, rotation of outer shaft (710) about inner shafts (712, 714) drives rotation of an end effector (not shown), located at the distal end of shaft assembly (700), about a longitudinal axis of shaft assembly (700). In some other versions, rotation of outer shaft (710) about inner shafts (712, 714) drives lateral deflection of the end effector away from or toward the longitudinal axis of shaft assembly (700). Alternatively, rotation of outer shaft (710) about inner shafts (712, 714) may provide any other results. In any case, sensors (720, 722, 724) may be configured to track the position of magnet (730) and thereby determine a rotational position (742) of outer shaft (710) relative to a fixed axis (740). Thus, sensors (720, 722, 724) may collectively serve as a position sensor like position sensor (112) of instrument (100).

Figure 11:
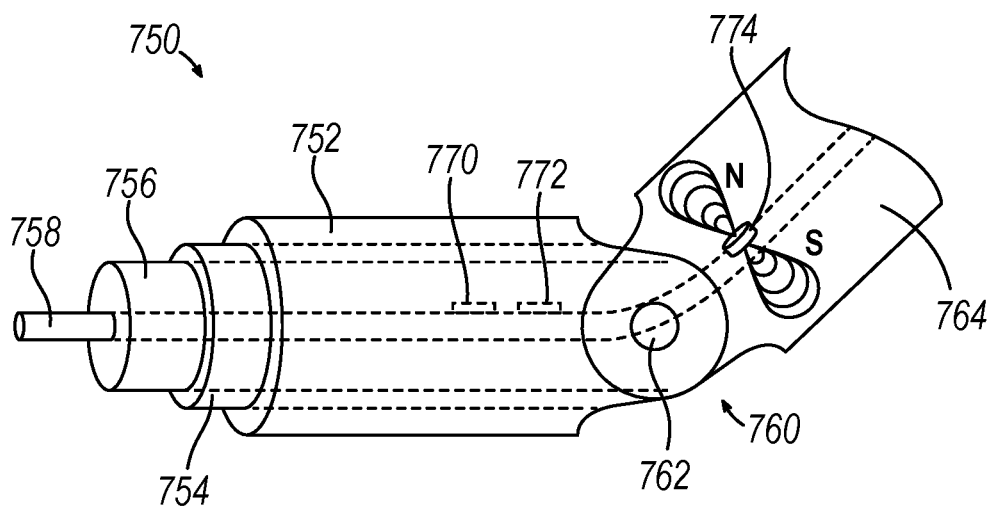
FIG. 11 depicts a schematic view of a portion of another shaft assembly that may be incorporated into a surgical instrument.

FIG. 11 shows an example of another shaft assembly (750) that may be incorporated into any of the various instruments (40, 50, 60, 100, 190, 200, 300, 350, 400, 500, 600) described herein. In addition to the following teachings, shaft assembly (750) may be constructed and operable in accordance with at least some of the teachings of U.S. Pub. No. 2017/0202608, issued as U.S. Pat. No. 10,835,307 on Nov. 17, 2022, the disclosure of which is incorporated by reference herein, in its entirety; and/or various other references cited herein. Shaft assembly (750) of this example includes a plurality of coaxially positioned proximal shaft segments (752, 754, 756) and a distal shaft segment (764). Distal shaft segment (764) is pivotably coupled with proximal shaft segment (752) via a pin (762) to form an articulation joint (760). An end effector (not shown) may be positioned distal to distal shaft segment (764), such that articulation joint (760) may be utilized to deflect the end effector laterally away from or toward a central longitudinal axis defined by proximal shaft segments (752, 754, 756). A flex circuit (758) spans along shaft segments (752, 754, 756, 764) and is operable to flex as shaft assembly (750) bends at articulation joint (760).

A pair of sensors (770, 772) are positioned along flex circuit (758) within the region that is proximal to articulation joint (760); while a magnet (774) is positioned on flex circuit (758) (or elsewhere within distal shaft segment (764)) in the region that is distal to articulation joint (760). Magnet (774) thus moves with distal shaft segment (764) as distal shaft segment (764) pivots relative to proximal shaft segments (752, 754, 756) at articulation joint (760); while sensors (770, 772) remain stationary during such pivoting. Sensors (770, 772) are configured to track the position of magnet (774) and thereby determine a pivotal position of distal shaft segment (764) relative to proximal shaft segments (752, 754, 756). In other words, sensors (770, 772) and magnet (774) cooperate to enable determination of the articulation bend angle formed by shaft assembly (750). Thus, sensors (770, 772) may collectively serve as a position sensor like position sensor (112) of instrument (100).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instruments (700, 750), such risks may occur with respect to sensors (720, 722, 724, 770, 772), the electrical components that sensors (720, 722, 724, 770, 772) are coupled with, and/or other features within the shaft assemblies of instruments (700, 750). Other components of instruments (700, 750) that may present the above-described risks will be apparent to those skilled in the art in view of the teachings herein.

G. Example of Drive Controls in Body and Shaft Assembly of Instrument

Figure 12:
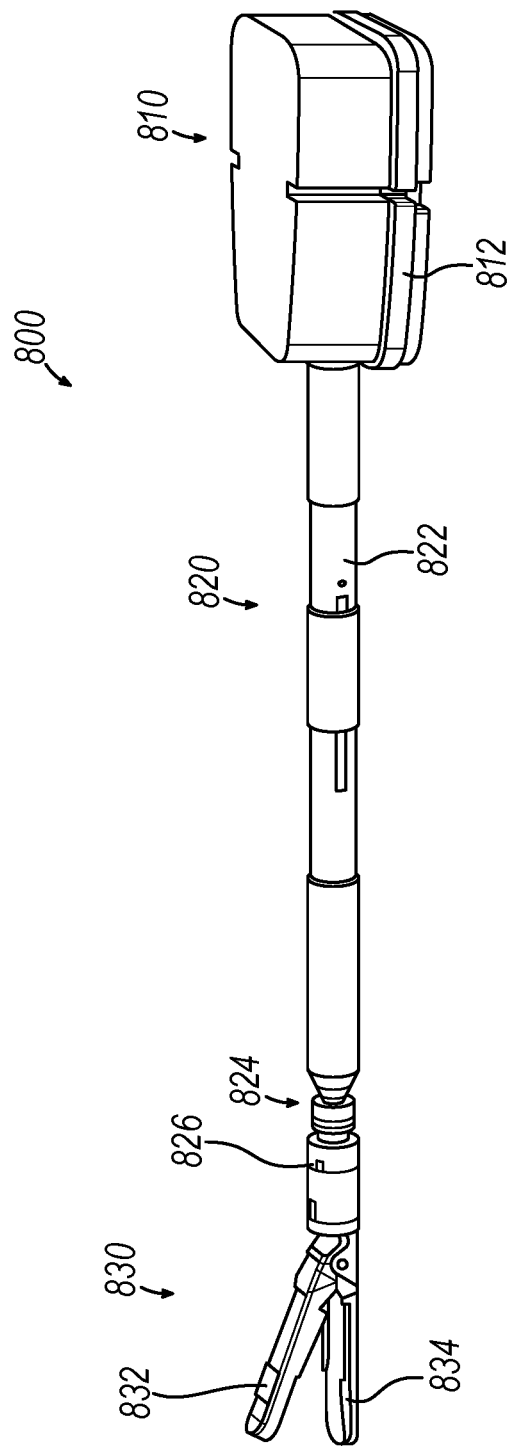
FIG. 12 depicts a perspective view of an example of a surgical instrument that may be incorporated into the robotic surgical system of FIG. 1.
Figure 13:
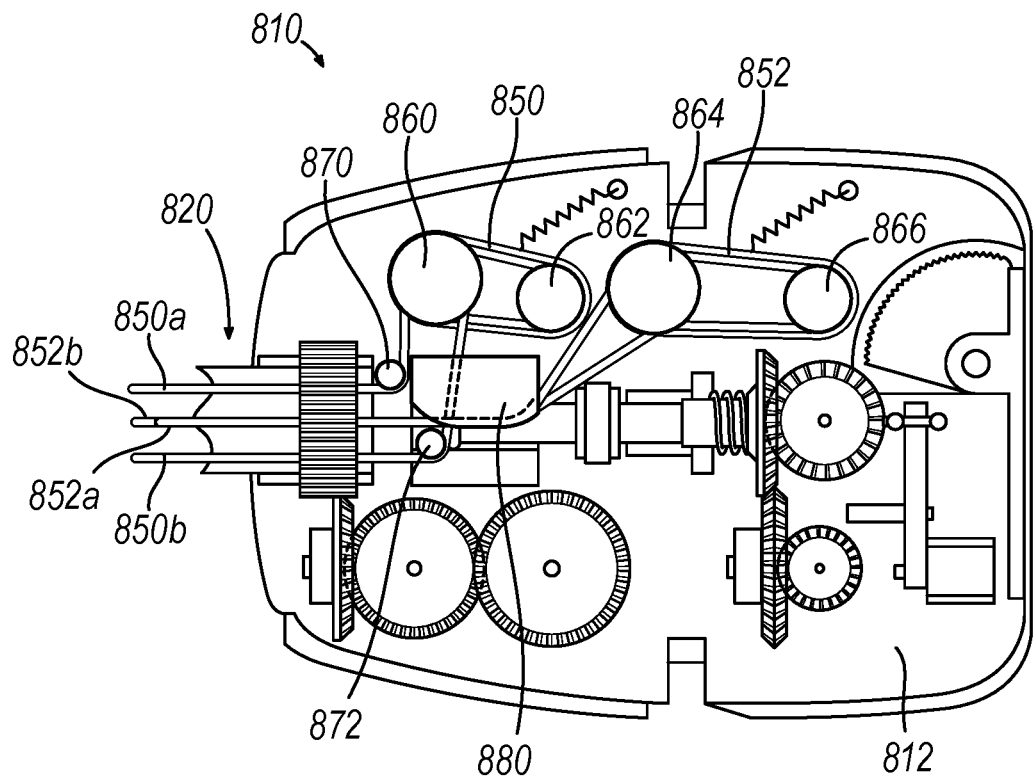
FIG. 13 depicts a top plan view of an interface drive assembly of the instrument of FIG. 12.
Figure 14:
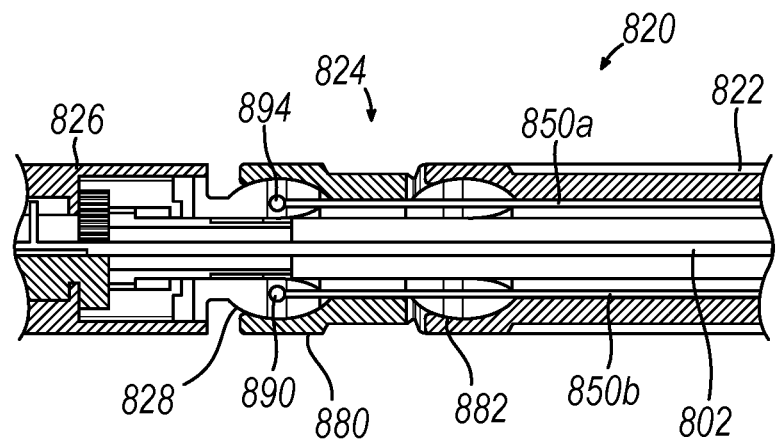
FIG. 14 depicts a cross-sectional side view of an articulation section of a shaft assembly of the instrument of FIG. 12.

FIGS. 12-14 show an example of an instrument (800) that may be incorporated into a robotic surgical system, such as the robotic surgical systems (10, 150) described herein. In addition to the following teachings, instrument (800) may be constructed and operable in accordance with at least some of the teachings of U.S. Pat. No. 9,125,662, the disclosure of which is incorporated by reference herein, in its entirety; and/or various other references cited herein. Instrument (800) of this example includes a body (810), a shaft assembly (820), and an end effector (830). Body (810) includes a base (812) that is configured to couple with a complementary component of a robotic arm (e.g., one of robotic arms (160, 170, 180)). Shaft assembly (820) includes a rigid proximal portion (822), an articulation section (824), and a distal portion (826). End effector (830) is secured to distal portion (826). Articulation section (824) is operable to deflect distal portion (826) and end effector (830) laterally away from and toward the central longitudinal axis defined by proximal portion (822). End effector (830) of this example includes a pair of jaws (832, 834). By way of example only, end effector (830) may be configured and operable like any of the various end effectors (46, 56, 66, 102, 230, 320, 350, 620) described herein.

As shown in FIGS. 13-14, a plurality of drive cables (850, 852) extend from body (810) to articulation section (824) to drive articulation of articulation section (824). Cable (850) is wrapped around a drive pulley (862) and a tensioner (860). Cable (850) further extends around a pair of guides (870, 872), such that cable (850) extends along shaft assembly (820) in two segments (850a, 850b). Cable (852) is wrapped around a drive pulley (866) and a tensioner (864). Cable (852) further extends around a guide (880), such that cable (852) extends along shaft assembly (820) in two segments (852a, 852b). In the present example, each drive pulley (862, 866) is configured to couple with a corresponding drive member (e.g., drive spindle, etc.) of the component of the robotic arm to which base (812) is secured. When drive pulley (862) is rotated, one segment (850a) of cable (850) will translate in a first longitudinal direction along shaft assembly (820); while the other segment (850b) will simultaneously translate in a second (opposite) direction along shaft assembly (820). Similarly, when drive pulley (866) is rotated, one segment (852a) of cable (852) will translate in a first longitudinal direction along shaft assembly (820); while the other segment (852b) will simultaneously translate in a second (opposite) direction along shaft assembly (820).

As shown in FIG. 14, articulation section (824) of the present example includes an intermediate shaft segment (880) that is longitudinally interposed between proximal portion (822) and distal portion (826). A ball feature (828) at the proximal end of distal portion (826) is seated in a socket at the distal end of intermediate shaft segment (880), such that distal portion (826) is operable to pivot relative to intermediate shaft segment (880) along one or more planes. Segments (850a, 850b) of drive cable (850) terminate in corresponding ball-ends (894, 890), which are secured to ball feature (828) of distal portion (822). Drive cable (850) is thus operable to drive pivotal movement of distal portion (826) relative to intermediate shaft segment (880) based on the direction in which drive pulley (862) rotates. A ball feature (882) at the proximal end of intermediate portion (880) is seated in a socket at the distal end of proximal portion (822), such that intermediate portion (880) is operable to pivot relative to proximal portion (822) along one or more planes. In some versions, this pivotal movement of intermediate portion (880) relative to proximal portion (822) is driven by cable (852). As also shown in FIG. 14, an electrical cable (802) passes through articulation section (824). Electrical cable (802) provides a path for electrical communication to end effector (830), thereby allowing for delivery of electrical power (e.g., RF energy) to one or more electrodes in end effector (830), providing a path for electrical signals from one or more sensors in end effector (830) to be communicated back to body (810), and/or other forms of electrical communication.

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (800), such risks may occur with respect to drive cables (850, 852), the components that (850, 852) are coupled with, electrical features within shaft assembly (820), and/or other features within instrument (800). Other components of instrument (800) that may present the above-described risks will be apparent to those skilled in the art in view of the teachings herein.

Figure 15:
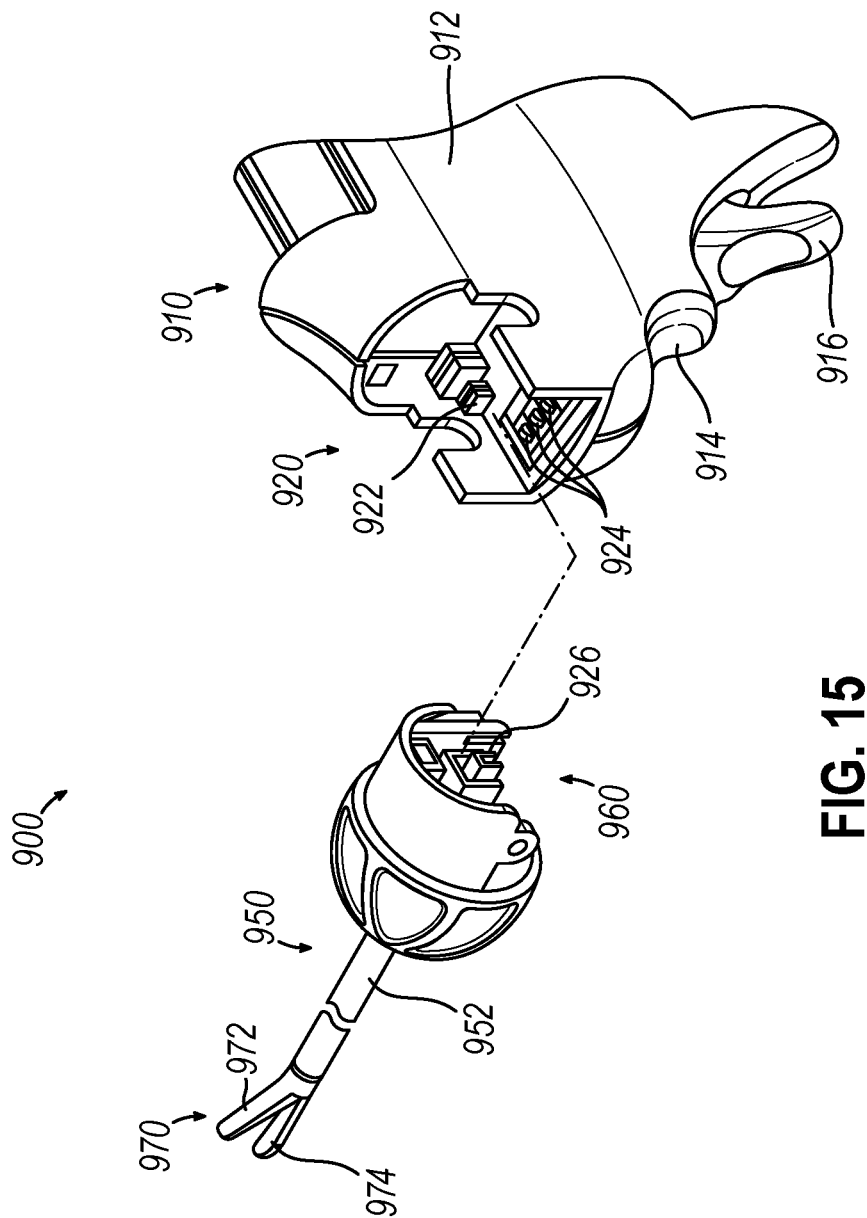
FIG. 15 depicts a perspective view of another example of a handheld surgical instrument, with a modular shaft assembly separated from a handle assembly.

H. Example of Electrical Features at Interface Between Modular Components of Instrument In some instances, it may be desirable to provide a surgical instrument that allows for modular coupling and decoupling of components. For instance, FIG. 15 shows an example of an instrument (900) that includes a handle assembly (910) and a modular shaft assembly (950). While instrument (900) of this example is handheld, similar features and modularity may be readily incorporated into a robotically controlled instrument. Handle assembly (910) of this example includes a body (912), an activation button (914), a pivoting trigger (916), and a shaft interface assembly (920). Shaft interface assembly (920) includes a mechanical drive feature (922) and an array of electrical contacts (924). Electrical contacts (924) may be in electrical communication with a control circuit, power source, and/or various other electrical features within handle assembly (910) as will be apparent to those skilled in the art in view of the teachings herein.

Shaft assembly (950) includes a shaft section (952) and an end effector (970), which includes a pair of jaws (972, 874). Shaft section (952) and end effector (970) may be configured and operable in accordance with any of the various shaft assemblies and end effectors described herein. Shaft assembly (950) of this example further includes a handle interface assembly (960). Handle interface assembly (960) includes a mechanical drive feature (962) and a plurality of electrical contacts (not shown). These electrical contacts of handle interface assembly (960) may be in electrical communication with one or more electrodes, sensors, and/or other electrical components within shaft section (952) and/or end effector (970) as will be apparent to those skilled in the art in view of the teachings herein.

When shaft assembly (950) is coupled with handle assembly (910), mechanical drive feature (922) of handle assembly (910) mechanically couples with mechanical drive feature (962) of shaft assembly (950), such that mechanical drive features (922, 962) may cooperate to communicate motion from a motive power source in handle assembly (910) (e.g., pivoting trigger (916), a motor, etc.) to one or more components within shaft section (952) and, in some versions, end effector (970). In some versions, mechanical drive features (922, 962) cooperate to communicate rotary motion from a motive power source in handle assembly (910) (e.g., pivoting trigger (916), a motor, etc.) to one or more components within shaft section (952) and, in some versions, end effector (970). In addition, or in the alternative, mechanical drive features (922, 962) may cooperate to communicate linear translational motion from a motive power source in handle assembly (910) (e.g., pivoting trigger (916), a motor, etc.) to one or more components within shaft section (952) and, in some versions, end effector (970).

When shaft assembly (950) is coupled with handle assembly (910), electrical contacts (924) of shaft interface assembly (920) also couple with complementary electrical contacts of handle interface assembly (960), such that these contacts establish continuity with each other and thereby enable the communication of electrical power, signals, etc. between handle assembly (910) and shaft assembly (950). In addition to or in lieu of having contacts (924), electrical continuity may be provided between handle assembly (910) and shaft assembly (950) via one or more electrical couplings at mechanical drive features (922, 962). Such electrical couplings may include slip couplings and/or various other kinds of couplings as will be apparent to those skilled in the art in view of the teachings herein.

In some scenarios where electrical power or electrical signals are communicated across mating contacts that provide electrical continuity between two components of an instrument (e.g., contacts (924) of shaft interface assembly (920) and complementary electrical contacts of handle interface assembly (960)), there may be a risk of short circuits forming between such contacts. This may be a particular risk when contacts that are supposed to be electrically isolated from each other are located in close proximity with each other, and the area in which these contacts are located may be exposed to fluids during use of the instrument. Such fluid may create electrical bridges between contacts and/or bleed signals that are being communicated between contacts that are supposed to be coupled with each other. It may therefore be desirable to provide features to prevent or otherwise address such occurrences at contacts of an instrument like instrument (900).

In some scenarios where electrical power or electrical signals are communicated across mechanical couplings between different components of an instrument (e.g., via slip couplings, etc.), such couplings might provide variable electrical resistance in a shaft assembly or other assembly of the instrument. For instance, motion at mechanical drive features (922, 962) may provide variable electrical resistance at an electrical slip coupling between mechanical drive features (922, 962); and this variable electrical resistance may impact the communication of electrical power or electrical signals across the slip coupling. This may in turn result in signal loss or power reductions. It may therefore be desirable to provide features to prevent or otherwise address such occurrences at electrical couplings that are found at mechanical couplings between two moving parts of an instrument like instrument (900).

IV. Exemplary Features for Monopolar Surgical Instrument Energy Paths

The following description relates to examples of different features that may be incorporated into any of the various monopolar RF electrosurgical instruments (40, 420) described above. While these examples are provided separate from each other, the features described in any of the following examples may be combined with the features described in other examples described below. Thus, the below-described features may be combined in various permutations as will be apparent to those skilled in the art in view of the teachings herein. Similarly, various ways in which the below-described features may be incorporated into any of the various instruments (40, 420) described above will be apparent to those skilled in the art in view of the teachings herein. It should be understood that the below-described features may be incorporated into robotically controlled monopolar RF surgical instruments and/or handheld monopolar RF surgical instruments.

FIG. 16 shows an example of a monopolar RF energy delivery system (1000) which is a modified version of RF energy delivery system (400) described above with reference to FIG. 16. RF energy delivery system (1000) of the present example includes a power generator (1010), a delivery instrument (1020), a first ground pad assembly (1040), and a second ground pad assembly (1042). In addition to the following teachings, instrument (1020) may be constructed and operable in accordance with at least some of the teachings of U.S. Pub. No. 2019/0201077, issued as U.S. Pat. No. 11,291,495 on Apr. 5, 2022, the disclosure of which is incorporated by reference herein, in its entirety; and/or various other references cited herein. Power generator (1010) is operable to deliver monopolar RF energy to instrument (1020) via a cable (1030), which is coupled with power generator (1010) via a port (1014). In some versions, port (1014) includes an integral sensor. By way of example only, such a sensor in port (1014) may be configured to monitor whether excess or inductive energy is radiating from power generator (1010). Instrument (1020) includes a body (1022), a shaft (1024), a sensor (1026), and a distal electrode (1028) that is configured to contact a patient (P) and thereby apply monopolar RF energy to the patient (P). By way of example only, sensor (1026) may be configured to monitor whether excess or inductive energy is radiating from instrument (1020). Based on signals from sensor (1026), a control module in power generator (1010) may passively throttle the ground return from ground pad assembly (1040) based on data from sensor (1026).

As shown, a dual ground pad configuration can be utilized, comprising two or more resistive continuity ground pad assemblies (1040, 1042) that provide direct contact between the skin of the patient (P) and one or more metallic components of ground pad assembly (1040, 1042). In some other versions, one or both of ground pad assemblies (1040, 1042) comprise a capacitive coupling ground pad that includes a gel material that is interposed between the patient (P) and the ground return plate. In the present example, ground pad assemblies (1040, 1042) are positioned under the patient (P) and are coupled to power generator (1010) via cables (1032, 1036) via ports (1016, 1034, 1018, 1038), respectively. Either or all of ports (1016, 1034, 1018, 1038) may include an integral sensor configured to monitor one or more therapeutic signals and/or diagnostic signals as described below.

In some versions of monopolar RF energy delivery system (1000), sensors in either or all of ports (1016, 1034, 1018, 1038) may be configured to monitor whether excess or inductive energy is radiating from one or both ground pad assemblies (1040, 1042) during operation. That is because patient injury may occur during operation if, for example, one or both ground pad assemblies (1040, 1042) are inadequately positioned or secured to patient (P), due to operator error. Injuries such as severe burns may occur to patient (P) in this instance as therapeutic monopolar RF energy may become too concentrated in one area on the skin of patient (P). More particularly, ground pad assemblies (1040, 1042) offer the path of least resistance from patient (P) back to generator (1010) and ensure an area of low energy current density. If one or both of the return ground pad assemblies (1040, 1042) is not completely in contact with the patient's skin, or is otherwise not able to disperse the electrical current safely, then the exiting current may have a high enough density to produce an unintended burn. It is therefore important to have good contact between patient (P) and ground pad assemblies (1040, 1042). Otherwise, when ground pad assemblies (1040, 1042) are compromised in the quantity or quality of the pad or patient interfaces, the electrical circuit may be completed by some small grounded contact points such as electrocardiogram leads, towel clips, intravenous stands, or other surgical equipment, and may produce high current densities, causing a burn to patient (P).

As described herein, a "therapeutic signal" is an RF energy signal that is applied to tissue via electrode (1028) and provides a desired therapeutic effect on tissue. Examples of desired therapeutic effects may include sealing of tissue, electrocautery, ablation, or other tissue effects. As also described herein, a "diagnostic signal" is an RF energy signal that is transmitted to confirm whether ground pad assemblies (1040, 1042) are appropriately coupled with the patient (P). Thus, diagnostic signals are intended diagnose a state of monopolar RF energy delivery system (1000); and are not intended to produce effects on tissue. In the present example, generator (1010) is configured to generate therapeutic signals and diagnostic signals in accordance with the teachings below.

In some versions, monopolar RF energy delivery system (1000) may be configured to generate and transmit a diagnostic signal through one or both ground pad assemblies (1040, 1042) via cables (1032, 1036), respectively, to monitor for ground pad assembly (1040, 1042) placement errors. RF energy delivery system (1000) may be further configured to terminate the operation (e.g., by automatically causing generator (1010) to disconnect power from instrument (1020) or otherwise cease delivery of therapeutic signals to instrument (1020)), if the diagnostic signals are returning out of a particular range. In this example, generator (1010) is configured to output signals through three separate ports (1014, 1016, 1018). Specifically, generator (1010) may output a therapeutic signal, such as a signal having a frequency ranging from approximately 300 kHz to 500 kHz that is configured to affect tissue, through port (1014) to drive electrode (1028) of instrument (1020). Generator (1010) may also output, simultaneously with the therapeutic signal or otherwise, a diagnostic signal through one of ports (1016 or 1018) to the one connected ground pad assembly (1040 or 1042) electrically connected to the selected port (1016 or 1018), and receive that signal via a signal return path defined by the other port (1016 or 1018) and connected ground pad assembly (1040 or 1042). Diagnostic signals may be lower frequency signals that are configured to not affect tissue. For example, a diagnostic signal may be transmitted in a range from approximately 15 kHz to approximately 50 kHz. In some examples, a diagnostic signal may be transmitted at or around 30 kHz. Generator (1010) may be configured to alternate generating and transmitting diagnostic signals through each port (1016, 1018) and receiving the diagnostic signal return through the other port (1016, 1018). Return signals may thus be monitored for excessive energy losses or spikes outside of a predetermined signal range that would indicate an issue has arisen with a connection of one or both ground pad assemblies (1040, 1042) during operation.

In some surgical operations, one or more components of instrument (1020), such as components positioned within or coupled with shaft (1024), may be comprised of metallic materials and may therefore generate significant unwanted capacitive coupling potentials and currents along those components. As noted above, capacitive coupling may provide undesirable results such as power reductions, signal reductions, signal interference, patient injuries, and/or other undesirable results. It may therefore be desirable to provide features to prevent or otherwise address the capacitive coupling currents. In some versions, an instrument shield (1044) may be included on or within instrument (1020) to collect the capacitive coupling energy and thereby shield the metallic components from the unwanted currents and prevent the currents from traveling throughout system (1000). Shield (1044) may be configured to couple with or envelop around the metallic components to collect and divert capacitive coupling currents back to generator (1010) by a conductor wire (1046), which further couples with a return cable of a ground pad assembly, such as cable (1032) of ground pad assembly (1040). Instead of flowing through the metallic components toward other grounded components of system (1000), the capacitively coupled current flows back to generator (1010) through shield (1044), wire (1046), and cable (1032) and so the unwanted currents do not interfere with the therapeutic signals or cause injuries to patient (P). This may also allow for generator (1010) to more effectively monitor its therapeutic signal output through port (1014).

However, as noted above, some systems (1000) may be configured to closely monitor energy flowing to generator (1010) through return path cables (1032, 1036) for excessive energy spikes or losses that may indicate problems in the operation of system (1000). By diverting capacitive coupling currents from instrument (10202) through at least one return cable (1032, 1036) of one ground pad assembly (1040, 1042), generator (1010) may detect significant energy imbalances between return cables (1032, 1036); and generator (1010) may disconnect power to instrument (1020) (e.g., cease delivery of therapeutic signals) as result. For instance, in the configuration shown in FIG. 16, approximately 75% of the total energy output from generator (1010) may be returned through only one of cables (1032, 1036). It may therefore be desirable to provide features to balance the return signals more evenly between return cables (1032, 1036). Examples of such features are described in greater detail below.

A. Exemplary Monopolar Surgical Instrument Energy Path Using a Filter

Figure 17:
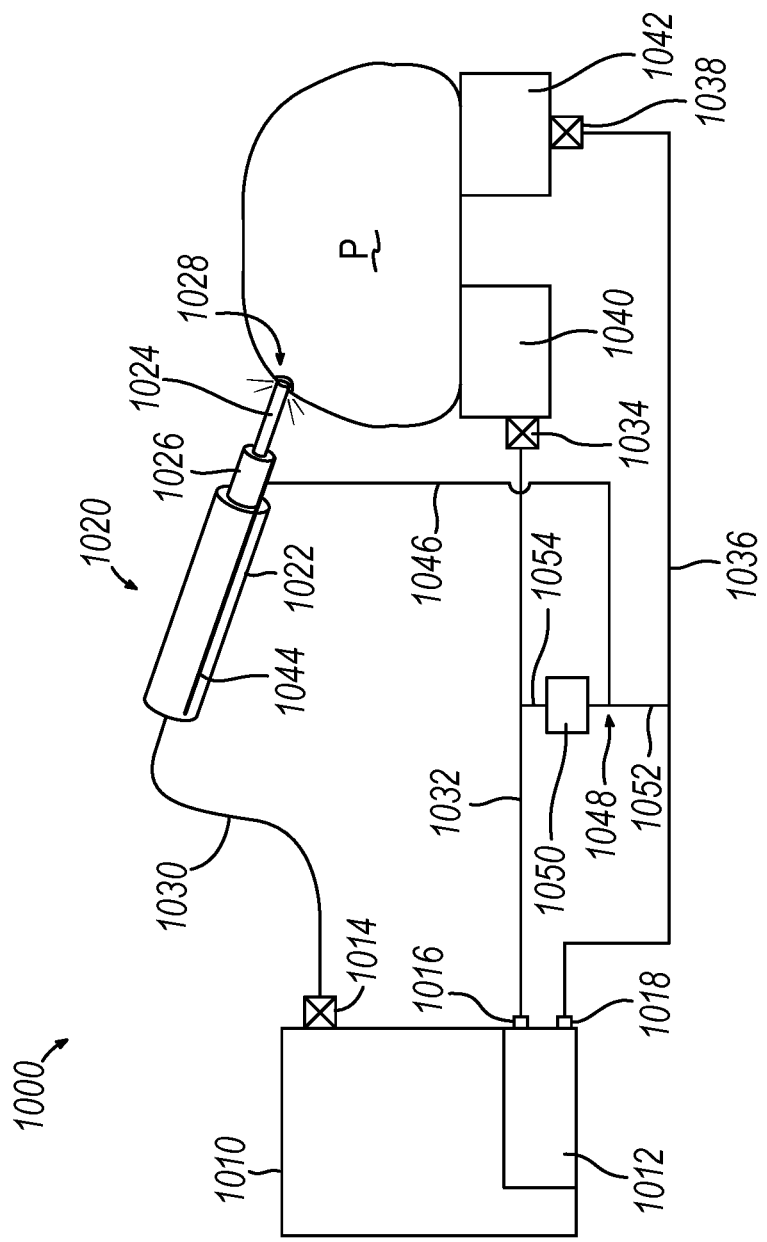
FIG. 17 depicts a schematic view of the surgical instrument of FIG. 16, showing a first alternative configuration of an exemplary return path.

FIG. 17 shows monopolar RF energy delivery system (1000) in one exemplary configuration for balancing the electrical current returned to generator (1010) between return path cables (1032, 1036) of ground pad assemblies (1040, 1042). Particularly, wire (1046) is configured to electrically couple with a "T" junction (1048), and "T" junction (1048) is further electrically coupled with each return path cable (1032, 1036) via a pair of leads (1052, 1054). Because each cable (1032, 1036) offers a relatively similar path of resistance back to generator (1010) from shield (1044) and through "T" junction (1048) in this example, energy diverted from shield (1044) through cables (1032, 1036) may split relatively evenly (i.e., in substantially equal portions) among cables (1032, 1036). In some instances, the portion of the electrical current diverted to cable (1032) may be up to approximately 30% of the portion of the electrical current diverted to cable (1036). Generator (1010) may more effectively monitor the balanced combination of therapeutic (e.g., 300-500 kHz) and diagnostic (e.g., 30 kHz) return signals flowing through cables (1032, 1036) and therefore avoid misinterpreting imbalanced signals as indicating the occurrence of problems within system (1000) or with the positioning of either ground pad assembly (1040, 1042).

However, as noted above, generator (1010) may be configured to generate and transmit lower frequency diagnostic signals in alternating fashion through ground pad assemblies (1040, 1042) via ports (1016, 1018). By including "T" junction (1048), an electrical short circuit is introduced between cables (1032, 1036). To prevent the short circuit from rendering the diagnostic signal procedures inoperable, a signal filter (1050) may be electrically coupled on either lead (1050, 1052) to thereby prohibit diagnostic signals from passing through leads (1050, 1052), while allowing therapeutic signals to pass through leads (1050, 1052). More particularly, filter (1050) may be configured as a high-pass filter to block a lower range of signals from passing through leads (1050, 1052) and may be configured to allow a higher range of signals to pass through leads (1050, 1052). Thus, in configurations where diagnostic signals are transmitted at or around 30 kHz, filter (1050) may be configured as either an active or passive high pass filter with a cutoff frequency at or near 45 kHz, for example. However, it should be understood that, while certain signal ranges and one particular cutoff frequency example are described herein, various other signal ranges and cutoff frequencies may be configured as required.

B. Exemplary Monopolar Surgical Instrument Energy Path Using a Transformer

Figure 18:
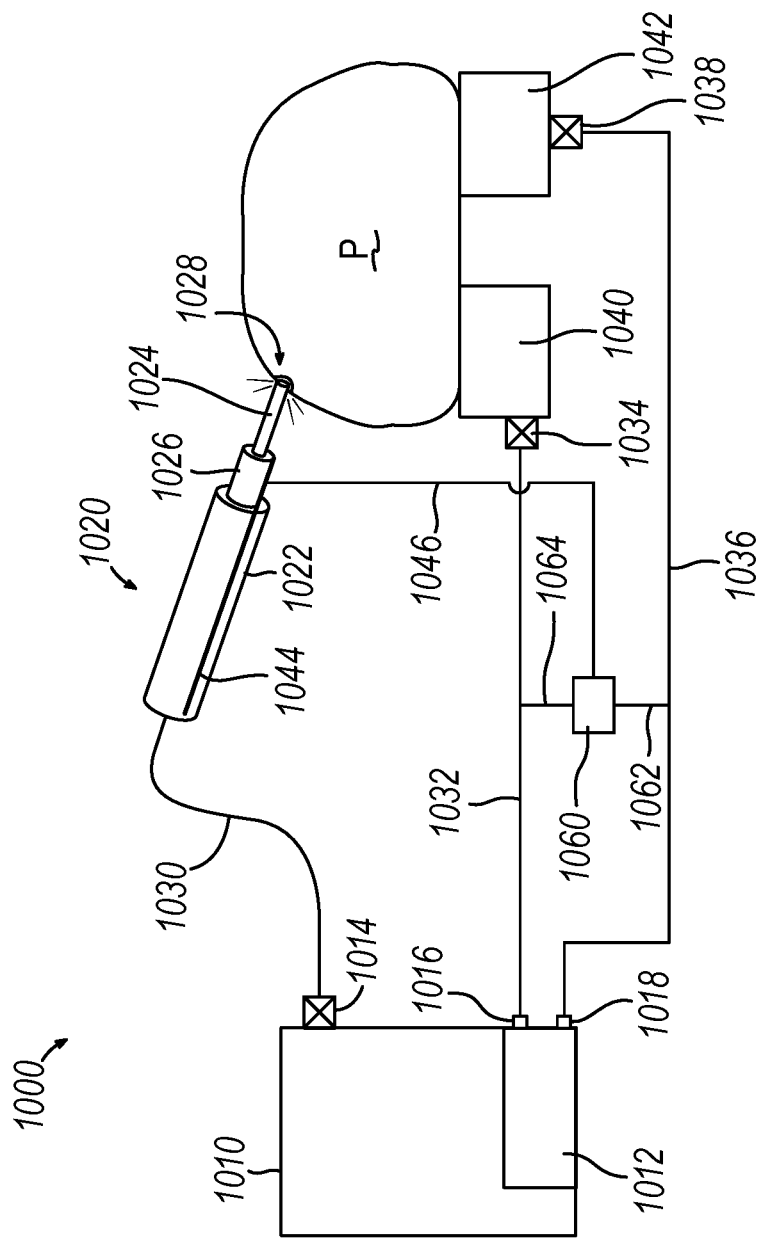
FIG. 18 depicts a schematic view of the surgical instrument of FIG. 16, showing a second alternative configuration of an exemplary return path.

FIG. 18 shows monopolar RF energy delivery system (1000) in another exemplary configuration for balancing the electrical current returned to generator (1010) between return path cables (1032, 1036) of ground pad assemblies (1040, 1042). Particularly, wire (1046) is configured to electrically couple with a transformer (1060), such as to the primary winding of transformer (1060); and dual secondary windings of transformer (1060) are further electrically coupled with each return path cable (1032, 1036) via a pair of leads (1062, 1064). Thus, because each cable (1032, 1036) offers a relatively similar path of resistance back to generator (1010) from shield (1044) and through transformer (1060), energy diverted from shield (1044) through cables (1032, 1036) may split relatively evenly among cables (1032, 1036). Transformer (1060) may be, for example, a current load balancing transformer.

While various alternative systems and methods are described herein for balancing the energy of wire (1046) onto cables (1032, 1036), it should be understood that various alternative configurations have also been contemplated as would be known and understood by those skilled in the art in view of the teachings herein.

V. Example of Electrosurgical Instrument System with Parasitic Energy Loss Monitor The following description relates to examples of different features that may be incorporated into any of the various RF electrosurgical instruments (40, 50, 420) described above. While these examples are provided separate from each other, the features described in any of the following examples may be combined with the features described in other examples described herein. Thus, the below-described features may be combined in various permutations as will be apparent to those skilled in the art in view of the teachings herein. Similarly, various ways in which the below-described features may be incorporated into any of the various instruments (40, 50, 420) described above will be apparent to those skilled in the art in view of the teachings herein. It should be understood that the below-described features may be incorporated into robotically controlled surgical instruments and/or handheld surgical instruments, including but not limited to such instruments that are powered via on-board battery and/or powered via wire to an external power source. This includes, but is not limited to, the various kinds of robotically controlled instruments described above, the various kinds of handheld instruments described above, the various kinds of battery-powered instruments described above, and the various kinds of instruments described above that are powered via wire to an external power source.

As noted above, some aspects of the present disclosure are presented for a surgical instrument with improved device capabilities for reducing undesired operational side effects. Examples of such devices and related concepts are disclosed in U.S. Pat. Pub. No. 2019/0201077, entitled "Interruption of Energy Due to Inadvertent Capacitive Coupling," published Jul. 4, 2019, issued as U.S. Pat. No. 11,291,495 on Apr. 5, 2022, the disclosure of which is incorporated by reference herein. In particular, the surgical instrument may include means for limiting capacitive coupling to improve monopolar RF isolation for use independently or in cooperation with another advanced energy modality. Capacitive coupling occurs generally when there is a transfer of energy between nodes, induced by an electric field. During surgery, capacitive coupling may occur when two or more electrical surgical instruments are being used in or around a patient. Capacitive coupling may also occur within a single instrument or single instrument system. For instance, capacitive coupling may occur between electrically conductive components that are in close proximity with each other in the same instrument, including such components as described above with reference to FIGS. 1-15. While in some cases capacitive coupling may be desirable, as additional devices may be powered inductively by capacitive coupling, having capacitive coupling occur accidentally during surgery or around a patient generally can have extremely deleterious consequences.

Parasitic or accidental capacitive coupling may occur in unknown or unpredictable locations, causing energy to be applied to unintended areas. When the patient is under anesthesia and unable to provide any response, parasitic capacitive coupling may cause undesired thermal damage to a patient before the operator realizes that any thermal damage is occurring. In addition, or in the alternative, parasitic capacitive coupling may result in undesirable electrical power losses. Such undesirable electrical power losses due to parasitic capacitive coupling may result in undesirably low delivery of electrical energy (e.g., monopolar RF energy) to tissue in the patient, which may produce an undesirable surgical result. In addition, or in the alternative, undesirable electrical power losses due to parasitic capacitive coupling may result in compromised feedback signals from sensors or other electrical components, where such adversely affected electrical signals result in unreliable feedback data. It is therefore desirable to prevent or at least limit parasitic or accidental capacitive coupling in surgical instruments and during surgery generally.

In some versions of the instruments described above, the electrosurgical system includes a surgical instrument and console, such as console (20) (see, FIG. 1). The console may include data processors, memory, and other computer equipment, along with one or more generators. Each generator may be configured to modulate the transmission of energy from the generator to the particular surgical instrument that the generator is powering if capacitive coupling has been detected along any of the components coupled with that surgical instrument. One or more safety fuses, sensors, controls, and/or algorithms may be in place to automatically trigger a modulation of the energy delivered by the generator in these scenarios. Alerts, including audio signals, vibrations, and visual messages may issue to inform the surgery team that the energy has been modulated, or is being modulated, due to the detection of capacitive coupling.

In some aspects, the system includes means for detecting that a capacitive coupling event has occurred. For example, an algorithm that includes inputs from one or more sensors for monitoring events around the system may apply situational awareness and other programmatic means to conclude that capacitive coupling is occurring somewhere within the system and react accordingly. A system having situational awareness means that the system may be configured to anticipate scenarios that may arise based on present environmental and system data and determining that the present conditions follow a pattern that gives rise to predictable next steps. As an example, the system may apply situational awareness in the context of handling capacitive coupling events by recalling instances in similarly situated surgeries where various sensor data is detected. The sensor data may indicate an increase in current at two particular locations along a closed loop electrosurgical system, that based on previous data of similarly situated surgeries, indicates a high likelihood that a capacitive coupling event is imminent.

In some aspects, the surgical instruments may be modified in structure to limit the occurrence of capacitive coupling, or in other cases reduce the collateral damage caused by capacitive coupling. For example, additional insulation placed strategically in or around the surgical instrument may help limit the incidence of capacitive coupling. In other cases, the end effector of the surgical instrument may include modified structures that reduce the incidence of current displacement, such as rounding the tips of the end effector or specifically shaping the blade of the end effector to behave more like a monopolar blade while still acting as a bipolar device.

In some aspects, the system may include passive means for mitigating or limiting the effects of the capacitive coupling. For example, the system may include leads that can shunt the energy to a neutral node through conductive passive components. In general, any and all of these aspects may be combined or included in a single system to address the challenges posed by multiple electrical components liable to cause capacitive coupling during patient surgery.

Figure 19:
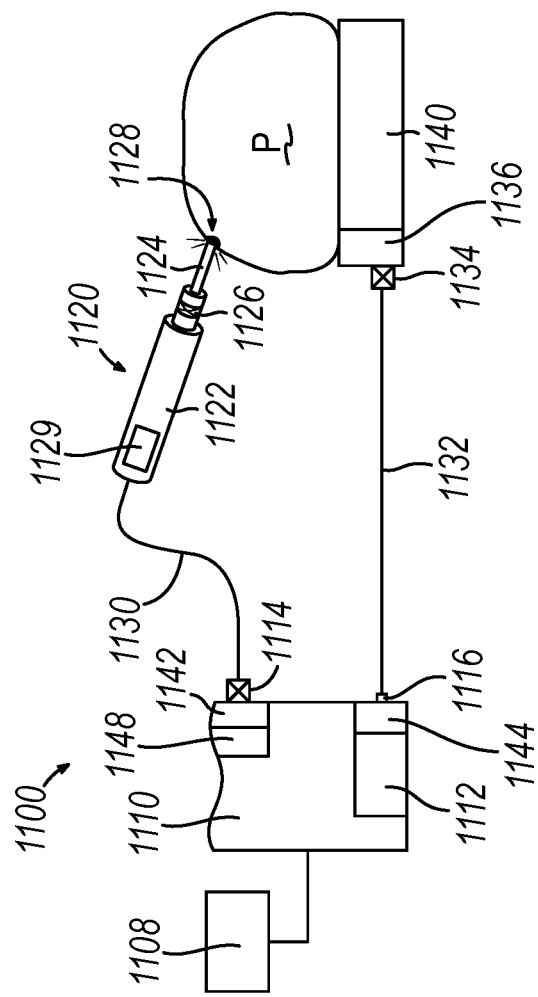
FIG. 19 depicts a schematic view of another example of a surgical instrument that is operable to apply monopolar RF energy to tissue.

In scenarios where there are multiple electrical sources near patient (P) and/or multiple electrically conductive components within an instrument in close proximity to electrical power-carrying components in the same instrument, parasitic capacitive coupling may present risks to a during surgery. Because patient (P) is not expected to express any reaction during surgery, if unknown or unpredicted capacitive coupling occurs, patient (P) may experience burns in unintended places as a result. In general, energy anomalies like capacitive coupling should be minimized or otherwise corrected in order to improve patient safety and/or otherwise provide desired surgical results. To monitor the occurrence of capacitive coupling or other types of energy anomalies, multiple smart sensors may be integrated into an electrosurgical system as indicators to determine whether excess or inductive energy is radiating outside the one or more of the electrical sources. An example of a system (1100) that incorporates such smart sensors is shown in FIG. 19. System (1100) of FIG. 19 is substantially similar to system (400) of FIG. 7, described above, but with variations described below.

System (1100) of FIG. 19 is operable to detect capacitive couplings that inadvertently occur within or between components of system (1100), in accordance with at least one aspect of the present disclosure. System (1100) of this example includes a power generator (1110), a delivery instrument (1120), and a ground pad assembly (1140). Instrument (1120) of system (1100) may include means for applying RF or ultrasonic energy to a distal electrode (1128), and in some cases may include a blade and/or a pair of jaws to grasp or clamp onto tissue. In addition to the following teachings, instrument (1120) may be constructed and operable in accordance with at least some of the teachings of U.S. Pub. No. 2019/0201077, issued as U.S. Pat. No. 11,291,495 on Apr. 5, 2022, the disclosure of which is incorporated by reference herein, in its entirety; and/or various other references cited herein.

Power generator (1110) may be operable to deliver monopolar RF energy to instrument (1120) via a cable (1130), which is coupled with power generator (1110) via a port (1114). The energy powered by the generator (1110) may touch the patient (P) through distal electrode (1128) of instrument (1120). In the present example, port (1114) includes an integral sensor (1142) and a tuner (1148). By way of example only, sensor (1142) in port (1114) may be configured to monitor whether excess or inductive energy is radiating from power generator (1110) and/or whether parasitic losses are occurring in energy being delivered by power generator (1110). Tuner (1148) may be configured to modulate the delivery of energy by power generator (1110) via port (1114), based at least in part on feedback from sensor (1142). Examples of how such modulation may be carried out will be described in greater detail below.

Instrument (1120) includes a body (1122), a shaft (1124), a sensor (1126), and a distal electrode (1128) that is configured to contact a patient (P) and thereby apply monopolar RF energy to the patient (P). By way of example only, sensor (1126) may be configured to monitor whether excess or inductive energy is radiating from instrument (1120) and/or whether parasitic losses are occurring in signals from instrument (1120). Based on feedback signals from sensor (1126), a control module in power generator (1110) may passively throttle or otherwise adjust the ground return from ground pad assembly (1140). In addition, or in the alternative, the ground return from ground pad assembly (1140) may me throttled or otherwise adjusted based at least in part on feedback from sensor (1142) and/or other sources.

Ground pad assembly (1140) is configured to provide an electrical ground to the patient (P) when surgical instrument (1120) touches patient (P) and applies electrosurgical energy to the patient (P). In this role, ground pad assembly (1140) may further divert excess energy (e.g., undesirable excess electrosurgical energy) that is undesirably delivered to the patient (P). In some versions, ground pad assembly (1140) comprises one or more resistive continuity ground pads that provide direct contact between the skin of the patient (P) and one or more metallic components of the ground pad. In some other versions, ground pad assembly (1140) comprises a capacitive coupling ground pad that includes a gel material that is interposed between the patient (P) and the ground return plate. By way of example only, ground pad assembly (1140) may be configured and operable similar to a Smart MEGADYNE™ MEGA SOFT™ pad by Ethicon US, LLC. In the present example, ground pad assembly (1140) is positioned under the patient (P) and is coupled to a neutral electrode (1112) of power generator (1110) via a cable (1132). Cable (1132) is coupled via ports (1116, 1134). Either or both of ports (1116, 1134) may include an integral sensor (1144, 1146). By way of example only, such a sensor (1144, 1146) in either or both of ports (1116, 1134) may be configured to monitor whether excess or inductive energy is radiating from ground pad assembly (1140). Based on feedback signals from one or both of sensors (1144, 1146), a control module in power generator (1110) may passively throttle or otherwise adjust the ground return from ground pad assembly (1140).

Figure 16:
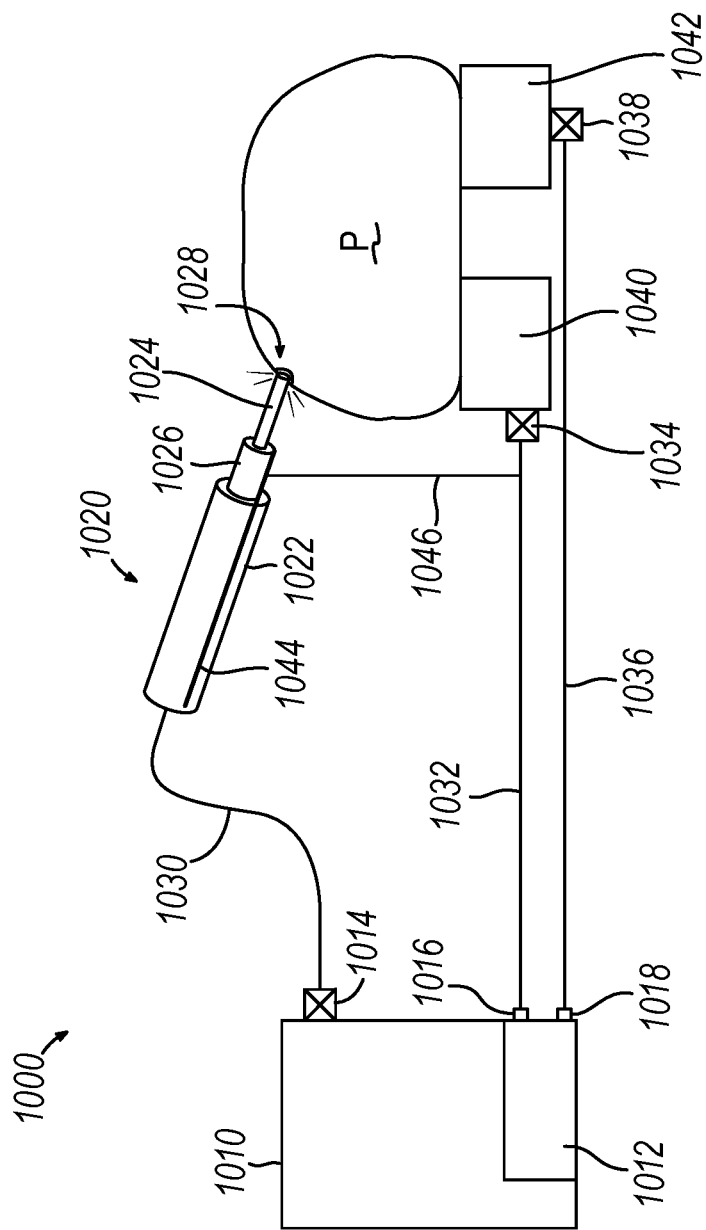
FIG. 16 depicts a schematic view of an example of a surgical instrument that is operable to apply monopolar RF energy to tissue and provide a return path for irregular electrical energy.

As shown in FIG. 16, sensors (1126, 1142, 1144, 1146) of the present example are placed at locations where energy may inductively radiate. One or more of sensors (1126, 1142, 1144, 1146) may be configured to detect capacitance; and if placed at strategic locations within system (1100), a reading of capacitance may imply that capacitive leakage is occurring near the sensor (1126, 1142, 1144, 1146). With knowledge of other sensors nearby or throughout the system not indicating a reading of capacitance, one may conclude that capacitive leakage is occurring in close proximity to whichever sensor (1126, 1142, 1144, 1146) is providing a positive indication. Other sensors may be used, such as capacitive leakage monitors or detectors. These sensors may be configured to provide an alert, such as lighting up or delivering a noise or transmitting a signal ultimately to a display monitor. In addition, generator (1110) may be configured to automatically modulate the energy being delivered via port (1114) to stop any further capacitive coupling from occurring.

In some aspects, generator (1110) may be configured to employ situational awareness that can help anticipate when capacitive coupling may occur during surgery. Generator (1110) may utilize a capacitive coupling algorithm to monitor the incidence of energy flowing through system (1100), and based on previous data about the state of energy in the system for a similar situated procedure, may conclude there is a likelihood that capacitive coupling may occur if no additional action is taken. For example, during a surgery involving prescribed methods for how to operate instrument (1120) and how much power should be employed during particular steps in the surgery, generator (1110) may draw from previous surgeries of the same and note that capacitive coupling has a stronger likelihood to occur after a particular step in the surgery. While monitoring the steps in the surgery, when the same or very similar energy profiles occur during or just before the expected step that tends to induce capacitive coupling, generator (1110) may deliver an alert that indicates this is likely to cause capacitive coupling. The operator may be given the option to reduce peak voltage in surgical instrument (1120), interrupt the power generation by generator (1110), or otherwise modulate the delivery of power from generator (1110) to instrument (1120). This may lead to eliminating the possibility of capacitive coupling before it has a chance to occur, or at least may limit any unintended effects caused by a momentary occurrence of capacitive coupling.

In some aspects, surgical instrument (1120) may include structural means for reducing or preventing capacitive coupling. For example, insulation in shaft (1124) of surgical instrument (1120) may reduce the incidence of inductance. In other cases, wire (1130) connecting generator (1110) to instrument (1120) or components on or within body (1122) may be shielded and coupled with a ground source, such as back through cable (1130) or by coupling with return path cable (1132) (not shown). Sensor (1142) may be further configured to sense the current returning to generator (1110) or other ground source through cable (1130) in addition to sensing the power output to electrode (1128). As another example, interrupting plastic elements within shaft (1124) may be intermittently present to prevent capacitive coupling from transmitting long distance within the shaft. Other insulator-type elements may be used to achieve similar effects.

As described above, some existing instruments may be configured to interrupt the power generation by the generator upon detecting capacitive coupling at one or more sensors. While such power interruptions may be effective in preventing the occurrence of undesirable results that might otherwise occur due to inadvertent capacitive coupling, such power interruptions may be disfavored by an operator of instrument (1120), particularly when the power interruption occurs suddenly during the middle of a surgical procedure. Power interruptions during a surgical procedure may frustrate the operator and increase the duration of surgery. It may therefore be more desirable to modulate the power delivered from a generator (1110) to an instrument (1120), without interrupting the power, to prevent the occurrence of undesirable results that might otherwise occur due to inadvertent capacitive coupling. Such power modulation may be provided on an ad hoc basis in response to real time feedback from sensors as described herein. While the exemplary methods will be described below with continued reference to system (1100), it should be understood that the methods described herein may be incorporated into other electrosurgical systems which may include sensors for monitoring capacitive leakage, including systems that provide modes of power delivery that are not necessarily limited to monopolar RF power delivery.

Figure 20:
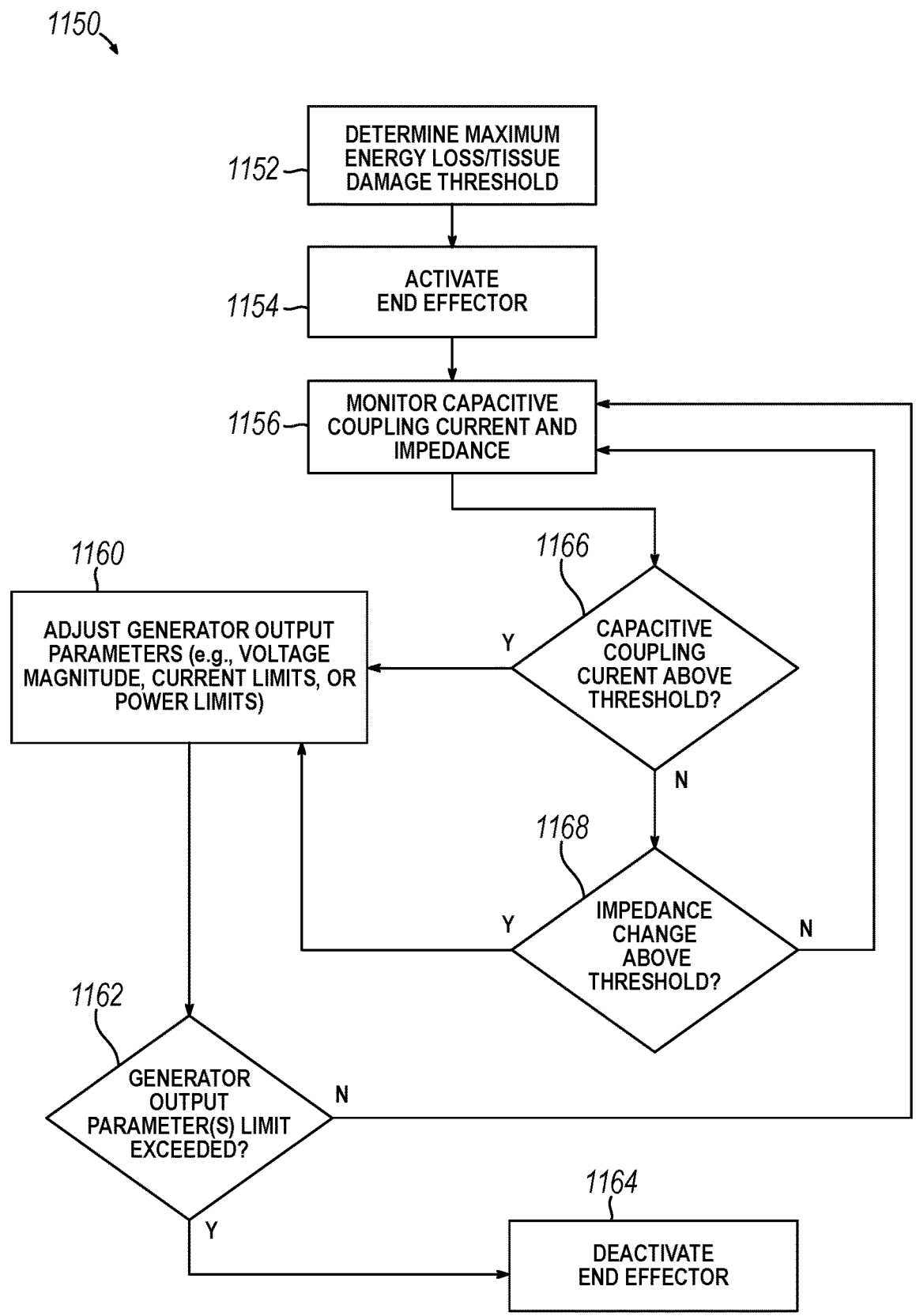
FIG. 20 depicts a flowchart of an exemplary method of monitoring the energy loss of a surgical instrument that is operable to apply RF energy to tissue.

FIG. 20 depicts a flowchart of an exemplary method of monitoring the energy loss of a surgical instrument that is operable to apply RF energy to tissue, such as any one of instruments (40, 50, 420, 1120) described herein. By employing the exemplary methods, such as within system (1100), one or more of sensors (1126, 1142, 1144, 1146) (see FIG. 19) are configured to monitor the capacitive coupling currents and instrument impedance and to provide feedback to generator (1110) (or, alternatively, to a data processor of console (20) that is controlling generator (1110)). Generator (1110), or a local or cloud-based processing device coupled with generator (1110) for example, is then able to determine whether generator (1110) should increase or decrease the voltage delivered to electrode (1128) of instrument (1120). If capacitive coupling current is at or above a pre-determined threshold current, generator (1110) may be directed to turn down the voltage to therefore decrease the capacitive redirection to a level that is below the injury threshold but still allows instrument (1120) and the operator to operate. Otherwise, if capacitive coupling energy is below the pre-determined threshold, generator (1110) may be directed to turn up the voltage to provide more power to instrument (1120) while still monitoring the threshold for capacitive coupling. Thus, by monitoring the level of capacitive coupling (e.g., too much leakage) rather than solely monitoring for the presence or absence of capacitive coupling, system (1100) is able to track the aberrant energy redirection as generator (1110) adjusts the voltage from potentially a high voltage power usage (e.g., 7,000 volts) to a significantly lower voltage (e.g., 1,000 volts) while still maintaining the same power level by simultaneously adjusting the output current. As these adjustments are made, generator (1110), sensors (1126, 1142, 1144, 1146) or other monitoring devices monitor the aberrant capacitive coupling current to ensure that the capacitive coupling current moves below a tissue damaging threshold level, at which point the adjustment allows instrument (1120) to continue to be used in the operation. In other words, capacitive coupling may be suitably addressed without requiring the surgical procedure to stop due to sudden interruption of power from generator (1110). In some cases, however, where ad hoc power modulation will not suffice to address capacitive coupling, it may ultimately be desirable to interrupt power from generator (1110) as a last resort.

If output energy from instrument (1120) is capacitively coupled to tissue of patient (P), a lower impedance load may be seen by generator (1110) relative to the impedance load provided by the tissue alone without the capacitive coupling. Monitoring abrupt changes in impedance could signal harmful arcing or breakdown. Thus, generator (1110) may be monitored for arcing, data of which may be used cooperatively with local electronics in instrument (1120) to better evaluate what percentage of the output power is being delivered to electrode (1128) versus to the capacitive coupling. This may allow the monitoring systems to provide feedback for generator (1110) output adjustments actively in real-time during an operation, thereby allowing generator (1110) to adjust the voltage or other electrical parameter(s) as necessary. In some versions, a shielding (1129) is included in instrument (1120) to collect capacitive coupling current to provide to sensors (1126, 1142, 1144, 1146) for measurements and monitoring. System (1100) may include controller (1108) (e.g., a hub or data center) having processing means for coupling with generator (1110); or the processing means may be included within generator (1110). The electrosurgery parameters may therefore be measured by sensors (1126, 1142, 1144, 1146) and compared, by the processor, with an estimate of what a normal application of energy or a normal tissue impedance would be for the operative situation. If either parameter is out of a predetermined range, then generator (1110) may be made aware that there is the possibility of capacitive coupling or a breakdown of the insulation system on the instrument.

As an alternative, tuner (1148) may be coupled with output port (1114) to adjust the capacitive and/or inductive load automatically to therefore adjust for higher or lower capacitance components of instrument (1120), such as a metallic shield (1129) that is in, on, or around at least a portion of instrument (1120). Components could be measured upon connection of instrument (1120) and then adjustments made to compensate. In addition or in the alternative, as exceedingly high voltages are sensed by one or more sensors (1126, 1142, 1144, 1146), system (1100) may add or subtract some capacitance and/or inductance to reduce the energy output at port (1114).

As depicted in FIG. 20, an example of a method (1150) as described above begins with a step (block 1152) where one or more sensors (1126, 1142, 1144, 1146) determine the maximum threshold or range of energy loss allowable and/or the maximum threshold or range of impedance change allowable during the operation. These thresholds or ranges may be determined by system (1100), such as by controller (1108) or generator (1110), based upon known parameters of the surgical operation at hand, based on known parameters of instrument (1120), based on prior operation data collected from similar surgical operations or with similar instruments, and/or based on other factors. In some versions, tuner (1142) automatically executes a calibration algorithm upon coupling of instrument (1120) with generator (1110) to detect the load parameters of the coupled instrument (1120), and thereby determines appropriate the maximum threshold or range of energy loss allowable and/or the maximum threshold or range of impedance change allowable during the operation, based on the detected load parameters of the coupled instrument (1120). Such ad hoc determinations may further allow for power delivery adjustments to be made before the power is even initially delivered, to compensate for the detected load parameters of the coupled instrument (1120). By way of example only, such initial ad hoc power delivery adjustments may include adding or subtracting capacitance and/or inductance to the output that will be delivered to the coupled instrument (1120), to thereby minimize the risks of capacitive couplings occurring during use of the coupled instrument (1120) during the surgical procedure. Regardless of whether initial ad hoc power delivery adjustments are made based on detected characteristics of the coupled instrument (1120), the maximum energy loss threshold or range that is determined (block 1152), and the maximum threshold or range of impedance change that is determined (block 1152), may each be configured such that system (1100) directs generator (1110) to adjust the power output of generator (1110) as required to ensure that instrument (1120) operates effectively and patient (P) injury is avoided.

Once the thresholds or ranges are determined, at a next step (block 1154), the operator activates end effector (e.g., electrode (1128)) of instrument (1120) to begin the operation on patient (P). As described above, at a subsequent step (block 1156), one or more of sensors (1126, 1142, 1144, 1146) monitor the capacitive coupling current induced along the components of instrument (1120) and/or wire (1130). During this same step (block 1156), the impedance may also be monitored.

Based on the data from one or more sensors (1126, 1142, 1144, 1146), method (1150) further includes a step of determining (block 1166), via controller (1108) or generator (1110), whether the capacitive coupling current meets or exceeds the threshold or range that was previously determined (block 1152). If the capacitive coupling current does not meet or exceed the threshold or range that was previously determined (block 1152), method (1150) further includes a step of determining (block 1168), via controller or generator (1110), whether the impedance change has meets or exceeds the threshold or range that was previously determined (block 1152), where such an impedance change would be indicative of an undesirable capacitive coupling. For instance, an abrupt and substantial reduction in impedance may indicate undesirable arcing between electrode (1128) and tissue, which may be a result of undesirable capacitive coupling. If neither the capacitive coupling current nor the impedance change has met or exceeded the corresponding threshold or range that was previously determined (block 1152), then system (1100) continues activation of the end effector (block 1154) and monitoring capacitive coupling current and/or impedance (block 1156).

If the determination (block 1166) reveals that the capacitive coupling current meets or exceeds the threshold or range that was previously determined (block 1152), then method (1150) proceeds to a step (block 1160) where one or more output parameters (e.g., voltage magnitude, current limit, power limit, etc.) of generator (1110) are adjusted to prevent or otherwise address the occurrence of capacitive coupling. Similarly, if the determination (block 1168) reveals that the impedance change meets or exceeds the threshold or range that was previously determined (block 1152), then method (1150) proceeds to a step (block 1160) where one or more output parameters (e.g., voltage magnitude, current limit, power limit, etc.) of generator (1110) are adjusted to prevent or otherwise address the occurrence of capacitive coupling. Such adjustments may be executed via tuner (1148), as described above. In some scenarios, such adjustments include reducing the output voltage of generator (1110) while still maintaining substantially the same power level (despite the reduction of voltage).

After adjusting the output parameters of generator (1110) (block 1160), system (1100) may determine (block 1162) whether these adjusted output parameters exceed the appropriate limits. If the adjusted output parameters do not exceed the appropriate limits, then system (1100) may continue activation of the end effector (block 1154) and monitoring capacitive coupling current and/or impedance (block 1156). The operator may thus continue the surgical procedure without interruption, with system (1100) providing ad hoc adjustments to power delivery from generator (1110), based on real-time feedback from one or more sensors (1126, 1142, 1144, 1146), to prevent undesirable results that might otherwise occur due to capacitive coupling during operation of instrument (1120).

In the event that systems (1100) determines (block 1162) that the adjusted output parameters exceed the appropriate limits, this may mean that system (1100) is unable to make appropriate adjustments to the energy delivered by generator (1110) to instrument (1120) to avoid undesirable results from capacitive coupling. In such scenarios, as a last resort, method (1150) may provide deactivation of the end effector of instrument (1120) (block 1164). Such deactivation may be provided by ceasing or otherwise interrupting energy delivery from generator (1110) to instrument (1120). In some variations, this deactivation (block 1164) may be provided for a predetermined duration (e.g., one second, five seconds, one minute, five minutes, etc.). After the expiry of this predetermined duration, the method may start back with activation of end effector (1154), allowing the surgical procedure to continue once again in accordance with method (1150). In the event that deactivation (block 1164) is necessary, system (1100) may also provide some kind of alert to the operator to indicate that such deactivation (block 1164) is intentional, to thereby avoid confusion by the operator mistakenly thinking that system (1100) has malfunctioned or that some other power failure has occurred. Such an alert may take the form of a visual alert, an audible alert, a haptic alert, and/or combinations of such forms.

VI. Example of Energized Surgical Instrument System with Multi-Generator Output Monitoring The following description relates to examples of different features that may be incorporated into any of the various surgical systems described above. Thus, the below-described features may be combined in various permutations as will be apparent to those skilled in the art in view of the teachings herein. Similarly, various ways in which the below-described features may be incorporated into any of the various surgical systems described above will be apparent to those skilled in the art in view of the teachings herein. It should be understood that the below-described features may be incorporated into robotically controlled surgical instruments and/or handheld surgical instruments.

As noted above, some aspects of the present disclosure are presented for a surgical instrument with improved device capabilities for reducing undesired operational side effects. In particular, as described with respect to FIG. 1, some surgical instruments or surgical systems may be configured to apply two or more different types of energy modalities. For example, this may include instruments configured to apply two or more of monopolar RF, bipolar RF, or ultrasonic energy to tissue. Application of two or more energy modalities may in some instances require two or more generators; or in other versions, two or more generator outputs associated with the same generator. However, if two or more energy modalities are used concurrently, the power outputs may induce crosstalk between the generator outputs thereby causing unwanted effects as either instrument contacts the tissue of the patient. Crosstalk may include signal amplification, reduction, interference, or other interactions between the two outputs. It may therefore be desirable to actively monitor one generator output using a monitoring array or generator to provide a second generator a set of energy output parameters. By doing so, the second generator may thereby be capable of outputting an energy signal that does not induce crosstalk between the two or more generator outputs.

Figure 21:
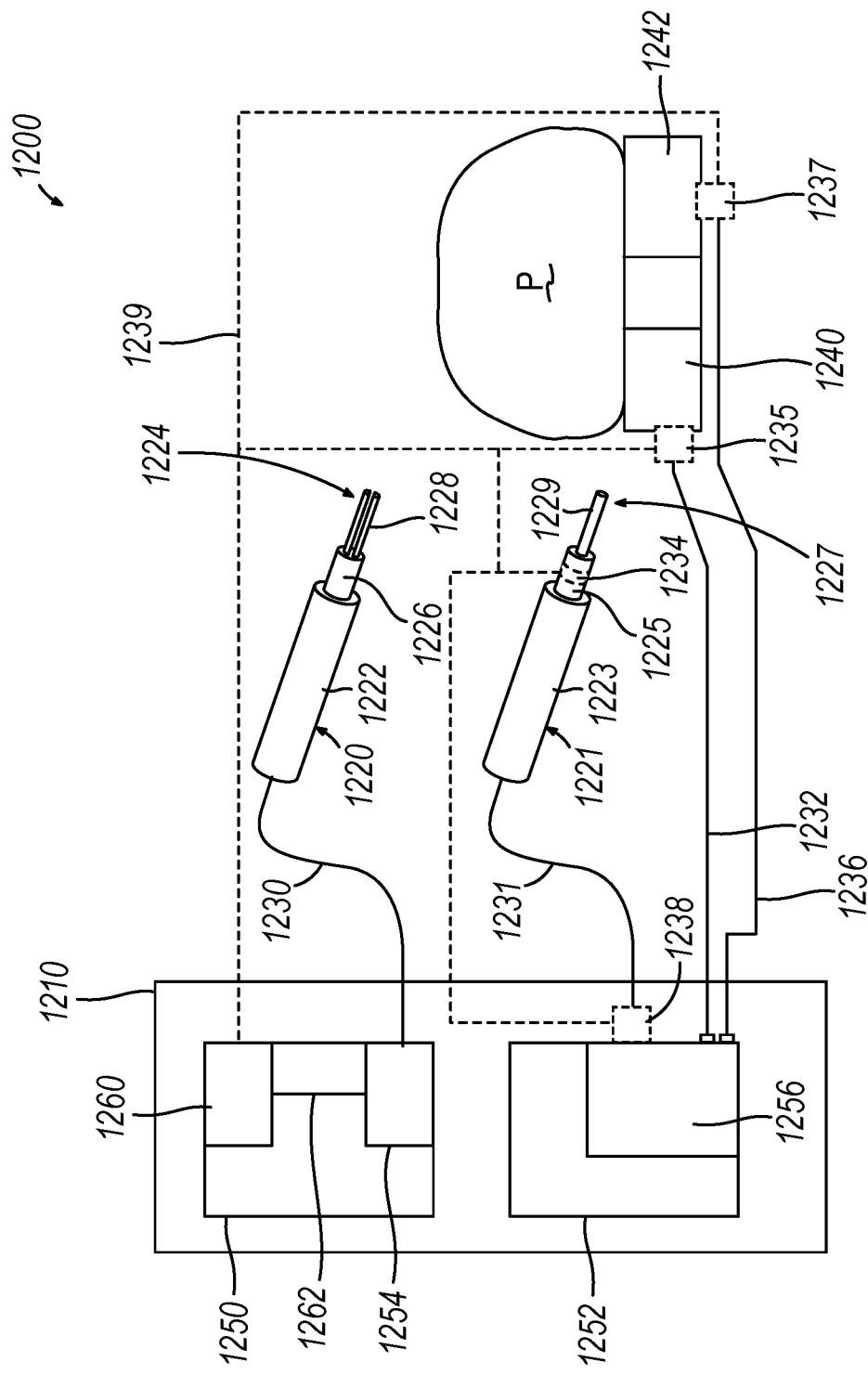
FIG. 21 depicts a schematic view of an example of a dual energy system including instruments that are operable to apply bipolar and monopolar energy to tissue.

FIG. 21 shows one exemplary a dual energy delivery system (1200) that includes a power generator (1210), a first delivery instrument (1220), a second delivery instrument (1221), a first ground pad assembly (1240), and a second ground pad assembly (1242). In addition to the following teachings, instruments (1220. 1221) may be constructed and operable in accordance with at least some of the teachings of U.S. Pub. No. 2019/0201077, issued as U.S. Pat. No. 11,291, 495 on Apr. 5, 2022, the disclosure of which is incorporated by reference herein, in its entirety; and/or various other references cited herein. Power generator (1210) may include a first generator module (1250) and a second generator module (1252), each being operable to deliver different energy modalities via power modules (1254, 1256) to instruments (1220, 1221) via cables (1230, 1231), respectively.

First instrument (1220) may be, for example, a bipolar RF instrument. First instrument (1220) includes a body (1222), a sensor (1226), and an end effector (1224) having a distal electrode assembly (1228) that is configured to contact patient (P) and thereby apply bipolar RF energy to the patient (P). In some versions, electrode assembly (1228) has two electrodes that are positioned to contact tissue simultaneously to thereby deliver bipolar RF energy to the tissue. In some variations, electrode assembly (1228) has more than two electrodes. By way of example only, sensor (1226) may be configured to monitor whether excess or inductive energy is radiating from instrument (1220).

Second instrument (1221) may be, for example, a monopolar RF instrument. Second instrument (1221) also includes a body (1223), a sensor (1225), and an end effector (1227) having a distal electrode (1229) that is configured to contact patient (P) and cooperate with one or more ground pad assemblies (1240, 1242) to apply RF energy to the patient (P). By way of example only, sensor (1225) may be configured to monitor whether excess or inductive energy is radiating from instrument (1220). Based on signals from sensor (1225), a control module in power generator (1210) may passively throttle the ground return from ground pad assemblies (1240, 1242) based on data from sensor (1225). While a bipolar instrument (1220) and a monopolar RF instrument (1221) are described, it should be understood that any two or more instruments may instead be utilized having any two or more energy modalities, such as monopolar RF, bipolar RF, ultrasonic, or any combination thereof.

As shown, a dual ground pad configuration may be utilized for monopolar RF embodiments, comprising two or more resistive continuity ground pads (1240, 1242) that provide direct contact between the skin of the patient (P) and one or more metallic components of the ground pad. In some other versions, ground pad assemblies (1240, 1242) comprise a capacitive coupling ground pad that includes a gel material that is interposed between the patient (P) and a ground return plate. In the present example, ground pad assemblies (1240, 1242) are positioned under the patient (P) and are coupled to power generator (1210) via cables (1232, 1236), respectively.

In some versions of energy delivery system (1200), one or both generator modules (1250, 1252) may include a power monitor such as sensor module (1260). Sensor module (1260) of one generator module (1250) may include a data processor configured to monitor energy present at various points in energy delivery system (1200) that are associated with the instrument (1221) affiliated with the other generator module (1252), particularly output module (1256). Thus, the various measured points showing the energy being output to patient (P) by the second generator module (1252) may be monitored by the first generator module (1250) so that first generator module (1250) may adjust its output parameters to avoid crosstalk.

Sensors (1234, 1235, 1237, 1238) may include, for example, RF power sensors, ammeters, voltmeters, ultrasonic transducers, or other similar power sensing instruments, and may be configured to monitor energy flowing through or radiating from various points being powered by power module (1256), and communicate energy measurements back to sensor module (1260) via communication cable (1239). Particularly, a first sensor (1234) may be positioned on instrument (1221) and may be configured to measure a capacitive coupling energy, a second sensor (1235) may be positioned on return cable (1232) from first ground pad assembly (1240) to monitor energy flowing back to generator module (1252) from patient (P), a third sensor (1237) may be positioned on return cable (1236) from second ground pad assembly (1242) to monitor energy flowing back to generator module (1252) from patient (P), and a fourth sensor (1238) may be positioned on cable (1231) to monitor energy being output from power module (1256) to instrument (1221). While four exemplary sensors (1234, 1235, 1237, 1238) are described at four distinct positions for monitoring energy flowing through or radiating from various points being powered by power module (1256), it should be understood that various other sensor positions have been contemplated and only one or a subset of sensors (1234, 1235, 1237, 1238) may be included in other variations of system (1200).

As described, during operation, sensor module (1260) may monitor signals from any one or more of sensors (1234, 1235, 1237, 1238) to determine the parameters of second output module (1256) to second instrument (1221) and communicate the parameters to first output module (1254) through a data connection (1262). Thereafter, first output module (1254) is configured to adjust its own output energy parameters to first instrument (1220) to avoid outputting too similar of a signal as second output module (1256) is outputting to second instrument (1221). Sensors (1234, 1235, 1237, 1238) may be configured to monitor any energy parameters, such as current, voltage, frequency, power level, and/or wave shape, etc.; and subsequently, first output module (1254) may be configured to adjust those same energy parameters. These adjustments may be made to avoid amplification, cancellation, interference, and/or other interactions between the outputs of output modules (1254, 1256). In other words, second output module (1256) may make ad hoc adjustments, in real time, to automatically adjust the frequency, wave shape, and/or other parameters of its own output to thereby avoid amplification, cancellation, interference, and/or other interactions with the sensed output of first output module (1254). For example, if sensor module (1260) determines that second output module (1256) is outputting a monopolar RF signal of 400 kHz, first output module (1254) may adjust its own bipolar RF output signal to 800 kHz or 1 MHz to adequately distinguish the signals. In some versions, a frequency multiplier circuit (e.g., a two-diode odd-order frequency multiplier, etc.) may be utilized with a single generator output module.

Some generator systems may respond poorly to excessive capacitance in the load. In some instances, this may lead to the generator's tuned circuit output producing higher than expected values of voltage. These higher voltages may exceed the ratings as provided by the generator manufacturer. This overvoltage situation may force the instrument that is being powered by the generator to operate in an out-of-bounds region where the instrument insulation systems are not rated for this higher voltage, which may lead to a potentially dangerous situation where the insulation breaks down and an electric arc is formed. Electric arcs may be highly undesirable in surgery as they may be unpredictable and suddenly burn material around them, thereby releasing chemicals and components that are not intended to be present in the surgical field. The burning of the insulation may further expose conductive surfaces that are not intended to be in contact with the patient. Thus, to prevent or otherwise alleviate these issues, energy delivery system (1200) may be further configured to perform energy parameter adjustments with respect to a time constant, the time constant being based on the natural frequency of the electrical system. Particularly, the time constant is equal to the product of the circuit resistance (in ohms) and the circuit capacitance (in farads).

To perform energy parameter adjustments with respect to the time constant, one or more of sensors (1234, 1235, 1237, 1238) may monitor the capacitive load and the resistive load. The capacitive load may be monitored, for example, by sensor (1234) measuring the parasitic capacitive coupling induced the instrument (1221). The resistive load may be monitored, for example, by a combination of sensors (1234, 1235, 1237, 1238) measuring the tissue load as may be defined by the muscle-to-fat ratio. It should be understood that the measurements and time constant adjustments described above may, in some versions, be performed by the energy delivery system (1200) without the cooperation with either generator module (1250, 1252).

Figure 22:
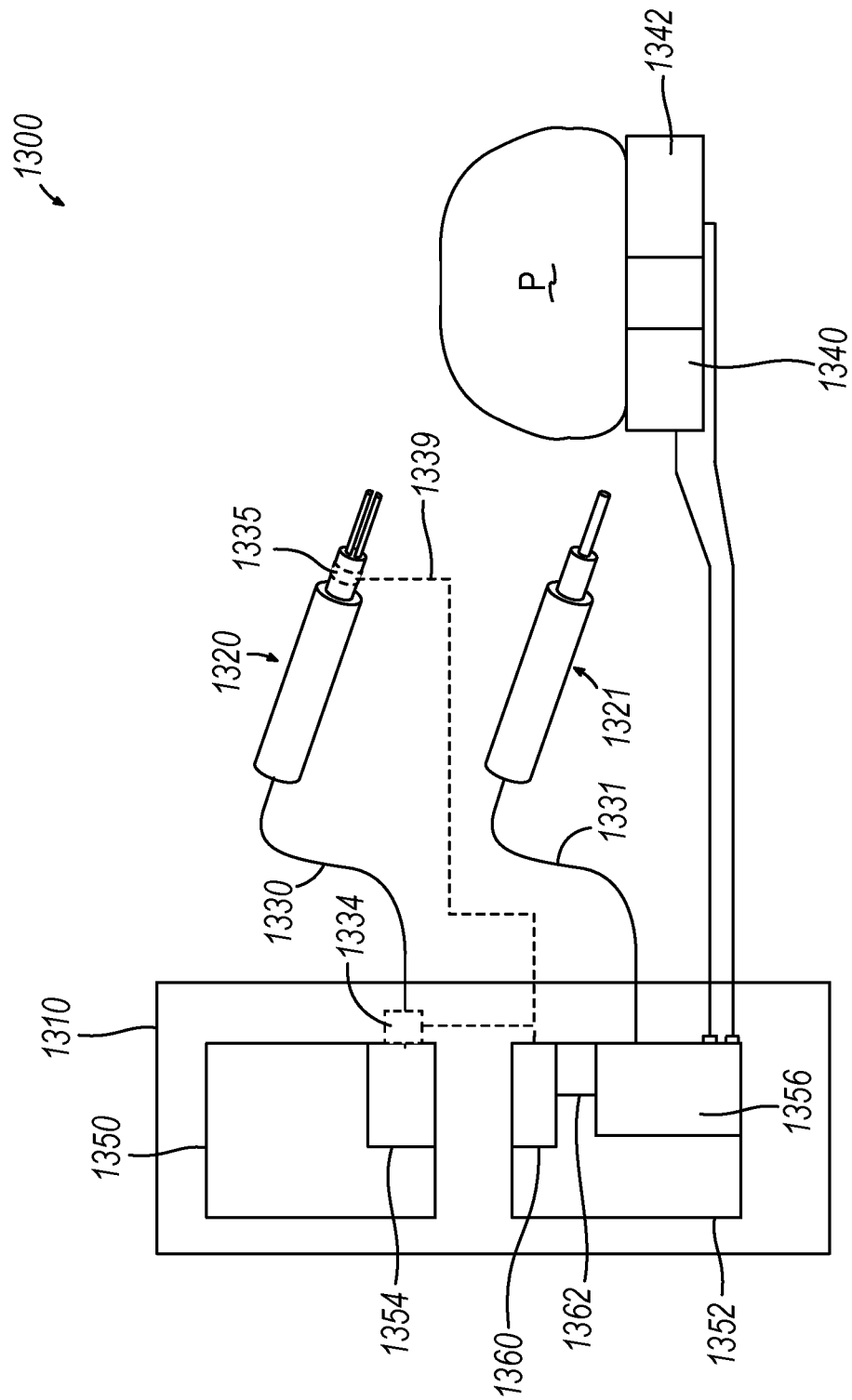
FIG. 22 depicts a schematic view of another example of a dual energy system including instruments that are operable to apply bipolar and monopolar energy to tissue.

FIG. 22 shows an alternative configuration (1300) of energy delivery system (1200). The components and their functionalities of energy delivery system (1300) are the same as described with regard to energy delivery system (1200) except as described below. Particularly, energy delivery system (1300) includes a power generator (1310), a first delivery instrument (1320), a second delivery instrument (1321), a first ground pad assembly (1340), and a second ground pad assembly (1342). Power generator (1310) may include a first generator module (1350) and a second generator module (1352), each being operable to deliver different energy modalities via power modules (1354, 1356) to instruments (1320, 1321) via cables (1330, 1331), respectively. Further, while a bipolar instrument (1320) and a monopolar RF instrument (1321) are described, it should be understood that any two or more instruments may instead be utilized having any two or more energy modalities, such as monopolar RF, bipolar RF, ultrasonic, or any combination thereof.

In this version, generator module (1352) includes a power monitor such as sensor module (1360) that is coupled with power module (1356). Sensor module (1360) of second generator module (1352) may include a data processor configured to monitor energy present at various points in energy delivery system (1300) that are associated with the instrument (1320) affiliated with the other generator module (1350), particularly output module (1354). Thus, the various measured points showing the energy being output to patient (P) by the first generator module (1350) may be monitored by the second generator module (1352) so that second generator module (1352) may adjust its output parameters to avoid crosstalk. Sensors (1334, 1335) may include, for example, RF power sensors, ammeters, voltmeters, ultrasonic transducers, or other similar power sensing instruments; and may be configured to monitor energy flowing through or radiating from various points being powered by power module (1354) and communicate energy measurements back to sensor module (1360) via communication cable (1339). Particularly, a first sensor (1334) may be positioned at the output of power module (1354) and may be configured to measure the output energy signal provided to power instrument (1320); while a second sensor (1335) may be positioned on instrument (1320) and may be configured to measure a capacitive coupling energy. While two exemplary sensors (1334, 1335) are described at two distinct positions for monitoring energy flowing through or radiating from various points being powered by power module (1354), it should be understood that various other sensor positions have been contemplated and only one or a subset of sensors (1334, 1335) may be included.

As described, during operation, sensor module (1360) may monitor any one of sensors (1334, 1335) to determine the parameters of first output module (1354) to first instrument (1320) and communicate the parameters to second output module (1356) through a data connection (1362). Thereafter, second output module (1356) is configured to adjust its own output energy parameters to second instrument (1321) to avoid outputting too similar of a signal as first output module (1354) is outputting to first instrument (1320). Sensors (1334, 1335) may be configured to monitor any energy parameters, such as current, voltage, frequency, power level, and/or wave shape, etc.; and subsequently, second output module (1354) may be configured to adjust those same energy parameters. These adjustments may be made to avoid amplification, cancellation, interference, and/or other interactions between the outputs of output modules (1354, 1356). In other words, second output module (1356) may make ad hoc adjustments, in real time, to automatically adjust the frequency, wave shape, and/or other parameters of its own output to thereby avoid amplification, cancellation, interference, and/or other interactions with the sensed output of first output module (1354). For example, if sensor module (1360) determines that first output module (1354) is outputting a monopolar RF signal of 400 kHz, second output module (1356) may adjust its own bipolar RF output signal to 800 kHz or 1 MHz to adequately distinguish the signals. In some versions, a frequency multiplier circuit (e.g., a two-diode odd-order frequency multiplier, etc.) may be utilized with a single generator output module.

While the foregoing examples shown in FIGS. 21-22 have been shown in the context of handheld instruments (1220, 1221, 1320, 1321), the same teachings may be readily applied in the context of robotically controlled instruments, including but not limited to robotically controlled instruments as described above and as described in various references cited herein. Similarly, while the foregoing examples shown in FIGS. 21-22 have been shown in the context of external generators (1210, 1310) that are coupled with instruments (1220, 1221, 1320, 1321) via cables (1230, 1231, 1330, 1331), the same teachings may be readily applied in the context of instruments having integral generators (1210, 1310) contained within the body of the instrument. An example of such a scenario may include an instrument having an end effector that is operable to apply two or more kinds of energy modalities (e.g., monopolar RF, bipolar RF, ultrasonic, etc.), with two or more corresponding kinds of generators contained within the body of the instrument to drive those two or more energy modalities.

VII. Example of Electrosurgical Instrument with Shaft Voltage Monitor

The following description relates to examples of different features that may be incorporated into any of the various surgical systems described above. Thus, the below-described features may be combined in various permutations as will be apparent to those skilled in the art in view of the teachings herein. Similarly, various ways in which the below-described features may be incorporated into any of the various surgical systems described above will be apparent to those skilled in the art in view of the teachings herein. It should be understood that the below-described features may be incorporated into robotically controlled surgical instruments and/or handheld surgical instruments.

Some versions of the instruments described herein may provide a floating ground with respect to conductive components within a shaft assembly of the instrument. In scenarios where a floating ground exists, such conductive components are not electrically coupled with earth ground. A floating ground may isolate ground return paths within the instrument and bring them to one point, effectively creating an ad hoc ground that is isolated relative to actual ground. A floating ground may have an associated ad hoc voltage, and control circuitry may adjust a voltage associated with the floating ground. Ultimately, a floating ground may provide electrical isolation for components within an electrical circuit in the absence of earth ground. Electrically conductive components may be understood as having a floating potential or voltage when such electrically conductive components are not electrically coupled with earth ground.

Some aspects of the present disclosure are presented for monitoring voltage potentials in components of a shaft assembly, and adaptively adjusting power, adjusting sensing signals, and/or providing some other kind of system response based on detected voltage potentials in components of the shaft assembly. The voltage potentials of one shaft component may be monitored relative to the common return path and relative to the potentials of the other shaft components. In some cases, variations in voltage potentials present at different components of an electrosurgical system may cause ground loops. For instance, the difference in potential between the return path ground on the generator and the local ground on the end effector that is in use may cause a ground loop. The effects of ground loops may depend on the severity of the potential difference between the grounding points. Small ground loops may inject noise onto a system and cause interruption or loss of communication on data lines. Large ground loops may cause damage to electronic components or cause the entire system to reset or become temporarily inoperative. It may therefore be desirable to actively monitor variations in potentials and to take corrective action.

As will be described in greater detail below, variations in potentials or voltages may be monitored to control the electrical connection to the components in order for undesired voltages to be drained or floated relative to the return path, based on a comparison of the measured voltage potential to a predetermined max threshold value. In some instances, shaft components and/or control electronics may be shifted between an electrically floating condition and an interconnected condition on an intermittent basis. Such shifting may ensure accurate local measuring by sensors and accurate operation by active electrical components; while allowing the draining of otherwise parasitic power signals and/or preventing incidental unintended electrification of system components. In some instances, local sensing may be paused or adjusted while a voltage is drained as part of a safety draining process as described herein. Corrective action may include any one or more of adjusting the noise correction thresholds, adjusting the transformation to correct for the introduced error, providing the system a "blackout" where it needs to ignore the sensors within the effects of the potential shift, or even rebooting or shutting off power to the sensor to protect it from damage.

In some versions, monitoring for variations in potential may include monitoring the shaft components for voltage potentials relative to one another and/or relative to the return path to the generator. For example, in versions where the shaft assembly is comprised of a plurality of metallic components, the instrument may include a wiring harness or flex circuit to connect the end effector to the outer housing assembly.

Figure 23:
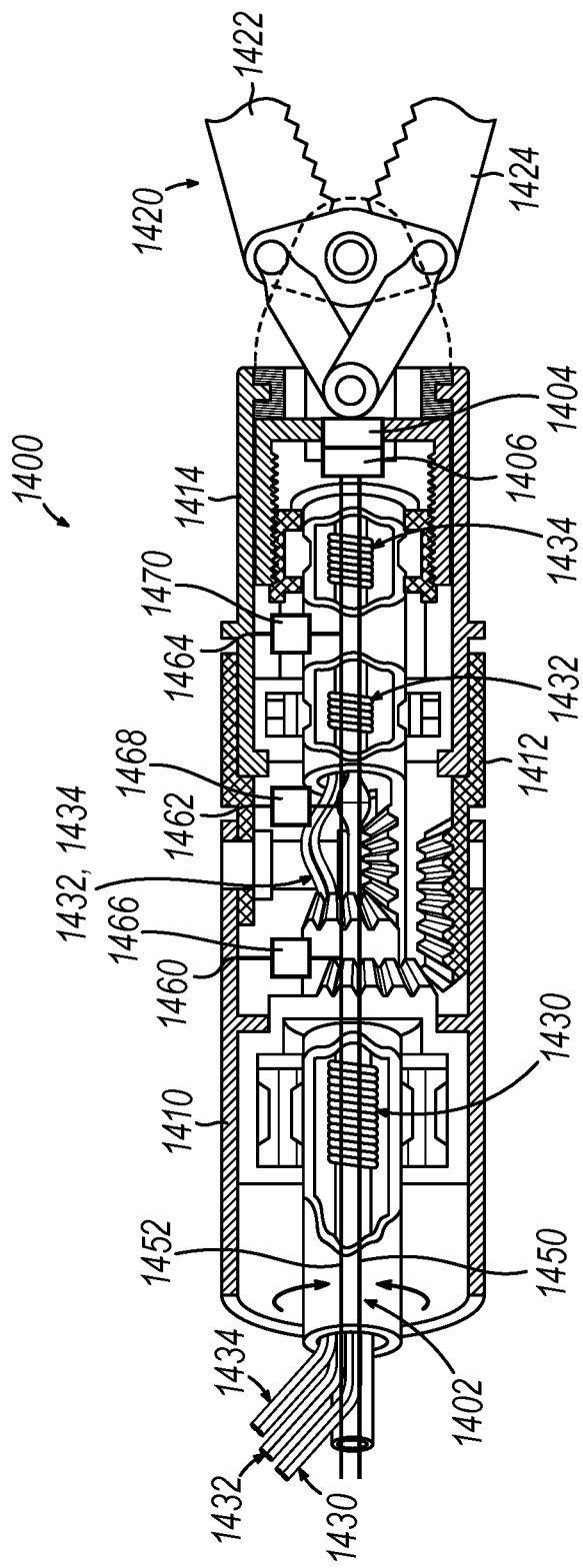
FIG. 23 depicts a side elevation view of a portion of another shaft assembly that may be incorporated into a surgical instrument, with housing components of the shaft being shown in cross-section to reveal internal components of the shaft.

FIG. 23 illustrates a portion of an instrument (1400) that includes an elongated shaft (1410). It should be understood that, while instrument (1400) is illustrated and described in detail, various other electrosurgical instruments have been contemplated including, but not limited to, the instruments described herein above. A console (not shown) of instrument (1400) may receive voltage measurements from one or more sensors, as will be described below, and react accordingly to initiate a corrective action. By way of example only, the console may be configured similar to console (20) described above with reference to FIG. 1, and may include a data processor configured and operable to initiate the corrective action, adjust the power profile sent to instrument (1400), or float or drain any of the components forming the body of instrument (1400). Further, the console may be a component of a robotic electrosurgical system, as described above. Various suitable forms that a console for instrument (1400) may take will be apparent to those skilled in the art in view of the teachings herein.

Instrument (1400) of the present example is substantially similar to instrument (600) of FIG. 9, as described above, except for the differences described below. Instrument (1400) includes a first articulating segment (1412) and a second articulating segment (1414). End effector (1420) is positioned at the distal end of second articulating segment (1414). End effector (1420) of this example includes a pair of jaws (1422, 1424) that are operable to pivot toward and away from each other to grasp tissue. In some versions, one or both of jaws (1422, 1424) includes one or more electrodes that is/are operable to apply RF energy to tissue as described herein. Such electrodes may be powered via electrical connectors (1404, 1406), which are routed through instrument via a wiring harness (1402). While a wiring harness (1402) is used in the present example, any other suitable kind of conductor assembly (e.g., flex circuit ribbon, etc.) may be used as will be apparent to those skilled in the art in view of the teachings herein. In addition, or in the alternative, end effector (1420) may include an ultrasonic blade and/or various other features in addition to, or in lieu of, including jaws (1422, 1424). Segments (1412, 1414) may be operable to pivot relative to shaft (1410) and relative to each other to thereby deflect end effector (1420) laterally away from or toward the central longitudinal axis of shaft (1410).

Instrument (1400) of this example further includes a first wire set (1430) spanning through shaft (1410), a second wire set (1432) spanning through shaft (1410) and both segments (1412, 1414), and a third wire set (1434) spanning further through shaft (1410) and both segments (1412, 1414). Wire sets (1430, 1432, 1434) may be operable to control movement of segments (1412, 1414) relative to shaft (1410). For instance, power may be communicated along one or more of wire sets (1430, 1432, 1434) to selectively engage or disengage corresponding clutching mechanisms, to thereby allow lateral deflection of one or both of segments (1412, 1414) relative to shaft (1410); and or rotation of one or both of segments (1412, 1414) relative to shaft (1410). Alternatively, power may be communicated along one or more of wire sets (1430, 1432, 1434) to drive corresponding solenoids, motors, or other features to actively drive lateral deflection of one or both of segments (1412, 1414) relative to shaft (1410); and or rotation of one or both of segments (1412, 1414) relative to shaft (1410). In versions where end effector (1420) is operable to apply RF energy to tissue, one or more additional wire sets, such as wiring harness (1402) extends along shaft (1410) and segments (1412, 1414), in addition to wire sets (1430, 1432, 1434), to couple with connectors (1404, 1406) to provide power to end effector (1420).

Connectors (1404, 1406) of the present example include a proximal connector (1404) and a distal connector (1406), which are configured to removably mate with each other. Wiring harness (1402) is coupled with proximal connector (1406), such that wires (1450, 1542) of wiring harness (1402) couple with distal connector (1404), which is then configured to mate with proximal connector (1406) to provide power to end effector (1420). By way of example only, such power may include bipolar RF energy for electrodes on end effector (1420). Return path ground (1452) (e.g., ground wire, ground trace, etc.) from end effector (1402) may have intermediate electrical connections to metallic components in the shaft assembly, such as shaft (1410), first articulating segment (1412), and second articulating segment (1414), in order to be able to monitor the voltage potential of each component (1410, 1412, 1414) relative to return path (1452) and relative to each other component (1410, 1412, 1414). This monitoring may be used by the console to control the electrical connection to the components (1410, 1412, 1414) in order to allow them to be electrically drained or floated relative to return path (1452) based on the comparison of the measured voltage potential to a predetermined max threshold voltage value.

As shown, wiring harness (1402), or alternatively, a flexible circuit, connects end-effector (1420) to a handle or other body of the electrosurgical instrument (1400) and may include conductive attachment points (1460, 1462, 1464) to conductive structures within the instrument (1400). These conductive attachment locations (1460, 1462, 1464) may allow integrated sensors (1466, 1468, 1470) to monitor the voltage potential of the components (1410, 1412, 1414), respectively, as each relates to the control electronics (e.g., the generator or related components) and return path ground (1452). While sensors (1466, 1468, 1470) are integrated adjacent to corresponding attachment locations (1460, 1462, 1464) in the present example, other configurations may be used. By way of example only, a wire, conductive trace, or other electrically conductive path may extend from each attachment location (1460, 1462, 1464) to a proximal location (e.g., to a proximal portion of shaft (1410), to a body of instrument (1400) that is proximal to shaft (1410), to a console that is coupled with instrument (1400), etc.); and be coupled with return path (1452) at such a proximal location in order to effectively monitor potentials between attachment locations (1460, 1462, 1464) and return path (1452).

If the system detects a potential change in one of the components (1410, 1412, 1414), the system may determine if the potential change exists due to an externally applied voltage source or from a capacitive coupling of the component (1410, 1412, 1414) with another component (1410, 1412, 1414) that is being intentionally activated with electrical power. Once the system determines the source of the voltage variation, the system may actively ground or clamp off the voltage potential, warn the user of external contact with another energized instrument, and/or apply an adjustment to the rest of the sensors (1466, 1468, 1470) proportionate to the effect caused by the one sensed potential. In some versions, sensors (1466, 1468, 1470) include high impedance sensors positioned between the metallic frame component (1410, 1412, 1414) and return path (1452). In versions utilizing a flexible circuit in place of wiring harness (1404), wires (1450, 1542) may instead be included as conductive traces routed through the body of instrument (1400).

In some versions, sensors (1466, 1468, 1470) are configured to monitor the voltage potential relative ground path (1452) of all the metallic shaft components, such as components (1410, 1412, 1414), and only selectively ground the ones that have accumulated electrical current to remove. Thus, to operate in the safest configuration, each component (1410, 1412, 1414) may remain electrically floating unless a particular component (1410, 1412, 1414) requires discharge. In this context, "electrically floating" means that a component (1410, 1412, 1414) is not electrically coupled with ground. In some scenarios, a component (1410, 1412, 1414) that is electrically floating may have a certain floating voltage. Such floating voltages may be induced by electromagnetic fields that are generated in component (1410, 1412, 1414) by proximate, activated components. Such floating voltages may also be caused by charge accumulating within component (1410, 1412, 1414).

In some versions, each component (1410, 1412, 1414) may be shifted from an electrically floated configuration to an interconnected configuration, where one or more components (1410, 1412, 1414) are at least temporarily electrically coupled together. This may be done intermittently to ensure accurate local measuring and operation while still allowing draining of any parasitic or incidental electrifying of the system. Thus, each component (1410, 1412, 1414) may be maintained in an electrically floating state by default; and only be grounded through the console in the event that it is determined that a particular component (1410, 1412, 1414) has built up a potential that exceeds the threshold value such that the component (1410, 1412, 1414) should be discharged.

As previously noted, shaft (1410) and/or end effector (1420) may include one or more operation sensors operable to sense one or more parameters associated with operation of end effector (1420). By way of example only, such an operation sensor may include a force sensor (e.g., force sensor (114), etc.) that is operable to sense a clamping force that is being applied by jaws (1422, 1424) to tissue; or a force sensor that is operable to sense transverse loads being applied to shaft (1410) during engagement of tissue by end effector (1420). By way of further example only, an operation sensor may include a temperature sensor that is operable to sense the temperature of end effector (1420) or the temperature of tissue that is being engaged by end effector (1420). As another merely illustrative example, an operation sensor may include an impedance sensor that is operable to sense the impedance of tissue that is being engaged by end effector (1420). As yet another merely illustrative example, an operation sensor may include a position sensor (e.g., position sensor (112), sensors (720, 722, 724), sensors (770, 772), etc.) that is operable to sense a position or orientation of shaft (1410) and/or end effector (1420). Other kinds of operation sensors that may be incorporated into shaft (1410) and/or end effector (1420) will be apparent to those skilled in the art in view of the teachings herein.

In versions of instrument (1400) with operation sensors such as those described above, the voltage shifting described herein may ensure accurate local measuring by such operation sensors and reduce noise that might otherwise occur within signals from such operation sensors. In some instances, sensing by operation sensors may be paused or adjusted while a voltage is drained as part of a safety draining process as described herein. Corrective action may also include any one or more of adjusting noise correction thresholds, adjusting the transformation to correct for the introduced error, providing the system a "blackout" where console needs to ignore signals from operation sensors within the effects of the potential shift, or even rebooting or shutting off power to an operation sensor to protect the operation sensor from damage.

In some versions, sensors (1466, 1468, 1470) and/or any other sensors within shaft (1410) or end effector (1420) may be paused, or otherwise deactivated and disconnected, while one or more of components (1410, 1412, 1414) is at least temporarily grounded, whether such grounding connection is made via another component (1410, 1412, 1414), via dedicated ground path (1452), or via any other already-grounded component of instrument (1400).

In some instruments, such as a bipolar RF surgical stapling instrument with an end effector having bipolar electrodes near surgical staples, the bipolar electrodes may run the risk of contacting surgical staples, thereby creating a short circuit between the bipolar electrodes via one or more surgical staples. In monopolar instruments, capacitive coupling currents may accumulate on any metallic components forming the instrument shaft. To alleviate the risks associates with these scenarios, plastic components (or "metal insert interruptions") may be included within the shaft assembly to avoid having a shaft that is metallic along its entire length. For example, an electrically insulating member may be included in one or more of components (1410, 1412, 1414) to minimize the impact of these electrical current risks on the surrounding components; and further to minimize the propagation of the capacitive couple current upstream and downstream of instrument (1400). A molded plastic member, or otherwise a non-conductive member, may be inserted where the metal portions of components (1410, 1412, 1414) overlap. In such versions, the shaft assembly may lack a continuous path for unintended electrical continuity along the full length of the shaft assembly (other than such paths as intentionally provided by wires, etc.). In other words, electrically conductive structural components of the shaft assembly, that are not intended to conduct electricity, may include non-conductive structural components interposed therebetween to provide interruptions disrupting the electrical continuity that might otherwise exist. In some versions, adjacent components (1410, 1412, 1414) may include holes or keying features that allow one long, non-conductive plate to be coupled to the other via interlocking injection molded plastic cross-sections. Other suitable ways in which electrically interruptive, non-conductive structural components may be integrated into a shaft assembly will be apparent to those skilled in the art in view of the teachings herein.

VIII. Example of Electrosurgical Instrument with Electrical Resistance Monitor at Rotary Coupling The following description relates to examples of different features that may be incorporated into any of the various surgical systems described above. Thus, the below-described features may be combined in various permutations as will be apparent to those skilled in the art in view of the teachings herein. Similarly, various ways in which the below-described features may be incorporated into any of the various surgical systems described above will be apparent to those skilled in the art in view of the teachings herein. It should be understood that the below-described features may be incorporated into robotically controlled surgical instruments and/or handheld surgical instruments.

As noted above, some instruments may include joints in a shaft assembly where one component of the shaft assembly articulates relative to another component at a pivot point in the shaft assembly, or where one component of the shaft assembly rotates about a central longitudinal axis relative to another component of the shaft assembly, etc. Examples of rotary coupling joints in a shaft assembly are described above in the context of instrument (600) shown in FIG. 9; while other examples will be apparent to those skilled in the art in view of the teachings herein. Examples of pivoting articulation joints in a shaft assembly are described above in the context of shaft assembly (750) shown in FIG. 11; while other examples will be apparent to those skilled in the art in view of the teachings herein. In versions of instruments with telescoping shaft assembly components, one component of the shaft assembly may translate relative to another component of the shaft assembly to thereby change the effective length of the shaft assembly.

Regardless of whether an instrument includes a rotary joint, a pivoting articulation joint, a telescoping joint, and/or some other kind of joint, it may be necessary to provide electrical communication across such joints. For instance, such electrical communication may include communication of RF power from a console to an end effector via one or more movable joints within a shaft assembly. Such electrical communication may also include providing a common ground return path along the length of the shaft assembly (e.g., from the end effector to the console), with such a ground return path needing to pass through one or more movable joints within a shaft assembly. Such electrical communication may also include communication of signals from a sensor in an end effector or distal portion of a shaft assembly to the console via one or more movable joints within a shaft assembly. Some merely illustrative examples of sensors that may be included in a shaft assembly are described above in the context of shaft assembly (700) shown in FIG. 10 and shaft assembly (750) shown in FIG. 11, though other ways in which sensors may be integrated into a shaft assembly or end effector will be apparent to those skilled in the art in view of the teachings herein. For instance, in end effectors that include electrodes for applying bipolar RF energy to tissue those same electrodes may be used as sensors to sense impedance in tissue that is being contacted by the end effector. Regardless of what the electrical couplings are used for, movable joints of a shaft assembly may include one or more slip couplings (e.g., slip rings and corresponding leaf springs or other sliding contacts, etc.) or other kinds of couplings that are configured to provide electrical continuity across the joint without compromising freedom of movement at the joint.

In some scenarios, the electrical communication properties of electrical couplings at joints as described above may change during use of an instrument. For instance, such electrical couplings may be exposed to tissue debris, saline, bodily fluids, or other fluids during a surgical procedure, as it may be difficult to achieve fluid-tight seals at such joints. When such debris or fluids are conductive or at least semi-conductive, intrusion of such debris or fluids through the joints may ultimately reach the electrical couplings at the joints and thereby contaminate the electrical couplings, which may affect the electrical communication properties of those electrical couplings. This may include affecting the resistance and/or voltage at the joints. This may in turn introduce noise into electrical signals that are communicated across the joints; or in some cases, cause signal loss across the joints. Contamination of an electrical coupling may also create short circuits between contacts, cause heating of the contaminant(s), and/or cause heating of the joint. This undesired heat may cause undesired tissue trauma or other undesired effects in the surgical field, adversely affect operability of the instrument, and/or damage one or more components of the instrument. In some instances, as the electrical resistance at an electrical coupling of a movable joint increases, the heat generated at the electrical coupling increases; such that an increase in the resistance of an electrical coupling of a movable joint may be indicative of the amount of heat generated as an electrical signal or power passes through that electrical coupling.

In view of the foregoing, it may be desirable to monitor changes in electrical properties (e.g., voltage, electrical resistance, etc.) of electrical couplings (e.g., slip couplings, etc.) at movable joints (e.g., rotary couplings, pivoting articulation joints, telescoping joints, etc.) within an instrument; and provide an automated response in real time for changes that are detected. Such responses may include adjustments of generator power levels, signal processing magnitude, etc. In some instances, changes of resistance of the monitored components may result from positional changes (i.e., varied angular orientation of components relative to each other, varied articulation angles, etc.) of the instrument components; and the console may vary the power output during operation based upon the positional changes of certain components if the monitoring determines that an electrical coupling at a joint has become contaminated. Examples of how such monitoring and responding may be carried out are described in greater detail below.

Figure 24:
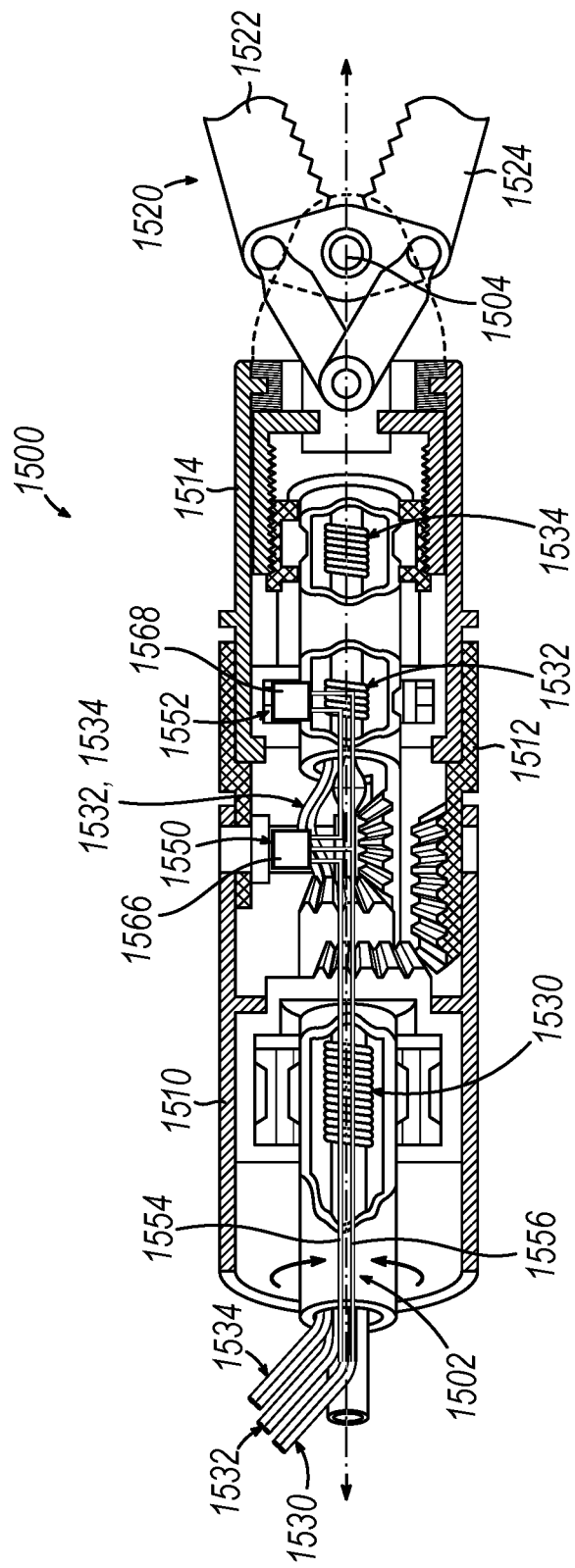
FIG. 24 depicts a side elevation view of a portion of another shaft assembly that may be incorporated into a surgical instrument, with housing components of the shaft being shown in cross-section to reveal internal components of the shaft.

FIG. 24 shows one example of the monitoring system described above. As shown in FIG. 24, an instrument (1500) includes an elongate shaft (1510). While instrument (1500) is illustrated and described in detail, various other electrosurgical instruments have been contemplated including, but not limited to, the instruments described herein above. Instrument (1500) includes a first articulating segment (1512) and a second articulating segment (1514). End effector (1520) is positioned at the distal end of second articulating segment (1514). End effector (1520) of this example includes a pair of jaws (1522, 1524) that are operable to pivot toward and away from each other to grasp tissue. In some versions, one or both of jaws (1522, 1524) includes one or more electrodes that is/are operable to apply RF energy to tissue as described herein. In addition, or in the alternative, end effector (1520) may include an ultrasonic blade and/or various other features.

Segments (1512, 1514) may be operable to pivot relative to shaft (1510) and relative to each other to thereby define joints (1550, 1552), respectively, to provide deflection of end effector (1520) laterally away from or toward the central longitudinal axis (1504) of shaft (1510). In addition, or in the alternative, one or both of segments (1512, 1514) may be operable to rotate relative to shaft (1510) about the central longitudinal axis (1504). Thus, joints (1550, 1552) may constitute pivoting articulation couplings and/or rotary couplings. In either case, joints (1550, 1552) may each include one or more slip couplings or other kinds of electrical couplings that are configured to provide electrical continuity across joints (1550, 1552) without compromising freedom of movement at joints (1550, 1552). Such electrical couplings may provide communication of RF power to end effector (1520), provide a ground return path across joints (1550, 1552), provide communication of electrical signals from one or more sensors in end effector (1520) and/or segments (1512, 1514), and/or provide any other kind of electrical communication.

A console or other processing module of instrument (1500) may receive resistance measurements, voltage measurements, temperature measurements, and/or other kinds of measurements from one or more sensors, as will be described below; and react accordingly to initiate the corrective action. By way of example only, such a console or other processing module may be configured similar to console (20) described above with reference to FIG. 1 or any other console or control circuit described herein; and may include a data processor configured and operable to initiate the corrective action, adjust the power profile sent to instrument (1500), or drain any excess energy stored within instrument (1500). Further, the console or other processing module may be a component of a robotic electrosurgical system, as described above.

Instrument (1500) of this example further includes a first wire set (1530) spanning through shaft (1510), a second wire set (1532) spanning through shaft (1510) and both segments (1512, 1514), and a third wire set (1534) spanning further through shaft (1510) and both segments (1512, 1514). Wire sets (1530, 1532, 1534) may be operable to control movement of segments (1512, 1514) relative to shaft (1510). For instance, power may be communicated along one or more of wire sets (1530, 1532, 1534) to selectively engage or disengage corresponding clutching mechanisms, to thereby allow lateral deflection of one or both of segments (1512, 1514) relative to shaft (1510); and or rotation of one or both of segments (1512, 1514) relative to shaft (1510). Alternatively, power may be communicated along one or more of wire sets (1530, 1532, 1534) to drive corresponding solenoids, motors, or other features to actively drive lateral deflection of one or both of segments (1512, 1514) relative to shaft (1510); and or rotation of one or both of segments (1512, 1514) relative to shaft (1510). One or more additional wires may also provide RF power (bipolar RF and/or monopolar RF) to end effector (1520). In addition, or in the alternative, one or more additional wires may also provide communication of electrical signals from one or more sensors in end effector (1520) and/or segments (1512, 1514).

Moreover, one or more additional wire sets, such as wiring assembly (1502) extends along shaft (1510) in the present example to provide voltage, electrical resistance, temperature, and/or other measurements of joints (1550, 1552) to the console or other processing module. Wiring assembly (1502) may include a power wire (1554) for sensors (1566, 1568) and a return path wire (1556). Wiring assembly (1502) may have intermediate connections positioned at each joint (1550, 1552), adjacent first articulating segment (1512) and second articulating segment (1514), in order to be able to monitor the voltage, electrical resistance, temperature, and/or other parameter(s) of the joint (1550, 1552). As shown, wiring assembly (1502), or alternatively, a flexible circuit, connects integrated sensors (1566, 1568) to monitor variances in the voltage, electrical resistance, temperature, and/or other parameter(s) of joints (1550, 1552).

As noted above, contamination by debris or fluid at joints (1550, 1552) may affect electrical communication properties (e.g., resistance, voltage, etc.) of electrical couplings at joints (1550, 1552). By monitoring the electrical communication properties (e.g., resistance, voltage, etc.) at joints (1550, 1552), the console or other processing module may provide real-time comparisons between monitored electrical communication property values and predetermined values or ranges; and provide an automated corrective action or other response in real time when a monitored electrical communication property value deviates from a predetermined value or range. Alternatively, the console or other processing module may provide any other suitable kind of response(s), examples of which are described in greater detail below. If the console or other processing module detects a voltage, electrical resistance, temperature, and/or other parameter change in one of the joints (1550, 1552), the console or other processing module may then decide whether the variance falls within a predetermined deviation range that would indicate a corrective action is warranted.

By way of example only, the above-described monitoring at joints (1550, 1552) may be used by the console or other processing module to control the electrical power provided to end effector (1520) based on the variations of voltage, electrical resistance, temperature, and/or other parameter(s) measured adjacent one or more of the joints (1550, 1552). In addition, or in the alternative, the console or other processing module may adapt the resistance provided via return path wire (1556) (e.g., to the resistance of power wire (1554)) to sufficiently bleed-off current to prevent damage to instrument (1500) due to inadvertent electrical short circuits. By monitoring the resistance and/or other electrical parameters at joints (1550, 1552) over time, the console or other processing module could adjust the maximum power limits send to end effector (1520) to prevent instrument (1500) from heating up or becoming damaged. In addition, the generator may selectively increase or decrease power as necessary, based on the above-described monitoring at joints (1550, 1552), to provide a constant or predictable thermal effect at end effector (1520).

In addition to monitoring electrical parameters at joints (1550, 1552), or as an alternative to monitoring electrical parameters at joints (1550, 1552), sensors (1566, 1568) may monitor temperature at joints (1550, 1552). By monitoring temperature at joints (1550, 1552), with or without monitoring of electrical parameters at joints (1550, 1552), the console or other processing module may further tune the delivery of power (e.g., bipolar RF, monopolar RF, etc.) to end effector (1520) without creating excessive heat at joint (1550, 1552) that might otherwise cause undesired tissue trauma or other undesired effects in the surgical field, adversely affect operability of instrument (1500), and/or damage one or more components of instrument (1500) at or near joint (1550, 1552). By way of example only, a generator may adjust the frequency or maximum duty cycle of the applied energy rather than merely adjusting the power level, in response to the monitored temperature of joint (1550, 1552) exceeding a predetermined threshold value.

While the foregoing examples are described in the context of contaminants reaching electrical connections via joints (1550, 1552) and having undesired electrical and/or thermal effects, the normal operation of instrument (1500) may also eventually create undesired electrical and/or thermal effects at electrical connections of joints (1550, 1552) (even in the absence of contaminants in joints (1550, 1552). For instance, communication of bipolar RF energy or monopolar RF energy through electrical connections (e.g., slip couplings, etc.) at joints (1550, 1552) may result in heating up of those electrical connections. Such heating may represent a power loss, such that the RF electrode(s) at end effector (1520) is/are not receiving the appropriate amount of power. In such scenarios, where sensors (1566, 1568) pick up on such heat-based losses, the console or other processing module may incrementally increase the level of power delivered from the generator, as needed based on the monitored parameters at joints (1550, 1552), to provide predictable and user-expected results on the tissue being engaged by end effector (1520). For instance, these results may include predictable and user-expected tissue sealing, ablation, etc.

While it may be appropriate to incrementally increase the level of power delivered from the generator to compensate for heat losses at joints (1550, 1552), the process may reach a point where this kind of response is no longer feasible. For instance, increasing the power level beyond a certain point may result in damage to instrument (1500), erratic or undesired tissue effects from end effector (1520), unreliable feedback from one or more sensors of instrument (1500), and/or other undesired effects. Thus, the console or other processing module may incrementally increase the level of power delivered from the generator as one or more monitored parameters at joints (1550, 1552) change through a certain range; but then provide a different kind of response once the one or more monitored parameters at joints (1550, 1552) exceed a predetermined threshold value. For instance, in the event that a monitored parameter at one or both of joints (1550, 1552) exceeds a predetermined threshold value (e.g., a maximum electrical resistance value, a maximum temperature value, etc.), the console or other processing module may provide a corrective action.

In some versions, the corrective action includes transitioning instrument (1500) into a "limp mode," which is an alternative mode of operation. By way of example only, a "limp mode" may allow some continued use of instrument (1500), though the console or other processing module may begin to decrease the power to keep the problematic joint (1550, 1552) under a maximum temperature (e.g., to prevent catastrophic failure of the problematic joint (1550, 1552), to prevent the problematic joint (1550, 1552) from burning tissue in the surgical field, etc.). Such a decrease in power may at least temporarily adversely affect the ability of end effector (1520) to impart desired RF effects on tissue. Thus, in the event that the console or other processing module determines that a "limp mode" or other alternative operation mode is warranted in view of a monitored parameter at one or both of joints (1550, 1552) exceeding a predetermined threshold value, the console or other processing module may provide the operator with an alert (e.g., audible, visual, tactile, etc.) to thereby notify the operator that the operation mode of instrument (1500) is changing. This may allow the operator to adjust their surgical technique accordingly, which may include deactivating RF power at least momentarily to allow the problematic joint (1550, 1552) to cool down. The operator may also wish to clean or replace instrument (1500) in response to receiving a "limp mode" alert.

In some versions, sensors (1566, 1568) of instrument (1500) may be configured to monitor the resistance or voltage over time of joints (1550, 1552) and to adjust the power signals or control responses based upon deviations beyond the expected range, as an effect from the outside voltage or potential, to create an offset for the power signal. As joints (1550, 1552) become contaminated, the resistance of electrical couplings within joints (1550, 1552) may change, as noted above. This may introduce electrical noise into the power signal or sensor signal(s); or in some instances, signal loss. If a local alternating load is introduced as a measure of the change of the overall system resistance, sensors (1566, 1568) could be adjusted to compensate for the presence of the contamination.

In some versions, instrument (1500) includes one or more operational parameter sensors (other than sensors (1566, 1568)) that is/are operable to sense various operational parameters associated with instrument (1500). Such operational parameters may include, but are not limited to, position or orientation information about one or more components of instrument (1500), electrical or thermal properties of tissue that is being engaged by end effector (1520), etc. Some merely illustrative examples of position or orientation sensors that may be included in a shaft assembly are described above in the context of shaft assembly (700) shown in FIG. 10 and shaft assembly (750) shown in FIG.

11. As another merely illustrative example, end effector (1520) may include electrodes for applying bipolar RF energy to tissue; and those same electrodes may be used as sensors to sense impedance in tissue that is being contacted by end effector (1520). Other ways in which operational parameter sensors may be integrated into a shaft assembly or end effector, and other operational parameters that may be sensed by such operational parameter sensors, will be apparent to those skilled in the art in view of the teachings herein. Contamination at joints (1550, 1552) may adversely affect the signals from such operational parameter sensors, such as by introducing noise to such signals or otherwise compromising the trustworthiness of the signals from such operational parameter sensors.

Regardless of the location or specific operational parameter(s) sensed by such an operational parameter sensor, a console or other processing module may vary its handling of signals from such an operational parameter sensor based at least in part on feedback from sensors (1566, 1568) indicating contamination at joints (1550, 1552) or other conditions that might adversely affect signals from operational parameter sensors. For instance, in the event that data from one or both of sensors (1566, 1568) indicates a value (e.g., voltage, resistance, etc.) exceeding a first threshold value, such that the signal from a primary operational parameter sensor is being somewhat affected, the console or other processing module may continue to factor in the signal from the affected primary operational parameter sensor as part of the control algorithm; but further rely on signals from one or more secondary operational parameter sensors to execute the control algorithm. In some such scenarios, the signals from the one or more secondary operational parameter sensors may be signals that the console or other processing module would typically not factor in as part of the control algorithm in the absence of the primary operational parameter sensor being affected; such that the signals from the one or more secondary operational parameter sensors are only being factored into the control algorithm because the signals from sensors (1566, 1568) indicate that the signal from the primary operational parameter sensor might be noisy or otherwise somewhat inaccurate. Thus, in this scenario, the affected primary operational parameter sensor may still influence the control algorithm, but the signal from the affected primary operational parameter sensor is now being supplemented by signals from one or more secondary operational parameter sensors.

In the event that data from one or both of sensors (1566, 1568) indicates a value (e.g., voltage, resistance, etc.) exceeding a second threshold value, such that the signal from a primary operational parameter sensor is being substantially affected, the console or other processing module may begin to disregard signals from the primary operational parameter sensor. In other words, the console or other processing module may pause adjustments to components (e.g., a generator, etc.) whose output would otherwise be adjusted in response to signals from the affected primary operational parameter sensor. Alternatively, in conditions where the console or other processing module has begun to disregard signals from the primary operational parameter sensor, the console or other processing module may again start relying on signals from one or more secondary operational parameter sensors to drive the control algorithm (i.e., as a substitute for the now-disregarded signal from the primary operational parameter sensor). The signals from the one or more secondary operational parameter sensors may thus serve as a proxy for the signal from the primary operational parameter sensor. In such scenarios, the one or more secondary operational parameter sensors may sense parameters that are related to, but different from, the parameter sensed by the primary operational parameter sensor. Alternatively, the console or other processing module may apply some other predetermined control algorithm to the outputs of components that would otherwise be adjusted based on signals from the affected operational parameter sensor.

In one merely illustrative example of an instrument having a primary operational parameter sensor and a secondary operational parameter sensor, the instrument includes an end effector with a sensor that senses density or other properties of tissue clamped between jaws of the end effector. This may serve as the primary operational parameter sensor. The electrical signal path between this primary operational parameter sensor in the end effector and a corresponding control module may include a rotary slip coupling in a distal portion of the shaft assembly of the instrument. The instrument may also include a translating knife member that severs tissue captured between the jaws of the end effector. The knife member may be driven by a motor. The control algorithm for the motor may factor in the density or other properties of tissue clamped between jaws of the end effector, such that the control algorithm factors in the signal from the primary operational parameter sensor in the end effector. In the event that a signal from a separate sensor that monitors parameter associated with the slip coupling (e.g., similar to sensors (1566, 1568)) indicates a value (e.g., voltage, resistance, etc.) exceeding a second threshold value, thereby indicating contamination of the slip coupling, and thereby indicating that the signal from the primary operational parameter sensor in the end effector is no longer necessarily reliable, the control module may turn to a secondary operational parameter sensor for a signal to either supplement the signal from the primary operational parameter sensor or substitute the signal from the primary operational parameter sensor. In this example, the secondary operational parameter sensor may include a motor current sensor that is operable to sense the current being used to drive the motor, which is driving the knife member. Since the movement of the knife member may vary based on the properties of the tissue clamped between the jaws of the end effector, the signal from the motor current sensor may serve as an adequate proxy for the signal from the primary operational parameter sensor in the end effector.

In the event that a control module begins to factor signals from a secondary operational parameter sensor into a control algorithm, as a supplement or substitute for signals from a primary operational parameter sensor, based on data from one or both of sensors (1566, 1568) indicating a value (e.g., voltage, resistance, etc.) exceeding a threshold value, such that the signal from a primary operational parameter sensor is being adversely affected, the console or other processing module may continue monitoring data from one or both of sensors (1566, 1568). In some such scenarios, the data from one or both of sensors (1566, 1568) may indicate that the corresponding monitored value (e.g., voltage, resistance, etc.) is no longer exceeding the threshold value, such that the signal from the primary operational parameter sensor is no longer being adversely affected. This may occur, for example, when a contaminant has been worked out of a joint (1550, 1552) during use of instrument (1500). If this occurs, then the control module may turn back to signals from the primary operational parameter sensor to drive the control algorithm; and may stop factoring signals from the one or more secondary operational parameter sensors into the control algorithm.

In some instances, the variation of electrical resistance at slip couplings in joints (1550, 1552) may also provide feedback indicating the level of torque that is being applied at joints (1550, 1552). As another merely illustrative alternative, the variation of electrical resistance at slip couplings in joints (1550, 1552) may also provide feedback indicating the angular positioning of components at joints (1550, 1552). For instance, in a version where a joint (1550, 1552) includes a slip coupling circular race that is terminated at one angle (e.g., 5 degrees), and then the resistance value drops off at a corresponding rotation angle (e.g., 175 degrees), then as the coupling is rotated the resistance within the track may change. This additional loss of resistance may be tracked over time and may be used to not only compensate for the loss and turn it off if it is too great; but also to determine what angle the slip coupling is with respect to the other side of the coupling.

Figure 25:
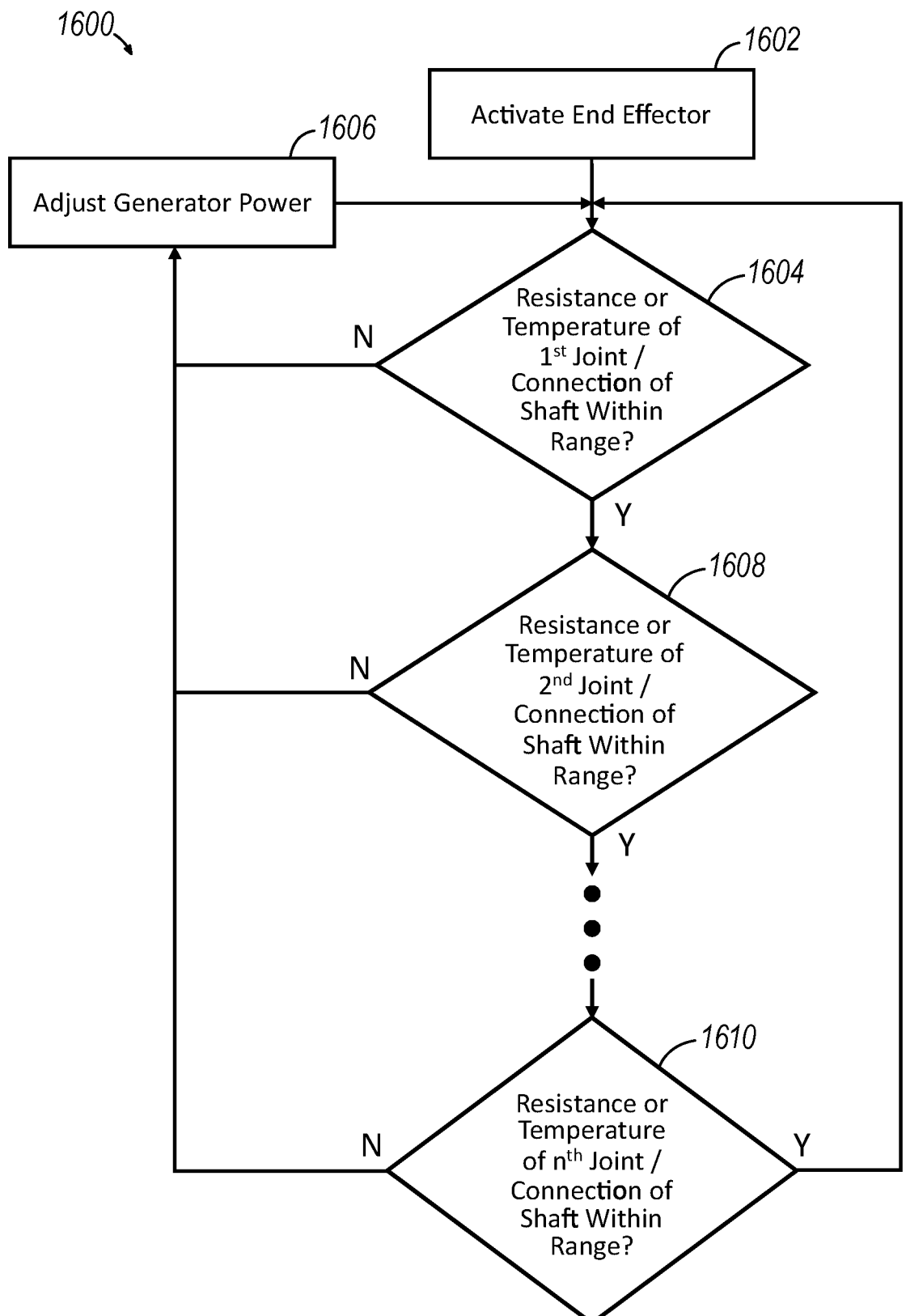
FIG. 25 depicts a flowchart of an exemplary method of monitoring characteristics of mechanical components of a surgical instrument that is operable to apply RF energy to tissue.

FIG. 25. depicts a flowchart of an exemplary method (1600) of monitoring temperature and resistance at couplings of a surgical instrument, as described above. While temperature and resistance are monitored in the present example, any other suitable parameters (e.g., voltage, etc.) may be monitored, in addition to or in lieu of monitoring temperature and/or resistance. At step (block 1602), the system or operator initiates the power output to the end effector from the power generator. During operation, at step (block 1604), sensors (1566, 1568) measure the resistance and temperature at one joint, such as one of joints (1550, 1552), and determines if the measured resistance and temperature variations from normal are within a predetermined range. If the resistance and temperature variations from normal are not within a predetermined range, the sensor transmits a signal back to the console; and at step (block 1606), the console adjusts the generator output power accordingly. Alternatively, in some versions, the console stores known normal resistance and temperature values and the sensor is configured to continuously measure and transmit measured resistance and temperature values to the console. In some such scenarios, the console makes the determination regarding whether the resistance and temperature variations from normal are within a predetermined range.

If the resistance and temperature variations from normal are within a predetermined range at step (block 1604), the method moves to the next one of joints (1550, 1552) to make the same measurement and determination at step (block 1608). If the resistance and temperature variations from normal are not within a predetermined range, the sensor transmits a signal back to the console; and again at step (block 1606), the console adjusts the generator output power accordingly. Thereafter, at step (block 1610), each additional joint is measured and the corrective action made according to the same method as the joints of steps (block 1604, block 1608).

IX. Example of Electrosurgical Instrument with Modular Component Contact Monitoring The following description relates to examples of different features that may be incorporated into any of the various surgical systems described above. Thus, the below-described features may be combined in various permutations as will be apparent to those skilled in the art in view of the teachings herein. Similarly, various ways in which the below-described features may be incorporated into any of the various surgical systems described above will be apparent to those skilled in the art in view of the teachings herein. It should be understood that the below-described features may be incorporated into robotically controlled surgical instruments and/or handheld surgical instruments.

As described above in the context of instrument (900) shown in FIG. 15, some instruments may include modular component interfaces, such as shaft interface assembly (920), with a plurality of electrical contacts that are positioned close to each other, such as electrical contacts (924). Such configurations may present a risk of signal cross talk, electrical shorting, or other signal interference from capacitive coupling currents or high voltages occurring across such closely positioned electrical contacts of modular component interfaces. In some scenarios, these issues may be due to a difficulty in providing complete fluid sealing near the electrical connectors and their associated contact arrays. Fluid present at electrical contact interfaces may attenuate transmitted signals or create electrical bridges between contacts that are not intended be bridged. It may therefore be desirable to protect or reinforce the electrical contacts of a modular shaft or end effector from capacitive coupling currents or high voltages; and/or to monitor the electrical contacts and take corrective actions if necessary.

Some instruments include features for protecting electrical connectors or modular components in surgical instruments. Examples of such devices and related concepts are disclosed in U.S. Pat. No. 10,090,616, entitled "Surgical Instrument Handle Assembly with Feature to Clean Electrical Contacts at Modular Shaft Interface," issued Oct. 2, 2018; U.S. Pat. No. 10,813,640, entitled "Method of Coating Slip Rings," issued Oct. 27, 2020; and U.S. Pat. No. 10,639,038, entitled "Staple Cartridge with Short Circuit Prevention Features," issued May 5, 2020, the disclosures of which are incorporated by reference herein, in their entirety. The components and configurations described below may be used in addition to, or in lieu of, the components and configurations described in those patent references.

Figure 26:
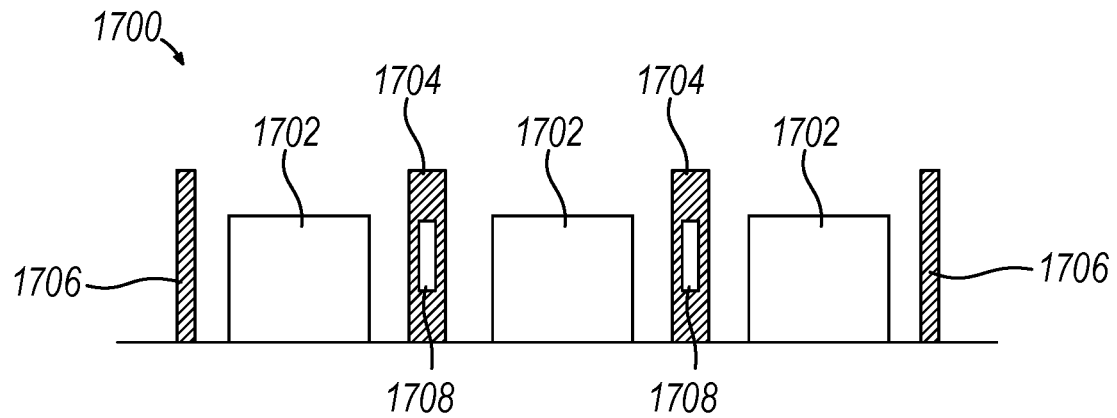
FIG. 26 depicts a schematic view of a first exemplary electrical contact array having a feature for protecting the electrical contacts.

FIG. 26 shows a first contact array (1700) that includes an array of electrical contacts (1702). By way of example only, electrical contacts (1702) may be provided in place of electrical contacts (924) (see, FIG. 15); and may be further configured to function similar to electrical contacts (924) except as described below. Electrical contacts (1702) may further be in electrical communication with a control circuit, power source, and/or various other electrical features within handle assembly (910) (see, FIG. 15) as will be apparent to those skilled in the art in view of the teachings herein.

As shown, contact array (1700) may be surrounded at least on one side, or from both sides of the modular connection, with a grounded, conductive shield (1706) that transfers any externally applied voltages to a return path thereby preventing externally applied voltages from reaching contacts (1702) and any electronics connected to contacts (1702). Shield (1706) is configured to receive a predefined sealing pressure, applied by a feature of handle interface assembly (960) during coupling, ensuring that the outer perimeter of the contact array (1700) is protected and that no gaps in shield (1706) could occur due to interferences or interactions between contact array (1700) and handle interface assembly (960). Therefore, shield (1706) is configured to divert voltage and current away from contacts (1702) and also seal contact array (1700) from invasion of fluids that might otherwise interfere with the electrical connection or result in electrical shorting. In an alternative configuration, rather than providing shield (1706) around contact array (1700), a conductive shield may be disposed around the entire modular connection of the shaft providing a means for the metallic shaft components to have a lower resistance return path connection generally around the modular connection instead of solely around contact array (1700), thereby shielding contacts (1702) from the metallic frame.

In addition to shield (1706), contact array (1700) may also include one or more features (1704) disposed between adjacent contacts (1702). Features (1704) may be formed of a non-conductive material, such as an elastomer, and may be configured to prevent an unwanted electrical bridge (i.e., a short circuit) from forming between two adjacent contacts (1702). More particularly, features (1704) may provide space between contacts (1702) and prevent electrical short circuits even if contact array (1700) is full of fluid, such as by providing a minimum resistance level that is an order of magnitude greater than the contact-to-contact resistance while contaminated with the fluid. In some versions, features (1704) may each include an elastomeric wiper or may be formed with a hydrophobic coating having a high dielectric breakdown and inherent resistance, such as providing a resistance of greater than or equal to 200 ohms between contacts (1702). The sizes and proportions of features (1704) may be configured relative to the proportions and sizes of the contacts (1702), proportionate to the current capacities or resistance of the two contacts (1702), or proportionate to the proximity of features (1704) to the electrical return path and the distance from the conductive shaft components. In some versions, each feature (1704) may be formed having a different size relative to other features (1704). In some versions, as will be described in greater detail below, features (1704) include active electronic controls or sensors (1708) to regulate the signal or power transferred through one or more contacts (1702) by measuring the signal or power via sensor (1708) and providing such measurements to the system console for continued monitoring.

Figure 27:
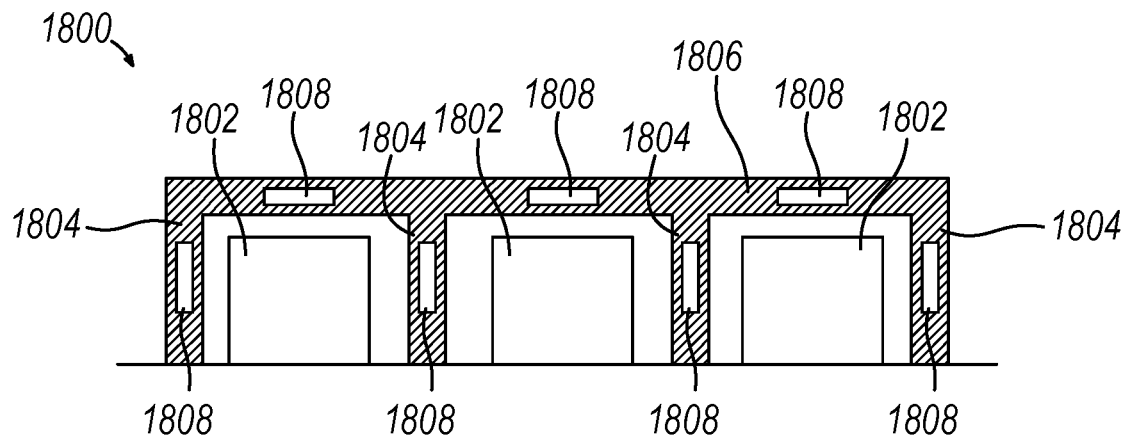
FIG. 27 depicts a schematic view of a second exemplary electrical contact array having a feature for protecting the electrical contacts.

FIG. 27 shows an alternative contact array (1800) for providing substantially the same functionality as contact array (1700) except as described below. Contact array (1800) includes one or more features (1804) disposed between adjacent contacts (1802). Features (1804) may be formed of a non-conductive material, such as an elastomer, and may be configured to prevent an unwanted electrical bridge (i.e., a short circuit) from forming between two adjacent contacts (1802). In some versions, features (1804) may each include an elastomeric wiper or may be formed with a hydrophobic coating having a high dielectric breakdown and inherent resistance. Particularly, features (1804) may be configured with an upper seal or gasket (1806) that spans across each contact (1802). Each contact (1802) is thus configured to be fully encapsulated, upon being electrically connected with the end effector or other modular component, so that no fluid is capable of flowing to or between any two contacts (1802). The encapsulation by features (1804) may nevertheless still allow contacts (1802) to make appropriate electrical contact with corresponding contacts (not shown) in handle interface assembly (960) of shaft assembly (950) when shaft assembly (950) is coupled with handle assembly (910). While not shown, encapsulating features (1804) and seal (1806) may further include a conductive shield disposed on an outer surface relative to contacts (1802), with the conductive shield being configured to transfer electrical voltages and currents to ground, similar to shield (1706) described above. In some versions, as will be described in greater detail below, features (1804) or seals (1806) include active electronic controls or sensors (1808) to regulate the signal or power transferred through one or more contacts (1802) by measuring the signal or power via sensor (1808) and providing such measurements to the system console for continued monitoring.

Figure 28:
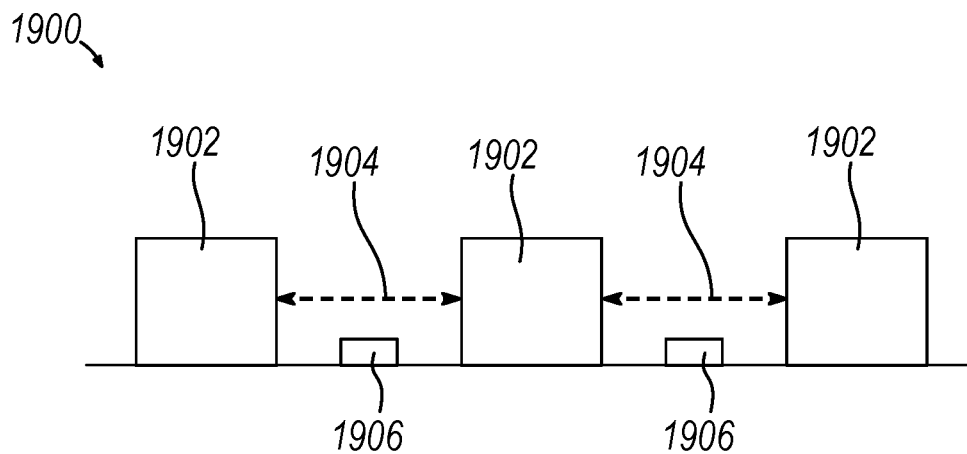
FIG. 28 depicts a schematic view of a third exemplary electrical contact array having a feature for protecting the electrical contacts.

FIG. 28 shows an alternative contact array (1900) for providing substantially the same functionality as contact arrays (1700, 1800) except as described below. Particularly, rather than including features disposed between or around contacts (1902), contacts (1902) may instead be adequately spaced apart to prevent electric voltages or bridges from forming between two contacts (1902). The proportions of the spaces (1904) between contacts (1902) may be configured relative to the proportions and sizes of the contacts (1902) and the voltages configured to transmit across contacts (1902). Alternatively, the proportions of the spaces (1904) between contacts (1902) may be proportionate to the current capacities or resistance of the two contacts (1902). Alternatively, the proportions of the spaces (1904) between contacts (1902) may be or proportionate to the proximity of contacts (1902) to the electrical return path and the distance from the conductive shaft components. In some versions, as will be described in greater detail below, spaces (1904) include active electronic controls or sensors (1906) to regulate the signal or power transferred through one or more contacts (1902) by measuring the signal or power via sensor (1906) and providing such measurements to the system console for continued monitoring.

In addition to the features described above for protecting contact arrays (1700, 1800, 1900), the signals on each contact array (1700, 1800, 1900) may also be actively measured by sensors (1708, 1808, 1906) during operation of the instrument to monitor for aberrant results, with signals indicative of the measurements being sent to the console for monitoring. For example, if a voltage condition above a predefined threshold is detected, the console could take active measures to prevent damage and propagation of the irregular voltage to adjacent contacts. The console may receive voltage or current measurements from each conductive path or trace defined by the contact array (1700, 1800, 1900) and react accordingly to initiate the corrective action. The console may be configured similar to console (20) described above with reference to FIG. 1, and may include a data processor configured and operable to initiate the corrective action, such as adjusting the power profile sent to the end effector. Further, the console may be a component of a robotic electrosurgical system, as described above. Various suitable forms that a console or other control module may take will be apparent to those skilled in the art in view of the teachings herein.

The console may be configured to take any of a plurality of corrective actions if an aberrant voltage or current is measured from a contact array (1700, 1800, 1900) or shield (1706). For example, the console may be configured to automatically apply active voltage clamps, adjust the power output to the end effector, or take other similar protective actions when electrical interference is detected. In some versions, the console may synchronize the voltage clamping with the activation signal for the instrument through a generator or hub interface. The console may also generate a trend line to adjust for the predictive error correction; and in some cases, deactivate RF power from end effector if the console determines that a voltage or current threshold may be reached on the impedance array.

By utilizing the features described above, the instrument may monitor electric potentials at various electrical contacts, slip couplings, or other electrical interface components; and adjust or compensate the power output to the end effector based on any detected losses. For example, the console may direct the generator to increase or decrease the power output; or apply one or more filters to the output signal. As described above, the signals on each contact array (1700, 1800, 1900)

or shield (1706) may be actively monitored for aberrant electrical activity to provide active operation data to the console to make such determinations and adjustments in real time.

X. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method for performing an electrosurgical procedure, comprising: (a) applying an active electrode to a patient, the active electrode being operatively coupled to a conductive body of a surgical instrument; (b) positioning first and second ground electrodes on the patient so as to create first and second current paths in tissue of the patient each respectively defined between the active electrode and the first and second ground electrodes, wherein the first ground electrode includes a first electrical lead coupled with an electrical ground node and the second ground electrode includes a second electrical lead coupled with the electrical ground node, the conductive body of the surgical instrument being coupled with each of the first and second electrical leads of the first and second ground electrodes; (c) imparting a first voltage to the active electrode so as to generate a therapeutic current in the first and second current paths, wherein the current in the first and second current paths alters a tissue of the patient; and (d) when a capacitive electrical current is induced on the conductive body of the surgical instrument as result of the imparting the first voltage to the active electrode, transferring a first portion of the capacitive electrical current from the conductive body to the first electrical lead and a second portion of the capacitive electrical current from the conductive body to the second electrical lead.

Example 2

The method of Example 1, wherein the first portion of the capacitive electrical current is up to approximately 30% of the second portion of the capacitive electrical current.

Example 3

The method of any one or more of Examples 1 through 2, further comprising: (a) coupling the conductive body, first electrical lead, and second electrical leads together to form an electrical junction; and (b) positioning a signal filter electrically between the first electrical lead and the second electrical lead.

Example 4

The method of Example 3, wherein the signal filter functions as a high-pass filter.

Example 5

The method of any one or more of Examples 3 through 4, further comprising: imparting a second voltage to the first ground electrode via the first electrical lead so as to generate a diagnostic current between the first ground electrode and the second ground electrode, wherein the signal filter prevents the diagnostic current from passing through the electrical junction.

Example 6

The method of Example 5, wherein the therapeutic current has a frequency of between approximately 300 kHz and approximately 500 kHz, and the diagnostic current has a frequency of approximately between approximately 15 kHz and approximately 15 kHz.

Example 7

The method of any one or more of Examples 1 through 6, further comprising: coupling the conductive body, first electrical lead, and second electrical leads to a transformer, wherein the transformer is operable to transfer the first portion of the capacitive electrical current from the conductive body to the first electrical lead and the second portion of the capacitive electrical current from the conductive body to the second electrical lead.

Example 8

An electrosurgical system, comprising: (a) an instrument, including: (i) a body, (ii) an end effector coupled with a distal end of the body, wherein the end effector includes an electrode operable to apply RF energy to tissue, and (iii) a conductive shield coupled with the body and including a ground return, wherein the conductive shield is configured to collect a capacitive coupling current that is induced by the application of the RF energy by the electrode; (b) a generator configured to provide the RF energy to the electrode; (c) a first ground pad having a first electrical lead, wherein the first electrical lead couples the first ground pad with the ground return of the conductive shield and the generator, wherein the ground return is configured to divert a first portion of the capacitive coupling current to the generator via the first electrical lead; and (d) a second ground pad having a second electrical lead, wherein the second electrical lead couples the second ground pad with the ground return of the conductive shield and the generator, wherein the ground return is configured to divert a second portion of the capacitive coupling current to the generator via the second electrical lead, wherein the first and second portions of the capacitive coupling current are substantially equal.

Example 9

The electrosurgical system of Example 8, wherein the RF energy has a frequency of between approximately 300 kHz and approximately 500 kHz.

Example 10

The electrosurgical system of any one or more of Examples 8 through 9, further comprising: (a) a conductive bridge configured to electrically couple the ground return, the first electrical lead, and the second electrical lead together; and (b) a signal filter electrically positioned between the first electrical lead and the second electrical lead.

Example 11

The electrosurgical system of Example 10, wherein the signal filter includes a high-pass filter.

Example 12

The electrosurgical system of any one or more of Examples 10 through 11, wherein the generator is configured to provide a diagnostic signal to the first ground pad via the first electrical lead, wherein the second ground pad is configured to return at least a portion of the diagnostic signal to the generator via the second electrical lead, wherein the signal filter is configured to prevent the diagnostic signal from passing through the conductive bridge.

Example 13

The electrosurgical system of Example 12, wherein the diagnostic signal has a frequency of between approximately 15 kHz and approximately 50 kHz.

Example 14

The electrosurgical system of any one or more of Examples 8 through 13, further comprising: a transformer configured to electrically couple between the ground return, the first electrical lead, and the second electrical lead, wherein the transformer is operable to transfer the first portion of the capacitive coupling current from the conductive shield to the first electrical lead and the second portion of the capacitive coupling current from the conductive shield to the second electrical lead.

Example 15

The electrosurgical system of any one or more of Examples 8 through 14, wherein the generator is configured to apply monopolar RF energy to a patient.

Example 16

The electrosurgical system of any one or more of Examples 8 through 15, wherein the generator is configured to provide an alternating diagnostic signals between the first and second ground pads via the first and second electrical leads, wherein the other ground pad of the first and second ground pads is configured to return at least a portion of the diagnostic signal to the generator.

Example 17

An electrosurgical system, comprising: (a) an instrument, including: (i) a body, (ii) an end effector coupled with a distal end of the body, wherein the end effector includes an electrode operable to apply RF energy to tissue, and (ii) a conductive shield coupled with the body and including a ground return, wherein the conductive shield is configured to collect a capacitive coupling current that is induced by the application of the RF energy by the electrode; (b) a first ground pad having a first electrical lead, wherein the first electrical lead couples the first ground pad with a ground source; (c) a second ground pad having a second electrical lead, wherein the second electrical lead couples the second ground pad with the ground source; and (d) a conductive bridge configured to electrically couple the ground return of the conductive shield, the first electrical lead, and the second electrical lead together, wherein the ground return is configured to divert a first portion of the capacitive coupling current to the ground source via the first electrical lead, wherein the ground return is configured to divert a second portion of the capacitive coupling current to the ground source via the second electrical lead, wherein the first and second portions of the capacitive coupling current are substantially equal.

Example 18

The electrosurgical system of Example 17, wherein the conductive bridge includes a signal filter electrically positioned between the first electrical lead and the second electrical lead.

Example 19

The electrosurgical system of Example 18, further comprising a generator configured to provide the RF energy, wherein the generator is configured to provide a diagnostic signal to the first ground pad via the first electrical lead, wherein the second ground pad is configured to return at least a portion of the diagnostic signal to the generator via the second electrical lead, wherein the signal filter prevents the diagnostic signal from passing through the conductive bridge.

Example 20

The electrosurgical system of any one or more of Examples 17 through 19, wherein the conductive bridge includes a transformer, wherein the transformer is operable to transfer the first portion of the capacitive coupling current from the conductive shield to the first electrical lead and the second portion of the capacitive coupling current from the conductive shield to the second electrical lead.

Example 21

A method for performing an electrosurgical procedure using an instrument system, wherein the instrument system includes (a) a surgical instrument having an electrode configured to operate on a tissue of a patient, (b) a generator for powering the electrode, and (c) one or more sensors configured to measure electrical energy flowing between the generator and the patient, the method comprising: (a) determining an electrical parameter threshold of capacitive coupling for monitoring on a conductive component of the surgical instrument during an operation; (b) activating the electrode of the surgical instrument by applying an output power signal from the generator to the electrode, wherein the output power signal has a first energy output profile; (c) monitoring an induced electrical parameter on the conductive component of the surgical instrument via the one or more sensors, the induced electrical parameter being associated with the determined electrical parameter threshold, wherein the induced electrical parameter includes a parasitic energy loss; and (d) when the induced electrical parameter measured from the conductive component of the surgical instrument meets or exceeds the electrical parameter threshold during the operation, adjusting the output power signal of the generator from the first energy output profile to a second energy output profile, wherein the adjustment is operable to reduce the induced electrical parameter measured from the conductive component of the surgical instrument, wherein the adjustment is further operable to reduce the parasitic energy loss without ceasing delivery of energy to the electrode.

Example 22

The method of Example 21, wherein the conductive component of the surgical instrument is configured to avoid coming into contact with the patient during the operation, the conductive component being separate from the electrode.

Example 23

The method of any one or more of Examples 21 through 22, wherein a first sensor of the one or more sensors is configured to measure electrical energy communicated from the generator to the patient, wherein a second sensor of the one or more sensors is configured to measure electrical energy communicated from the patient to the generator, wherein the instrument system is configured to measure an impedance of the patient between the first and second sensors, the method further comprising: (a) determining an impedance change threshold for monitoring during an operation; (b) monitoring for a change in the impedance of the patient between the first and second sensors; and (c) when the change of the impedance of the patient meets or exceeds the impedance change threshold during the operation, adjusting the output power signal of the generator from the first energy output profile to the second energy output profile.

Example 24

The method of any one or more of Examples 21 through 23, wherein adjusting the output power signal includes adjusting at least one of a voltage magnitude, a current limit, or a power limit.

Example 25

The method of any one or more of Examples 21 through 24, further comprising: (a) upon adjusting the output power signal from the first energy output profile to the second energy output profile, determining whether the generator has reached a power output adjustment limit and is thereby incapable of adjusting the output power signal from the first energy output profile to the second energy output profile; and (b) if the generator has reached the power adjustment limit, disconnecting the output power signal from the electrode.

Example 26

The method of any one or more of Examples 21 through 25, wherein the conductive component of the surgical instrument includes a metallic shield.

Example 27

The method of any one or more of Examples 21 through 26, further comprising: (a) prior to activating the electrode of the surgical instrument, positioning a ground electrode on the patient so as to create a current path in the tissue of the patient between the electrode and the ground electrode, wherein the ground electrode includes an electrical lead coupled with an electrical ground node.

Example 28

The method of any one or more of Examples 21 through 27, wherein the generator is configured to apply monopolar RF energy to the patient.

Example 29

The method of any one or more of Examples 21 through 28, wherein the surgical instrument is a handheld instrument.

Example 30

The method of any one or more of Examples 21 through 29, wherein the surgical instrument is a component of a robotic electrosurgical system.

Example 31

The method of any one or more of Examples 21 through 30, wherein the instrument system further includes a tuner coupled with the generator, wherein the tuner is selectively operable to adjust the output power signal of the generator, wherein adjusting the output power signal of the generator from the first energy output profile to a second energy output profile includes: (a) operating the tuner to thereby adjust the output power signal of the generator from the first energy output profile to a second energy output profile.

Example 32

The method of any one or more of Examples 21 through 31, wherein the electrical parameter threshold includes an electrical current threshold.

Example 33

The method of any one or more of Examples 21 through 32, wherein the induced electrical parameter includes an induced electrical current.

Example 34

The method of any one or more of Examples 21 through 33, wherein the first energy output profile provides a first voltage, wherein the second energy output profile provides a second voltage, wherein the second voltage is lower than the first voltage.

Example 35

The method of Example 34, wherein the wherein the first energy output profile provides a first power level, wherein the second energy output profile provides a second power level, wherein the second power level is the same as the first power level.

Example 36

An electrosurgical system, comprising: (a) an instrument, including: (i) a body, (ii) an end effector coupled with a distal end of the body, wherein the end effector includes an electrode operable to apply RF energy to tissue of a patient, and (ii) a conductive component coupled with the body, wherein the conductive component is configured to collect a capacitive coupling current that is induced by application of the RF energy by the electrode; (b) a generator configured to provide the RF energy to the electrode; and (c) a controller operatively coupled with the generator and configured to (i) determine a current threshold of capacitive coupling for monitoring on the conductive component during an operation, (ii) activate the electrode of the instrument by applying an output power signal to the electrode from the generator, (iii) monitor an induced current on the conductive component of the instrument, wherein the induced current includes a parasitic energy loss originating from the electrode, and (iv) when the induced current meets or exceeds the current threshold during the operation, adjust the output power signal of the generator to reduce the induced current until the induced current falls below the current threshold of capacitive coupling while maintaining delivery of energy to the electrode.

Example 37

The electrosurgical system of Example 36, further comprising a tuner coupled with the generator, wherein the controller is configured to selectively operate the tuner to adjust the output power signal of the generator.

Example 38

The electrosurgical system of any one or more of Examples 36 through 37, further comprising one or more sensors operatively coupled with the controller and configured to measure the capacitive coupling current and provide a current measurement to the controller.

Example 39

The electrosurgical system of Example 38, wherein at least one of the one or more sensors is configured to measure an impedance value, wherein the controller is further configured to: (i) determine an impedance change threshold for monitoring during an operation, (ii) monitor for a change in the impedance value, and (iii) when the change of the impedance value meets or exceeds the impedance change threshold during the operation, adjust the output power signal of the generator.

Example 40

The electrosurgical system of any one or more of Examples 36 through 39, wherein, to adjust the output power signal, the controller is configured to adjust at least one of a voltage magnitude, a current limit, or an power limit.

Example 41

The electrosurgical system of Example 36, wherein the generator is configured to apply monopolar RF energy to a patient.

Example 42

The electrosurgical system of Example 41, wherein the monopolar RF energy has a frequency of between approximately 300 kHz and approximately 500 kHz.

Example 43

An electrosurgical system, comprising: (a) an instrument, including: (i) a body, (ii) an end effector coupled with a distal end of the body, wherein the end effector includes an electrode operable to apply RF energy to tissue of a patient, and (ii) a conductive component coupled with the body, wherein the conductive component is configured to collect a capacitive coupling current that is induced by application of the RF energy by the electrode; (b) a generator configured to provide the RF energy sufficient to cut or seal tissue to the electrode; (c) a sensor configured to measure the capacitive coupling current; and (d) a controller operatively coupled with the generator and the sensor and configured to: (i) determine a current threshold of capacitive coupling for monitoring on the conductive component during an operation, (ii) monitor an induced current on the conductive component of the instrument, and (iii) when the induced current meets or exceeds the current threshold during the operation, adjust the RF energy provided by the generator to reduce the induced current until the induced current falls below the current threshold of capacitive coupling while maintaining delivery of energy to the electrode.

Example 44

A surgical system, comprising: (a) a first instrument having a first end effector, wherein the first end effector is operable to apply a first type of energy to tissue of a patient; (b) a second instrument having a second end effector, wherein the second end effector is operable to apply a second type of energy to tissue of a patient; (c) one or more electric power generators configured to generate first and second energy signals, wherein the one or more electric power generators include: (i) a first generator output configured to transmit the first energy signal to the first end effector, wherein the first energy signal is operable to power the first end effector to apply the first type of energy to tissue of a patient, and (ii) a second generator output configured to transmit the second energy signal to the second end effector, wherein the second energy signal is operable to power the second end effector to apply the second type of energy to tissue of a patient; and (d) a power monitor operatively coupled with the one or more electric power generators, wherein the power monitor is configured to monitor a first energy parameter of the first energy signal and transmit the first energy parameter to the one or more electric power generators, wherein the one or more electric power generators is configured to adjust a second energy parameter of the second energy signal, based at least in part on the transmitted first energy parameter, to avoid interactions between the first energy signal and the second energy signal.

Example 45

The surgical system of Example 44, wherein the one or more electric generators are configured to generate the first and second energy signals simultaneously.

Example 46

The surgical system of any one or more of Examples 44 through 45, wherein first and second energy parameters each include at least one of electrical current, voltage, frequency, or wave shape.

Example 47

The surgical system of any one or more of Examples 44 through 46, wherein the first and second end effectors include at least one of a monopolar RF electrode, bipolar RF electrodes, or an ultrasonic blade.

Example 48

The surgical system of any one or more of Examples 44 through 47, further comprising one or more power sensors operatively coupled with the power monitor, wherein the one or more power sensors are configured to measure the first energy parameter and transmit the measurement to the power monitor.

Example 49

The surgical system of Example 48, wherein one or more power sensors includes at least one of an RF power sensor or an ultrasonic transducer.

Example 50

The surgical system of any one or more of Examples 48 through 49, wherein the first instrument includes a monopolar RF instrument with a conductive component, wherein the conductive component is configured to collect a capacitive coupling current that is induced by application of the first energy signal to the first end effector, wherein the one or more power sensors is configured to measure the capacitive coupling current and provide a current measurement to the power monitor.

Example 51

The surgical system of Example 50, wherein the power monitor is configured to transmit the current measurement to the one or more electric power generators, wherein the one or more electric power generators is configured to adjust a time constant parameter of the second energy signal.

Example 52

The surgical system of any one or more of Examples 44 through 51, wherein the first and second instruments are each handheld surgical instruments.

Example 53

The surgical system of any one or more of Examples 44 through 52, wherein the first and second instruments are each components of a robotic electrosurgical system.

Example 54

The surgical system of any one or more of Examples 44 through 53, the one or more electric power generators including a first power generator and a second power generator, the first generator output being part of the first power generator, the second power output being part of the second power generator.

Example 55

The surgical system of any one or more of Examples 44 through 54, the first type of energy including electrosurgical energy.

Example 56

The surgical system of Example 55, the first type of energy including monopolar RF electrosurgical energy, the second type of energy including bipolar RF electrosurgical energy.

Example 57

The surgical system of any one or more of Examples 55 through 56, further comprising a ground pad, the ground pad being configured to contact skin of a patient, the ground pad being further configured to couple with the one or more electric power generator to thereby provide a ground return path.

Example 58

The surgical system of any one or more of Examples 44 through 57, the second energy parameter including a frequency based energy parameter.

Example 59

A surgical system, comprising: (a) a first instrument having a first end effector, wherein the first end effector is operable to apply a first type of energy to tissue of a patient; (b) a second instrument having a second end effector, wherein the second end effector is operable to apply a second type of energy to tissue of a patient; (c) a first generator configured to generate a first energy signal and to transmit the first energy signal to the first end effector, wherein the first energy signal is operable to power the first end effector, and (d) a second generator configured to generate a second energy signal and to transmit the second energy signal to the second end effector, wherein the second energy signal is operable to power the second end effector, and (e) a power monitor operatively coupled with the first and generators, wherein the power monitor is configured to monitor the first energy signal of the first generator and transmit a corresponding measurement signal to the second generator, wherein the second generator is configured to adjust an energy parameter of the second energy signal in response to receiving the transmitted measurement signal.

Example 60

The surgical system of Example 59, wherein the second generator is configured to adjust the energy parameter to distinguish the energy parameter of the second energy signal from a corresponding energy parameter of the first energy signal, based at least in part on the transmitted measurement signal, to avoid interactions between the first energy signal and the second energy signal.

Example 61

The surgical system of any one or more of Examples 59 through 60, wherein the power monitor is configured to monitor one or more of an electrical current, voltage, frequency, or wave shape of the first energy signal of the first generator, wherein the transmitted measurement signal is associated with the monitored one or more of electrical current, voltage, frequency, or wave shape of the first energy signal.

Example 62

The surgical system of any one or more of Examples 59 through 61, wherein the first and second generators are configured to generate the first and second energy signals simultaneously.

Example 63

The surgical system of any one or more of Examples 59 through 62, wherein the first and second end effectors each include at least one of a monopolar RF electrode, bipolar RF electrodes, or an ultrasonic blade.

Example 64

The surgical system of any one or more of Examples 59 through 63, further comprising one or more sensors operatively coupled with the power monitor, wherein the one or more sensors are configured to measure the one or more corresponding energy parameters of the first energy signal of the first generator.

Example 65

The surgical system of Example 64, wherein one or more sensors includes at least one of an RF power sensor or an ultrasonic transducer.

Example 66

The surgical system of any one or more of Examples 59 through 65, wherein the first instrument includes a monopolar RF instrument having a conductive component, wherein the conductive component is configured to collect a capacitive coupling current that is induced by application of the first energy signal to the first end effector, the system further comprising one or more sensors configured to measure the capacitive coupling current and provide a current measurement to the power monitor.

Example 67

The surgical system of Example 66, wherein the power monitor is configured to transmit the current measurement to the second generator, wherein the second generator is configured to adjust a time constant parameter of the second energy signal.

Example 68

A method for performing an electrosurgical procedure, comprising: (a) generating a first energy signal having a first frequency for powering a first end effector of a surgical instrument, wherein the first end effector applies a first type of energy to tissue of a patient; (b) generating a second energy signal having a second frequency for simultaneously powering a second end effector of a surgical instrument, wherein the second end effector applies a second type of energy to tissue of the patient; (c) measuring the first frequency of the first energy signal; (d) based upon the measurement of the frequency of the first energy signal, adjusting the second frequency of the second energy signal to distinguish the second frequency from the first frequency so as to prevent the second energy signal from interacting with the first energy signal Example 69

A surgical instrument, comprising: (a) a shaft assembly having a plurality of conductive components; (b) an end effector positioned at a distal end of the shaft assembly, wherein the end effector is operable to apply energy to tissue of a patient; (c) a console operable to power the end effector; (d) a conductor assembly disposed within the shaft assembly and configured to transfer power from the console to the end effector, wherein the conductor assembly includes a ground return path; and (e) a plurality of voltage sensors, wherein each conductive component of the plurality of conductive components is configured to couple with a corresponding voltage sensor of the plurality of voltage sensors and with the ground return path, wherein the plurality of voltage sensors are operable to measure a voltage potential difference of the coupled conductive component relative to a ground potential defined by the ground return path; wherein the console is configured to: (i) determine whether the measured voltage potential difference exceeds a maximum threshold value, and (ii) when the measured voltage potential difference exceeds the maximum threshold value, initiate a corrective action.

Example 70

The surgical instrument of Example 69, wherein each conductive component of the plurality of conductive components is configured with a floating voltage.

Example 71

The surgical instrument of any one or more of Examples 69 through 70, wherein the shaft assembly or the end effector further comprises an operation sensor operable to sense a parameter associated with operation of the end effector, wherein the corrective action includes adjusting an electrical noise correction threshold associated with the operation sensor.

Example 72

The surgical instrument of any one or more of Examples 69 through 71, wherein the shaft assembly or the end effector further comprises an operation sensor operable to sense a parameter associated with operation of the end effector, wherein the corrective action includes adjusting a voltage transformation associated with the operation sensor.

Example 73

The surgical instrument of any one or more of Examples 69 through 72, wherein the shaft assembly or the end effector further comprises an operation sensor operable to sense a parameter associated with operation of the end effector, wherein the corrective action includes disregarding a signal from the operation sensor.

Example 74

The surgical instrument of any one or more of Examples 69 through 73, wherein the shaft assembly or the end effector further comprises an operation sensor operable to sense a parameter associated with operation of the end effector, wherein the corrective action includes disconnecting power to the operation sensor.

Example 75

The surgical instrument of any one or more of Examples 69 through 74, wherein the shaft assembly or the end effector further comprises an operation sensor operable to sense a parameter associated with operation of the end effector, the corrective action includes rebooting the operation sensor.

Example 76

The surgical instrument of any one or more of Examples 69 through 75, wherein the corrective action includes discharging a selected conductive component of the plurality of conductive components to the ground return path.

Example 77

The surgical instrument of Example 76, wherein the corrective action further includes deactivating sensing from the voltage sensor associated with the a selected conductive component while the voltage is being discharged.

Example 78

The surgical instrument of any one or more of Examples 69 through 77, wherein each of the plurality of conductive components is configurable to be electrically interconnected, wherein each of the plurality of conductive components shares a common voltage potential upon being electrically interconnected.

Example 79

The surgical instrument of Example 78, wherein the console is operable to reduce the common voltage potential relative to the ground potential from the plurality of conductive components while the plurality of conductive components are electrically interconnected.

Example 80

The surgical instrument of any one or more of Examples 69 through 79, wherein the plurality of voltage sensors comprise high impedance voltage sensors.

Example 81

The surgical instrument of any one or more of Examples 69 through 80, wherein the console includes a generator configured to provide RF energy to the end effector.

Example 82

The surgical instrument of any one or more of Examples 69 through 81, wherein the conductor assembly comprises a wiring harness.

Example 83

The surgical instrument of any one or more of Examples 69 through 82, wherein the console is a component of a robotic electrosurgical system.

Example 84

A surgical instrument, comprising: (a) a shaft assembly having a plurality of conductive components, wherein each conductive component of the plurality of conductive components is configured with a floating voltage; (b) an end effector positioned at a distal end of the shaft assembly, wherein the end effector is operable to apply energy to tissue of a patient; (c) a console operable to power the end effector; (d) a conductor assembly disposed within the shaft assembly and configured to transfer power from the console to the end effector, wherein the conductor assembly includes a ground return path; and (e) a plurality of voltage sensors, wherein each conductive component of the plurality of conductive components is configured to couple with a corresponding voltage sensor of the plurality of voltage sensors and with the ground return path, wherein the plurality of voltage sensors are operable to measure a voltage potential difference of the coupled conductive component relative to a ground potential defined by the ground return path; wherein the console is configured to initiate a corrective action based on the measured voltage potential difference.

Example 85

The surgical instrument of Example 84, further comprising an operation sensor operable to sense a parameter associated with operation of the end effector, wherein the corrective action includes adjusting an electrical noise correction threshold associated with the operation sensor.

Example 86

The surgical instrument of any one or more of Examples 84 through 85, further comprising an operation sensor operable to sense a parameter associated with operation of the end effector, wherein the corrective action includes adjusting a voltage transformation associated with the operation sensor.

Example 87

The surgical instrument of any one or more of Examples 84 through 86, wherein each of the plurality of conductive components is configurable to be electrically interconnected, wherein the corrective action includes electrically interconnecting the plurality of conductive components, wherein each of the plurality of conductive components shares a common voltage potential upon being electrically interconnected.

Example 88

A surgical instrument, comprising: (a) a shaft assembly having a conductive component configured with a floating voltage; (b) an end effector positioned at a distal end of the shaft assembly, wherein the end effector is operable to apply energy to tissue of a patient; (c) a console operable to power the end effector; (d) a conductor assembly disposed within the shaft assembly and configured to transfer power from the console to the end effector, wherein the conductor assembly includes a ground return path; and (e) a voltage sensor, wherein the conductive component of the shaft assembly is configured to couple with the voltage sensor and with the ground return path, wherein the voltage sensor is operable to measure a voltage potential difference of the conductive component relative to a ground potential defined by the ground return path; wherein the console is configured to: (i) determine whether the measured voltage potential difference exceeds a maximum threshold value, and (ii) when the measured voltage potential difference exceeds the maximum threshold value, initiate a corrective action.

Example 89

An apparatus, comprising: (a) a shaft assembly, the shaft assembly including: (i) a first shaft component, (ii) a second shaft component, (iii) a joint joining the first shaft component with the second shaft component, the second shaft component being movable relative to the first shaft component at the joint, and (iv) a sliding electrical coupling at the joint, the sliding electrical coupling being configured to provide electrical continuity between the first and second shaft components while permitting movement of the second shaft component relative to the first shaft component at the joint; (b) an end effector positioned at a distal end of the shaft assembly, wherein the end effector is operable to engage tissue of a patient; (c) a control module operable to power the end effector; (d) a first sensor positioned adjacent to the joint, wherein the first sensor is configured to: (i) measure a joint parameter indicating a state of the sliding electrical coupling, and (ii) transmit a first signal indicative of the measured joint parameter to the control module; wherein the control module is configured to: (i) determine whether the measured joint parameter exceeds a maximum deviation from a predetermined value, and (ii) when the measured joint parameter exceeds a maximum deviation from a predetermined value, initiate a first responsive action.

Example 90

The apparatus of Example 89, wherein the shaft assembly defines a longitudinal axis, wherein the second shaft component is rotatable relative to the first shaft component about the longitudinal axis at the joint.

Example 91

The apparatus of any one or more of Examples 89 through 90, wherein the first responsive action includes increasing a power signal provided by the control module to the end effector.

Example 92

The apparatus of any one or more of Examples 89 through 91, wherein the first responsive action includes decreasing a power signal provided by the control module to the end effector.

Example 93

The apparatus of any one or more of Examples 89 through 92, further comprising a second sensor, the second sensor being operable to: (i) measure a first operational parameter associated with operation of the end effector, and (ii) transmit a second signal indicative of the measured first operational parameter to the control module, wherein the control module is configured to execute a control algorithm based at least in part on the second signal.

Example 94

The apparatus of Example 93, wherein the first responsive action includes adjusting a signal processing magnitude of the second signal transmitted by the second sensor while executing the control algorithm.

Example 95

The apparatus of any one or more of Examples 93 through 94, further comprising a third sensor, the third sensor being operable to: (i) measure a second operational parameter associated with operation of the end effector, and (ii) transmit a third signal indicative of the measured second operational parameter to the control module, wherein the first responsive action includes supplementing the second signal with the third signal while executing the control algorithm.

Example 96

The apparatus of any one or more of Examples 93 through 94, further comprising a third sensor, the third sensor being operable to: (i) measure a second operational parameter associated with operation of the end effector, and (ii) transmit a third signal indicative of the measured second operational parameter to the control module, wherein the first responsive action includes substituting the second signal with the third signal while executing the control algorithm.

Example 97

The apparatus of any one or more of Examples 89 through 94, further comprising a third sensor, the third sensor being operable to: (i) measure a second operational parameter associated with operation of the end effector, and (ii) transmit a third signal indicative of the measured second operational parameter to the control module, wherein the control module is configured to disregard the third signal while executing the control algorithm when the measured joint parameter does not exceed the maximum deviation from a predetermined value.

Example 98

The apparatus of any one or more of Examples 89 through 97, the joint parameter indicating an electrical resistance of the sliding electrical coupling.

Example 99

The apparatus of Example 98, the predetermined value being an electrical resistance value associated with a predetermined maximum temperature value.

Example 100

The apparatus of any one or more of Examples 89 through 99, the joint parameter indicating a voltage of the sliding electrical coupling.

Example 101

The apparatus of any one or more of Examples 89 through 100, the joint parameter indicating a temperature of the sliding electrical coupling.

Example 102

The apparatus of any one or more of Examples 89 through 101, further comprising an orientation sensor configured to sense a change of orientation at the joint, wherein the control module is configured to correlate a change of orientation as sensed by the orientation sensor with the measured joint parameter and determine whether to initiate an alternative operation mode.

Example 103

The apparatus of Example 102, wherein the alternative operation mode includes configuring the control module to vary the power to the end effector based upon change of orientation at the joint.

Example 104

The apparatus of any one or more of Examples 89 through 103, wherein the first responsive action includes adjusting a maximum power limit of end effector.

Example 105

The apparatus of any one or more of Examples 89 through 104, wherein the end effector is operable to apply RF energy to tissue.

Example 106

The apparatus of any one or more of Examples 89 through 105, wherein the control module is a component of a robotic electrosurgical system.

Example 107

An apparatus, comprising: (a) a shaft assembly, the shaft assembly including: (i) a first shaft component, (ii) a second shaft component, the first and second shaft components together defining a longitudinal axis, (iii) a rotary joint joining the first shaft component with the second shaft component, the second shaft component being rotatable relative to the first shaft component about the longitudinal axis at the rotary joint, and (iv) a sliding electrical coupling at the rotary joint, the sliding electrical coupling being configured to provide electrical continuity between the first and second shaft components while permitting rotation of the second shaft component relative to the first shaft component at the rotary joint; (b) an end effector positioned at a distal end of the shaft assembly, wherein the end effector is operable to engage tissue of a patient; (c) a control module operable to power the end effector; (d) a sensor positioned adjacent to the rotary joint, wherein the sensor is configured to: (i) measure a joint parameter indicating one or more of an electrical resistance of the sliding electrical coupling, a voltage of the sliding electrical coupling, or a temperature of the sliding electrical coupling, and (ii) transmit a signal indicative of the measured joint parameter to the control module; wherein the control module is configured to: (i) determine whether the measured joint parameter exceeds a maximum deviation from a predetermined value, and (ii) when the measured joint parameter exceeds a maximum deviation from a predetermined value, initiate a responsive action.

Example 108

A method of operating a surgical instrument, wherein the surgical instrument includes shaft assembly having first and second shaft components coupled together at a joint, an end effector positioned at a distal end of the shaft assembly, a control module operable to power the end effector, and a sensor positioned adjacent the joint, the method comprising: (a) providing a power signal from the control module to the end effector; (b) measuring, by the sensor, an electrical or thermal parameter at the joint; (c) transmitting a signal indicative of the measured electrical or thermal parameter to the control module; (d) determining, by the control module, whether the electrical or thermal parameter exceeds a maximum deviation from a predetermined electrical or thermal parameter value; and (e) when the electrical or thermal parameter exceeds the maximum deviation from the predetermined electrical or thermal parameter value, adjusting the power signal provided from the control module to the end effector.

Example 109

An apparatus, comprising: (a) a shaft assembly; (b) an end effector positioned at a distal end of the shaft assembly, wherein the end effector is operable to engage tissue of a patient; (c) a control module configured to generate a power output to power the end effector; (d) a first electrical connector operatively coupled with the control module, wherein the first electrical connector includes a first plurality of electrical contacts, wherein at least one electrical contact of the first plurality of electrical contacts is configured to transfer the power output to a second plurality of electrical contacts of a second electrical connector while the first and second electrical connectors are coupled; and (e) a plurality of nonconductive structures disposed adjacent each of the plurality of first electrical contacts, wherein the plurality of nonconductive structures are configured to prevent a signal interference between each electrical contact of the first plurality of electrical contacts.

Example 110

The apparatus of Example 109, wherein the plurality of nonconductive structures each includes a sensor, wherein each sensor is configured to measure an electrical signal of an adjacent electrical contact.

Example 111

The apparatus of Example 110, wherein the sensor is configured transmit the measurement of the electrical signal to the control module.

Example 112

The apparatus of Example 3, wherein the control module is configured to: (i) determine whether the electrical signal exceeds a voltage threshold or a current threshold, and (ii) when the electrical signal exceeds a voltage threshold or a current threshold, initiate a corrective action.

Example 113

The apparatus of Example 112, wherein the corrective action includes adjusting the power output.

Example 114

The apparatus of any one or more of Examples 109 through 5, wherein each nonconductive structure of the plurality of nonconductive structures is disposed between two electrical contacts of the first plurality of electrical contacts.

Example 115

The apparatus of any one or more of Examples 109 through 114, wherein each nonconductive structure of the plurality of nonconductive structures is proportionately sized based upon a proximity of the nonconductive structure between the corresponding two electrical contacts of the first plurality of electrical contacts.

Example 116

The apparatus of any one or more of Examples 109 through 115, wherein each nonconductive structure of the plurality of nonconductive structures is proportionately sized based upon a proximity of the nonconductive structure to an electrical ground defined by the power output and upon a proximity of the nonconductive structure to a conductive component of the shaft assembly.

Example 117

The apparatus of Example 116, wherein two nonconductive structures of the plurality of nonconductive structures have sizes that differ from each other.

Example 118

The apparatus of any one or more of Examples 109 through 117, wherein each nonconductive structure of the plurality of nonconductive structures is proportionately sized based upon electrical current capacities of two adjacent electrical contacts of the first plurality of electrical contacts.

Example 119

The apparatus of any one or more of Examples 109 through 118, wherein each nonconductive structure of the plurality of nonconductive structures is proportionately sized based upon an electrical resistance between two adjacent electrical contacts of the first plurality of electrical contacts.

Example 120

The apparatus of any one or more of Examples 109 through 119, wherein each nonconductive structure of the plurality of nonconductive structures provides a resistance of greater than 200 ohms between two adjacent electrical contacts of the first plurality of electrical contacts.

Example 121

The apparatus of any one or more of Examples 109 through 120, wherein the plurality of nonconductive structures are configured to encapsulate each electrical contact of the first plurality of electrical contacts to form a fluid-tight seal.

Example 122

The apparatus of any one or more of Examples 109 through 121, wherein the end effector is operable to receive and apply monopolar RF energy sufficient to cut or seal tissue.

Example 123

The apparatus of any one or more of Examples 109 through 122, wherein the control module is a component of a robotic electrosurgical system.

Example 124

A surgical instrument, comprising: (a) a shaft assembly; (b) an end effector positioned at a distal end of the shaft assembly, wherein the end effector is operable to apply energy to tissue of a patient; (c) a first electrical connector configured to couple with a control module, wherein the first electrical connector includes a first plurality of electrical contacts; (d) a second electrical connector having a second plurality of electrical contacts configured to mate with the first plurality of electrical contacts to form a plurality of conductive bridges, wherein at least one electrical contact of the first plurality of electrical contacts is configured to transfer a power signal to at least one corresponding electrical contact of the second plurality of electrical contacts while the first and second electrical connectors are coupled; and (e) a plurality of nonconductive structures disposed adjacent each electrical bridge of the plurality of electrical bridges, wherein the plurality of nonconductive structures are configured to prevent interference of the power signal between the first plurality of electrical bridges.

Example 125

The apparatus of Example 124, further comprising a body, the shaft assembly being configured to removably couple with the body, the first electrical connector being incorporated into the body, the second electrical connector being incorporated into the shaft assembly.

Example 126

The apparatus of any one or more of Examples 124 through 125, further comprising a conductive shield surrounding the first plurality of electrical contacts, the conductive shield being coupled with ground.

Example 127

The apparatus of Example 126, the conductive shield being further configured to provide a fluid tight seal around the first and second pluralities of electrical contacts while the first and second electrical connectors are coupled.

Example 128

A surgical instrument, comprising: (a) a shaft assembly; (b) an end effector positioned at a distal end of the shaft assembly, wherein the end effector is operable to engage tissue of a patient; (c) a first electrical connector including a first plurality of electrical contacts; and (d) a second electrical connector having a second plurality of electrical contacts configured to mate with the first plurality of electrical contacts to form a plurality of conductive bridges, wherein at least one electrical contact of the first plurality of electrical contacts is configured to transfer a power signal to at least one electrical contact of the second plurality of electrical contacts while the first and second electrical connectors are coupled; wherein each of the plurality of conductive bridges are spaced apart by a distance, wherein the distance is proportionately sized based upon electrical current capacities of two adjacent conductive bridges of the plurality of conductive bridges to prevent signal interference between the two adjacent conductive bridges.

XI. Miscellaneous

Versions of the devices described above may have application in conventional medical treatments and procedures conducted by a medical professional, as well as application in robotic-assisted medical treatments and procedures.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 17/136,139, entitled "Electrosurgical Instrument System with Parasitic Energy Loss Monitor," filed on Dec. 29, 2020, published as U.S. Pub. No. 2022/0202470 on Jun. 30, 2022, the disclosure of which is incorporated by reference herein. Various suitable ways in which the teachings herein may be combined with the teachings of U.S. patent application Ser. No. 17/136,139, published as U.S. Pub. No. 2022/0202470, will be apparent to those of ordinary skill in the art in view of the teachings herein.

In addition to the foregoing, the teachings herein may be readily combined with the teachings of U.S. patent application Ser. No. 17/136,141, entitled "Energized Surgical Instrument System with Multi-Generator Output Monitoring," filed on Dec. 29, 2020, published as U.S. Pub. No. 2022/0202475 on Jun. 30, 2022, issued as U.S. Pat. No. 11,992,257 on May 28, 2024, the disclosure of which is incorporated by reference herein. Various suitable ways in which the teachings herein may be combined with the teachings of U.S. patent application Ser. No. 17/136,139, published as U.S. Pub. No. 2022/0202470, issued as U.S. Pat. No. 11,992,257, will be apparent to those of ordinary skill in the art in view of the teachings herein.

In addition to the foregoing, the teachings herein may be readily combined with the teachings of U.S. patent application Ser. No. 17/136,145, entitled "Electrosurgical Instrument with Shaft Voltage Monitor," filed on Dec. 29, 2020, published as U.S. Pub. No. 2022/0202487 on Jun. 30, 2022, the disclosure of which is incorporated by reference herein. Various suitable ways in which the teachings herein may be combined with the teachings of U.S. patent application Ser. No. 17/135,145, published as U.S. Pub. No. 2022/0202487, will be apparent to those of ordinary skill in the art in view of the teachings herein.

In addition to the foregoing, the teachings herein may be readily combined with the teachings of U.S. patent application Ser. No. 17/136,154, entitled "Electrosurgical Instrument with Electrical Resistance Monitor at Rotary Coupling," filed on Dec. 29, 2020, published as U.S. Pub. No. 2022/0202476 on Jun. 30, 2022, issued as U.S. Pat. No. 12,096,971 on Sep. 24, 2024, the disclosure of which is incorporated by reference herein. Various suitable ways in which the teachings herein may be combined with the teachings of U.S. patent application Ser. No. 17/136,154, published as U.S. Pub. No. 2022/0202476, issued as U.S. Pat. No. 12,096,971, will be apparent to those of ordinary skill in the art in view of the teachings herein In addition to the foregoing, the teachings herein may be readily combined with the teachings of U.S. patent application Ser. No. 17/136,158, entitled "Electrosurgical Instrument with Modular Component Contact Monitoring," filed on Dec. 29, 2020, published as U.S. Pub. No. 2022/0202488 on Jun. 30, 2022, issued as U.S. Pat. No. 12,011,217 on Jun. 18, 2024, the disclosure of which is incorporated by reference herein. Various suitable ways in which the teachings herein may be combined with the teachings of U.S. patent application Ser. No. 17/136,158, published as U.S. Pub. No. 2022/0202488, issued as U.S. Pat. No. 12,011,217, will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An electrosurgical system, comprising:
   (a) an instrument, including:
      (i) a body,
      (ii) an end effector coupled with a distal end of the body, wherein the end effector includes an electrode operable to apply RF energy to tissue, and
      (iii) a conductive shield coupled with the body and including a ground return, wherein the conductive shield is configured to collect a capacitive coupling current that is induced by the application of the RF energy by the electrode and to route the capacitive coupling current to the ground return;
   (b) a generator configured to provide the RF energy to the electrode;
   (c) a first ground pad having a first electrical lead that couples the first ground pad with the generator for providing a first return path for at least some of the RF energy from the generator via the first ground pad; and
   (d) a second ground pad having a second electrical lead that couples the second ground pad with the generator for providing a second return path for at least some of the RF energy from the generator via the second ground pad, wherein:
      the ground return of the conductive shield is coupled with the first electrical lead such that a first portion of the capacitive coupling current is provided to the generator via the ground return and the first electrical lead and is diverted away from the first ground pad and the second ground pad;
      the ground return of the conductive shield is further coupled with the second electrical lead such that a second portion of the capacitive coupling current is provided to the generator via the ground return and the second electrical lead simultaneously with the first portion of the capacitive coupling current and is diverted away from the first ground pad and the second ground pad; and
      the first and second portions of the capacitive coupling current are substantially equal.

2. The electrosurgical system of claim 1, wherein the RF energy has a frequency of between approximately 300 kHz and approximately 500 kHz.

3. The electrosurgical system of claim 1, further comprising:
   (a) a conductive bridge configured to electrically couple the ground return, the first electrical lead, and the second electrical lead together; and
   (b) a signal filter electrically positioned between the first electrical lead and the second electrical lead.

4. The electrosurgical system of claim 3, wherein the signal filter includes a high-pass filter.

5. The electrosurgical system of claim 3, wherein the generator is configured to provide a diagnostic signal to the first ground pad via the first electrical lead, wherein the second ground pad is configured to return at least a portion of the diagnostic signal to the generator via the second electrical lead, wherein the signal filter is configured to prevent the diagnostic signal from passing through the conductive bridge.

6. The electrosurgical system of claim 5, wherein the diagnostic signal has a frequency of between approximately 15 kHz and approximately 50 kHz.

7. The electrosurgical system of claim 1, further comprising: a transformer configured to electrically couple between the ground return, the first electrical lead, and the second electrical lead, wherein the transformer is operable to transfer the first portion of the capacitive coupling current from the conductive shield to the first electrical lead and the second portion of the capacitive coupling current from the conductive shield to the second electrical lead.

8. The electrosurgical system of claim 1, wherein the generator is configured to apply monopolar RF energy to a patient.

9. The electrosurgical system of claim 1, wherein:
   the generator is configured to provide alternating diagnostic signals between the first and second ground pads via the first and second electrical leads; and
   for each alternating diagnostic signal provided to either of the first and second ground pads, an opposing one of the first and second ground pads is configured to return at least a portion of the alternating diagnostic signal to the generator.

10. An electrosurgical system, comprising:
    (a) an instrument, including:
       (i) a body,
       (ii) an end effector coupled with a distal end of the body, wherein the end effector includes an electrode operable to apply RF energy to tissue, and
       (ii) a conductive shield coupled with the body and including a ground return, wherein the conductive shield is configured to collect a capacitive coupling current that is induced by the application of the RF energy by the electrode and to route the capacitive coupling current to the ground return;
    (b) a first ground pad having a first electrical lead, wherein the first electrical lead couples the first ground pad with a ground source for providing a first return path for at least some of the RF energy from the generator via the first ground pad;
    (c) a second ground pad having a second electrical lead, wherein the second electrical lead couples the second ground pad with the ground source for providing a second return path for at least some of the RF energy from the generator via the second ground pad; and (d) a conductive bridge configured to electrically couple the ground return of the conductive shield, the first electrical lead, and the second electrical lead together to provide a simultaneous grounding path for the ground return of the conductive shield along each of the first return path and the second return path such that a first portion of the capacitive coupling current is provided to the ground source via the ground return and the first electrical lead and a second portion of the capacitive coupling current is provided to the ground source via the ground return and the second electrical lead to prevent the first and second portions of the capacitive coupling current from being routed through the first and second ground pads, wherein the first and second portions of the capacitive coupling current are substantially equal.

11. The electrosurgical system of claim 10, wherein the conductive bridge includes a signal filter electrically positioned between the first electrical lead and the second electrical lead.

12. The electrosurgical system of claim 11, further comprising a generator configured to provide the RF energy, wherein the generator is configured to provide a diagnostic signal to the first ground pad via the first electrical lead, wherein the second ground pad is configured to return at least a portion of the diagnostic signal to the generator via the second electrical lead, wherein the signal filter prevents the diagnostic signal from passing through the conductive bridge.

13. The electrosurgical system of claim 11, wherein the signal filter includes a high-pass filter.

14. The electrosurgical system of claim 10, wherein the conductive bridge includes a transformer, wherein the transformer is operable to transfer the first portion of the capacitive coupling current from the conductive shield to the first electrical lead and the second portion of the capacitive coupling current from the conductive shield to the second electrical lead.

15. The electrosurgical system of claim 10, wherein the RF energy has a frequency of between approximately 300 kHz and approximately 500 KHz.

16. An electrosurgical system comprising:
(a) an instrument, including:
 (i) a body,
 (ii) an end effector coupled with a distal end of the body, wherein the end effector includes an electrode operable to apply RF energy to tissue, and
 (iii) a conductive shield coupled with the body and including a ground return, wherein the conductive shield is configured to collect a capacitive coupling current that is induced by the application of the RF energy by the electrode and to route the capacitive coupling current to the ground return;
(b) a generator configured to provide the RF energy to the electrode;
(c) a first ground pad electrically coupled with the generator for providing a first return path for at least some of the RF energy from the generator via the first ground pad; and
(d) a second ground pad electrically coupled with the generator for providing a second return path for at least some of the RF energy from the generator via the second ground pad, wherein:
 the ground return of the conductive shield is electrically coupled with the first return path such that a first portion of the capacitive coupling current is provided to the generator via the ground return and the first return path and bypasses the first ground pad and the second ground pad;
 the ground return of the conductive shield is electrically coupled with the second return path such that a second portion of the capacitive coupling current is provided to the generator via the ground return and the second return path and bypasses the first ground pad and the second ground pad; and
 the first and second portions of the capacitive coupling current are substantially equal.

17. The electrosurgical system of claim 16 further including a signal filter electrically coupled with each of the first ground pad, the second ground pad and the generator such that the signal filter is electrically positioned between the first return path and the second return path.

18. The electrosurgical system of claim 17, wherein the generator is configured to provide a diagnostic signal to the first ground pad via the first return path, wherein the second ground pad is configured to return at least a portion of the diagnostic signal to the generator via the second return path, wherein the signal filter is configured to prevent the diagnostic signal from passing between the first return path and the second return path.

19. The electrosurgical system of claim 16, further comprising: a transformer configured to electrically couple between the ground return, the first ground pad, and the second ground pad, wherein the transformer is operable to transfer the first portion of the capacitive coupling current from the conductive shield to the first return path and the second portion of the capacitive coupling current from the conductive shield to the second return path.

20. The electrosurgical system of claim 16, wherein:
the generator is configured to provide alternating diagnostic signals between the first and second ground pads via the first and second return paths; and
for each alternating diagnostic signal provided to either of the first and second ground pads, an opposing one of the first and second ground pads is configured to return at least a portion of the alternating diagnostic signal to the generator.

* * * * *